US 9,809,611 B2

(12) United States Patent
Eastham et al.

(10) Patent No.: US 9,809,611 B2
(45) Date of Patent: Nov. 7, 2017

(54) CARBONYLATION LIGANDS AND THEIR USE IN THE CARBONYLATION OF ETHYLENICALLY UNSATURATED COMPOUNDS

(75) Inventors: Graham Ronald Eastham, Redcar (GB); Ian Butler, Gwynedd (GB)

(73) Assignee: LUCITE INTERNATIONAL UK LIMITED, Hampshire (GB)

( * ) Notice: Subject to any disclaimer, the term of this patent is extended or adjusted under 35 U.S.C. 154(b) by 472 days.

(21) Appl. No.: 12/517,215

(22) PCT Filed: Nov. 27, 2007

(86) PCT No.: PCT/GB2007/050717
§ 371 (c)(1),
(2), (4) Date: Dec. 23, 2009

(87) PCT Pub. No.: WO2008/065448
PCT Pub. Date: Jun. 5, 2008

(65) Prior Publication Data
US 2010/0113255 A1    May 6, 2010

(30) Foreign Application Priority Data

Dec. 2, 2006    (GB) .................................. 0624114.5
Dec. 21, 2006   (GB) .................................. 0625689.5
Aug. 24, 2007   (GB) .................................. 0716530.1

(51) Int. Cl.
*B01J 31/24*    (2006.01)
*C07F 17/02*    (2006.01)
*C07F 15/00*    (2006.01)

(52) U.S. Cl.
CPC .......... *C07F 17/02* (2013.01); *C07F 15/0066* (2013.01)

(58) Field of Classification Search
None
See application file for complete search history.

(56) References Cited

U.S. PATENT DOCUMENTS

| | | |
|---|---|---|
| 3,131,204 A | 4/1964 | Sisler et al. |
| 3,564,020 A | 2/1971 | Fenton |
| 4,245,115 A | 1/1981 | Butter |
| 4,377,708 A | 3/1983 | Morris |
| 4,500,727 A | 2/1985 | Kitamura et al. |
| 4,504,684 A | 3/1985 | Fox et al. |
| 4,517,061 A | 5/1985 | Fauvarque et al. |
| 4,786,443 A | 11/1988 | Drent et al. |
| 4,818,810 A | 4/1989 | Drent |
| 4,835,250 A | 5/1989 | Drent |
| 4,868,282 A | 9/1989 | Van Broekhoven et al. |
| 4,880,903 A | 11/1989 | Van Broekhoven et al. |
| 4,900,413 A | 2/1990 | Tanaka et al. |
| 4,950,703 A | 8/1990 | Smutny |
| 4,960,926 A | 10/1990 | Drent |
| 4,960,949 A | 10/1990 | Devon et al. |
| 5,028,576 A | 7/1991 | Drent et al. |
| 5,099,062 A | 3/1992 | Drent et al. |
| 5,103,043 A | 4/1992 | Drent et al. |
| 5,149,868 A | 9/1992 | Drent |

(Continued)

FOREIGN PATENT DOCUMENTS

| | | |
|---|---|---|
| AU | 2003259322 A1 | 2/2004 |
| AU | 2006314268 A1 | 5/2007 |

(Continued)

OTHER PUBLICATIONS

Office Action for U.S. Appl. No. 12/084,575, issued by the USPTO dated Aug. 29, 2011.
Doherty et al., "Selectivity for the methoxycarbonylation of ethylene versus CO-ethylene copolymerization with catalysts based on C4-bridged bidentate phosphines and phospholes," Journal of Organometallic Chemistry, vol. 640, pp. 182-196, 2001.
Dörwald, Side Reactions in Organic Synthesis: A Guide to Successful Synthesis Design, Weinheim—Wiley-VCH, pp. ix, 1-16, 2005.
Office Action for European Application No. 07848735.2, issued by the EPO dated Sep. 9, 2011.
Office Action for Australian Application No. 2006314268, issued by the Australian Patent Office dated Nov. 11, 2010.
Office Action for European Application No. 07824927.3, issued by the EPO dated Mar. 30, 2011.

(Continued)

*Primary Examiner* — Yun Qian
(74) *Attorney, Agent, or Firm* — Venable LLP; Keith G. Haddaway; Annette K. Kwok

(57) ABSTRACT

Novel bidentate ligands of general formula (I) are described. In formula (I), A and B each independently represent a linking group; and R represents a hydrocarbyl aromatic structure. The substituent(s) $Y^i$ on the aromatic structure together have a total number $\Sigma t_i$ of atoms other than hydrogen such that $\Sigma t_i$ is greater than or equal to 4, wherein $t_i$ represents the number of atoms other than hydrogen on a particular substituent $Y^i$. i ranges from 1 to n; and n is the total number of substituent(s) $Y^i$. The groups $X^1$, $X^2$, $X^3$ and $X^4$ are joined via tertiary carbon atoms to the respective atom $Q^2$ or $Q^1$. $Q^1$ and $Q^2$ each independently represent phosphorus, arsenic, or antimony. A catalyst system and a process for the carbonylation of ethylenically unsaturated compounds utilizing the catalyst system are also described.

$$\begin{array}{c} X^1 \\ \diagdown \\ Q^2 - A - R - B - Q^1 \\ \diagup \quad\quad | \quad\quad \diagup \\ X^2 \quad\quad (Y^i)_n \quad\quad X^4 \end{array} \quad X^3 \qquad (I)$$

17 Claims, No Drawings

(56) References Cited

U.S. PATENT DOCUMENTS

| | | |
|---|---|---|
| 5,158,921 A | 10/1992 | Drent et al. |
| 5,166,116 A | 11/1992 | Drent et al. |
| 5,177,253 A | 1/1993 | Drent et al. |
| 5,179,225 A | 1/1993 | Drent et al. |
| 5,189,003 A | 2/1993 | Klusener et al. |
| 5,210,280 A | 5/1993 | Drent |
| 5,245,098 A | 9/1993 | Hamilton et al. |
| 5,246,558 A | 9/1993 | Chevigne et al. |
| 5,258,546 A | 11/1993 | Klusener et al. |
| 5,350,876 A | 9/1994 | Drent et al. |
| 5,369,074 A | 11/1994 | Drent |
| 5,436,356 A | 7/1995 | Drent et al. |
| 5,563,308 A | 10/1996 | Spindler et al. |
| 5,565,594 A | 10/1996 | Spindler et al. |
| 5,618,983 A | 4/1997 | Burke |
| 5,710,344 A | 1/1998 | Breikss et al. |
| 5,719,313 A | 2/1998 | Drent et al. |
| 5,760,264 A | 6/1998 | Brieden |
| 5,773,661 A | 6/1998 | Unruh et al. |
| 5,783,715 A | 7/1998 | Pugin |
| 5,962,732 A | 10/1999 | Burke |
| 6,015,919 A | 1/2000 | Pugin |
| 6,156,934 A | 12/2000 | Suykerbuyk et al. |
| 6,169,192 B1 | 1/2001 | Pugin et al. |
| 6,191,284 B1 | 2/2001 | Knochel et al. |
| 6,232,262 B1 | 5/2001 | Sielcken et al. |
| 6,258,979 B1 | 7/2001 | Kagan et al. |
| 6,284,919 B1 | 9/2001 | Pearson et al. |
| 6,284,925 B1 | 9/2001 | Knochel et al. |
| 6,307,065 B1 | 10/2001 | Tjaden et al. |
| 6,335,471 B1 | 1/2002 | Eastham et al. |
| 6,337,406 B1 | 1/2002 | Zhang |
| 6,348,621 B1 * | 2/2002 | Wang et al. ............ 560/232 |
| 6,391,818 B1 | 5/2002 | Bonsel et al. |
| 6,462,095 B1 | 10/2002 | Bonsel et al. |
| 6,476,255 B1 | 11/2002 | Hadden et al. |
| 6,521,769 B1 | 2/2003 | Zhang |
| 6,706,912 B2 | 3/2004 | Drent et al. |
| 6,723,882 B2 | 4/2004 | Slany et al. |
| 6,737,542 B1 | 5/2004 | Drent et al. |
| 6,743,911 B2 | 6/2004 | Drent et al. |
| 6,753,450 B2 | 6/2004 | Ahlers et al. |
| 6,844,463 B2 | 1/2005 | Slany et al. |
| 6,916,954 B2 | 7/2005 | Schafer et al. |
| 6,982,357 B2 | 1/2006 | Crabtree et al. |
| 6,984,668 B1 | 1/2006 | Eastham et al. |
| 7,026,473 B2 | 4/2006 | Drent et al. |
| 7,129,367 B2 | 10/2006 | Suzuki et al. |
| 7,148,176 B2 | 12/2006 | Beller et al. |
| 7,265,240 B2 | 9/2007 | Eastham et al. |
| 7,371,705 B2 | 5/2008 | Eastham et al. |
| 7,629,470 B2 | 12/2009 | Campos et al. |
| 8,604,236 B2 | 12/2013 | Eastham et al. |
| 9,040,445 B2 | 5/2015 | Eastham et al. |
| 2001/0044556 A1 | 11/2001 | Drent et al. |
| 2001/0051745 A1 | 12/2001 | Pearson et al. |
| 2002/0016484 A1 | 2/2002 | Drent et al. |
| 2002/0045748 A1 | 4/2002 | Drent et al. |
| 2003/0191339 A1 | 10/2003 | Schfer et al. |
| 2004/0110989 A1 | 6/2004 | Slany et al. |
| 2004/0115475 A1 | 6/2004 | Hashimoto |
| 2004/0162440 A1 | 8/2004 | Bunel et al. |
| 2005/0090694 A1 | 4/2005 | Drent et al. |
| 2006/0106259 A1 | 5/2006 | Eastham et al. |
| 2006/0122435 A1 | 6/2006 | Eastham et al. |
| 2006/0128985 A1 | 6/2006 | Eastham et al. |
| 2006/0235241 A1 | 10/2006 | Drent et al. |
| 2006/0252935 A1 | 11/2006 | Eastham et al. |
| 2008/0051475 A1 | 2/2008 | Eastham et al. |
| 2008/0086015 A1 | 4/2008 | Eastham |
| 2008/0269459 A1 | 10/2008 | Drent et al. |
| 2008/0269520 A1 | 10/2008 | Drent et al. |
| 2009/0163724 A1 | 6/2009 | Eastham et al. |
| 2009/0216041 A1 | 8/2009 | Eastham et al. |
| 2009/0234126 A1 | 9/2009 | Hartwig et al. |
| 2009/0312561 A1 | 12/2009 | Eastham et al. |
| 2010/0030036 A1 | 2/2010 | Mottram et al. |
| 2010/0113255 A1 | 5/2010 | Eastham et al. |
| 2010/0197958 A1 | 8/2010 | Eastham et al. |
| 2010/0324332 A1 | 12/2010 | Carrington-Smith et al. |
| 2012/0010413 A1 | 1/2012 | Abrecht et al. |

FOREIGN PATENT DOCUMENTS

| | | |
|---|---|---|
| BR | PI 9000965 A | 2/1991 |
| BR | PI 9510249-3 A | 11/1997 |
| BR | PI 0109239 A | 12/2002 |
| BR | PI 0313289-7 A | 7/2005 |
| CA | 2498293 A1 | 3/2004 |
| CN | 1171098 A | 1/1998 |
| CN | 1429228 A | 7/2003 |
| CN | 1478071 A | 2/2004 |
| CN | 101137611 A | 3/2008 |
| CN | 101142162 A | 3/2008 |
| DE | 19745904 A1 | 4/1999 |
| DE | 19754304 A1 | 6/1999 |
| DE | 10023470 A1 | 11/2001 |
| DE | 10037961 A1 | 2/2002 |
| EP | 0055875 A1 | 7/1982 |
| EP | 0106379 A1 | 4/1984 |
| EP | 121965 A2 | 10/1984 |
| EP | 0144118 A1 | 6/1985 |
| EP | 181014 A1 | 5/1986 |
| EP | 213671 A1 | 3/1987 |
| EP | 0227160 A2 | 7/1987 |
| EP | 0235864 A1 | 9/1987 |
| EP | 0274795 A2 | 7/1988 |
| EP | 0282142 A1 | 9/1988 |
| EP | 0305089 A1 | 3/1989 |
| EP | 0375573 A1 | 6/1990 |
| EP | 0386833 A1 | 9/1990 |
| EP | 0441447 A1 | 8/1991 |
| EP | 0489472 A2 | 6/1992 |
| EP | 0495347 A1 | 7/1992 |
| EP | 0495348 A1 | 7/1992 |
| EP | 0495547 A2 | 7/1992 |
| EP | 0495548 A2 | 7/1992 |
| EP | 0499329 A1 | 8/1992 |
| EP | 0577205 A2 | 1/1994 |
| EP | 0683764 A1 | 11/1995 |
| EP | 0728733 A1 | 8/1996 |
| EP | 0879642 A2 | 11/1998 |
| EP | 1330309 A1 | 7/2003 |
| FR | 2034147 A5 | 12/1970 |
| GB | 2006208 A | 5/1979 |
| JP | 6216737 A | 1/1987 |
| JP | 04-215851 A | 8/1992 |
| JP | H0558949 A | 3/1993 |
| JP | 06-065148 A | 3/1994 |
| JP | 08134218 A | 5/1996 |
| JP | 10-511034 A | 10/1998 |
| JP | 10 339929 A | 12/1998 |
| JP | 2001-517218 A | 10/2001 |
| JP | 2003-527365 A | 9/2003 |
| JP | 2003-528849 A | 9/2003 |
| JP | 2004-509741 A | 4/2004 |
| JP | 2004-515487 A | 5/2004 |
| JP | 2004-515537 A | 5/2004 |
| JP | 2005-535455 A | 11/2005 |
| JP | 2005-535695 A | 11/2005 |
| JP | 2007-502315 A | 2/2007 |
| JP | 2007-524700 A | 8/2007 |
| JP | 2008-505903 A | 2/2008 |
| JP | 2009-504620 A | 2/2009 |
| JP | 2009-515936 A | 4/2009 |
| JP | 2009-533409 A | 9/2009 |
| JP | 2010511600 A | 4/2010 |
| JP | 2013063440 A | 4/2013 |
| JP | 2013-091651 A | 5/2013 |
| JP | 5198267 B2 | 5/2013 |
| JP | 2013-147503 A | 8/2013 |
| JP | 5350592 B2 | 11/2013 |
| JP | 2014-208649 A | 11/2014 |
| KR | 2000-0076427 | 12/2000 |

(56) References Cited

FOREIGN PATENT DOCUMENTS

| | | | |
|---|---|---|---|
| KR | 20050084042 A | 8/2005 | |
| KR | 10-0851423 B1 | 8/2008 | |
| TW | 524801 B | 3/2003 | |
| TW | 552257 B | 9/2003 | |
| TW | 200416212 | 9/2004 | |
| TW | 200404773 | 4/2010 | |
| TW | I410280 B | 10/2013 | |
| WO | WO-96/19434 A1 | 6/1996 | |
| WO | WO-97/08124 A1 | 3/1997 | |
| WO | WO-97/040001 A1 | 10/1997 | |
| WO | WO-98/41495 A1 | 9/1998 | |
| WO | WO-98/42717 A1 | 10/1998 | |
| WO | WO-98/45040 A1 | 10/1998 | |
| WO | WO-99/47528 A1 | 9/1999 | |
| WO | WO-00/56695 A1 | 9/2000 | |
| WO | WO-01/10551 A1 | 2/2001 | |
| WO | WO-01/28972 A1 | 4/2001 | |
| WO | WO-01/38336 A1 | 5/2001 | |
| WO | WO-01/65583 A1 | 9/2001 | |
| WO | WO-01/68583 A2 | 9/2001 | |
| WO | WO-01/70659 A1 | 9/2001 | |
| WO | WO-0168583 A2 | 9/2001 | |
| WO | WO-01/72697 A2 | 10/2001 | |
| WO | WO-01/85662 A2 | 11/2001 | |
| WO | WO-0187899 A1 | 11/2001 | |
| WO | WO-02/12161 A1 | 2/2002 | |
| WO | WO-02/46143 A1 | 6/2002 | |
| WO | WO-02/48094 A1 | 6/2002 | |
| WO | WO-03/040159 A2 | 5/2003 | |
| WO | WO-03/070370 A1 | 8/2003 | |
| WO | WO-0370370 A1 | 8/2003 | |
| WO | WO-2004/014552 A1 | 2/2004 | |
| WO | WO-2004/014834 A1 | 2/2004 | |
| WO | WO-2004/024322 A2 | 3/2004 | |
| WO | WO-2004/028689 A2 | 4/2004 | |
| WO | WO 2004/050599 | 6/2004 | |
| WO | WO-200450599 A1 | 6/2004 | |
| WO | WO-2004/072088 A2 | 8/2004 | |
| WO | WO-2004/103948 A1 | 12/2004 | |
| WO | WO-2005/003070 A1 | 1/2005 | |
| WO | WO-2005/079981 A1 | 9/2005 | |
| WO | WO-2005/082830 A1 | 9/2005 | |
| WO | WO-200582830 A1 | 9/2005 | |
| WO | WO-2005/118519 A1 | 12/2005 | |
| WO | WO-2006/062467 A1 | 6/2006 | |
| WO | WO-2006/084892 A2 | 8/2006 | |
| WO | WO-2007/020379 A1 | 2/2007 | |
| WO | WO-2007109365 A2 | 9/2007 | |
| WO | WO 2007/119079 | 10/2007 | |
| WO | WO-2007119070 A1 | 10/2007 | |
| WO | WO-2008/031750 A2 | 3/2008 | |
| WO | WO-2008/065448 A1 | 6/2008 | |
| WO | WO-2008/075108 A1 | 6/2008 | |
| WO | WO-2008145976 A1 | 12/2008 | |
| WO | WO-2009010782 A1 | 1/2009 | |

OTHER PUBLICATIONS

Office Action for GCC Application No. GCC/P/2007/8136 issued by the State Intellectual Property Office of the P.R. China dated Nov. 5, 2010.
Office Action for Chinese Application No. 200580011699.0 issued by the State Intellectual Property Office of the P.R. China dated Jun. 23, 2011.
Office Action for Japanese Application based on International Application No. PCT/GB2005/000569 issued by the Patent Office of Japan dated Jun. 21, 2011.
Office Action for U.S. Appl. No. 12/297,023, issued by the USPTO dated Sep. 27, 2011.
Office Action for U.S. Appl. No. 11/990,272, issued by the USPTO dated Oct. 28, 2011.
Office Action for U.S. Appl. No. 11/990,272, issued by the USPTO dated Jul. 12, 2011.
Office Action for U.S. Appl. No. 10/589,971, issued by the USPTO dated Mar. 22, 2011.
Kirk Othmer Encyclopaedia of Chemical Terminology, vol. 9, 4th Ed., p. 783, Hydrolysis of Organic Esters, pp. 783-785 and 87, John Wiley & Sons, Jan. 1994.
Masters, Christopher, "Homogeneous Transition Metal Catalysis," Chapman and Hall, Feb. 1981 title page, contents page and pp. 4-21.
Lide et al., Handbook of Chem and Phys., 76th Ed., CRC Press, 1995, p. 8-141 6-155 to 6-177; 15-16 to 15-25.
Wang et al., "Polymer-Bound Bidentate-Phosphine-Pallalium Complex as a Catalyst in the Heck Arylation", J. Org. Chem, vol. 59, No. 18, 1994, pp. 5358-5364.
Hofmann et al., "Bis(Di-T-Butylphosphino)Methane Complexes of Rhodium: Homogeneous Alkyne Hydrosilylation by Catalyst-Dependent Alkyne Insertion Into Rh-Si or Rh-H Bonds. Molecular Structures of the Dimer [(dtbpm) RHcL]$_2$ and of the Silyl Complex (dtbpm) Rh[Si(OEt)$^{3)(PMe}$3)]", Journal of Organometallic Chemistry, vol. 490, 1995, pp. 51-70.
Lindner et al., "Catalytic Activity of Cationic Diphospalladium (II) Complexes in the Alkene/CO Copolymerization in Organic Solvents and Water in Dependence on the Length of the Alkyl Chain at the Phosphine Ligands", Journal of Organometallic Chemistry, vol. 602, 2000, pp. 173-187.
Richmond et al., "Preparation of New Catalysts by the Immobilization of Palladium(II) Species Onto Silica: an Investigation of Their Catalytic Activity for the Cyclization of Aminoalkynes", J. Am Chem. Soc., vol. 123, 2001, pp. 10521-10525.
Tamao et al., "Alkyl Group Isomerization in the Cross-Coupling Reaction of Secondary Alkyl Grignard Reagents With Organic Halides in the Presence of Nickel-Phosphine Complexes as Catalysts", Journal of the American Chemical Society, vol. 94, 1972, pp. 9268-9269.
Jones et al, "Rhodium-Catalyzed Activation and Functionalization of the C—C Bond of Biphenylene", Organometallics, vol. 20, 2001, pp. 5745-5750.
"Highly active [Pd(AcO)2(dppp(] catalyst for the CO—C2H4 copolymerization in H2O—CH3COOH solvent [dppp=1,3-bis (diphenylphosphino)propane]" Andrea Vavasori et al., Journal of Molecular Cat. A. Chem., vol. 204-205, 2003, pp. 295-303.
"Hydroesterification of styrene using an in situ formed Pd(OTs)2(PPh3)2 complex catalyst", A. Seayad et al., Journal of Molecular Cat. A. Chem., vol. 151, 2000, pp. 47-59.
"Carbon monoxide-ethylene copolymerization catalyzed by a Pd(AcO)$_2$/dpppTsOH[1] system: the promoting effect of water and of the acid", Journal of Molecular Cat. A. Chem., vol. 110, 1996, pp. 13-23.
Knight et al: "Remarkable Differences in Catalyst Activity and Selectivity fo rthe production of Methyl Propanoate versus CO-Ethylene Copolymer by a Series of palladium Complexes of Related $C_4$-Bridged Diphosphines" Organometallics 2000, 19 4957-4967.
Brunkan et al. "Effect of chiral cavities associated with molecularly imprinted platinum centers on the selectivity of ligand-exchange reactions at platinum", Journal of American Chemical Society, No. 22, pp. 6217-6225, (2000).
Brunkan et al. "Unorthodox C,O binding mode of Me$_2$BINOL in Pt(II) complexes", Journal of American Chemical Society, No. 120, pp. 11002-11003, (1998).
Andrews et al. "Regioselective complexation of unprotected carbohydrates by Platinum(II); Synthesis, structure, complexation equilibria, and hydrogen-bonding in carbonate-derived bis(phosphine)platinum(II) diolate and alditolate complexes", Journal of American Chemical Society, No. 116, pp. 5730-5740, (1994).
Hartwig, et al. "Structure and reactions of oxametallacyclobutanes and oxametallacyclobutenes of ruthenium", Organometallics, vol. 10, No. 9, pp. 3344-3362 (1991).
Konno et al. "Preparation and spectroscopic characteristics of geometrical isomers of bis[1,2-bis(dimethylphosphino)ethane]cobalt(III) complexes with thiolate ligands", The Chemical Society of Japan, No. 62, pp. 3475-3478, (1989).
Cecconi et al. "Palladium complexes with the tripodal phosphine tris(2-diphenylphosphinoethyl)amine. Synthesis and structure of

(56) References Cited

OTHER PUBLICATIONS trigonal, tetrahedral, trigonal bipyramidal, and square planar complexes", J. Chem. Soc. Dalton Trans., issue 1, pp. xvii-xx. (1989).
Miskowski et al. "Preparation and spectroscopic properties of Cobalt(III) complexes containing phosphine ligands. The electronic structural description of side-bonded dioxygen", Journal of American Chemical Society, vol. 98, No. 9, pp. 2477-2483, (1976).
Hayward et al. "Some reactions of peroxobis (triphenylphosphine)platinum(II) and analogs with carbon dioxide, carbon disulfide, and other unsaturated molecules", Journal of American Chemical Society, vol. 92, issue 20, pp. 5873-5878, (1970).
Osman, Serindag "Synthesis of some platinum(II) diphosphine complexes of the type [PtX2(P—P)] (X2=CO3; X=CH3COO, CF3COO, NCO)", Synth. React. Inorg. Met.-Org. Chem., vol. 27. No. 1, pp. 69-76, (1997).
Andrews et al. "Syntheses, spectra and structures of (diphosphine)platinum(II) carbonate complexes" Inorganic Chemistry, No. 35, pp. 5478-5483, (1996).
Latif et al. "Square planar platinum(II) complexes, crystal structures of cis-bis(triphenylphosphine) hydro(triphenylstannyl) platinum(II) and cis-bis(triphenylphosphine) hydro(triphenylsilyl) platinum(II)", Journal of Organometallic Chemistry, No. 474, pp. 217-221, (1994).
Becker et al. "Synthesis and characterization of chiral diphosphine platinum(II) Vanol and Vapol complexes", Organometallics, No. 22, pp. 3245-3249, (2003).
Becker et al. "Imprinting chiral information into rigidified dendrimers", Organometallics, No. 22, pp. 4984-4998, (2003).
Peng et al. "Chiral rodlike platinum complexes, double helical chains and potential asymmetric hydrogenation ligand based on "linear" building blocks: 1,8,9,16-tetrahydroxytetraphenylene and 1,8,9,16-tetrakis(diphenylphosphino)tetraphenylene" Journal of American Chemical Society, No. 127, pp. 9603-9611, (2005).
Wen et al. "Synthesis, resolution, and applications of 1,16-dihydroxytetraphenylene as a novel building block in molecular recognition and assembly", Journal of Organic Chemistry, No. 68, pp. 8918-8931, (2003).
Mikami et al. "Molecular design of DABNTf as a highly efficient resolving reagent for racemic Pd complex with *tropos* biphenylphosphine (BIPHEP) ligand: circular dichroism (CD) spectra of enantiopure BIPHEP-Pd complex", Chirality, No. 15, pp. 105-107, (2003).
Tudor et al. "Diasteroisomer interconversion in chiral BiphepPtX2 complexes", Organometallics, No. 19, pp. 4376-4384, (2000).
Bellabarba et al., "Synthesis, X-ray characterization and reactions of a trigonal planar palladium()) carbonyl complex", Chemical Communications, No. 15, pp. 1916-1917, (2003).
Clegg et al., "Synthesis and reactivity of palladium hydrido-solvento complexes, including a key intermediate in the catalytic methoxycarbonylation of ethane to methypropanoate", Journal of the Chemical Society, Dalton Transactions, No. 17, pp. 3300-3308 (2002).
Clegg et al., "Characterisation and dynamics of [Pd(L-L)H(solv)]+, [Pd(L-L(CH2CH3)]+ and [Pd(L-L)(C(0)Et)(THF)]+ (L-L=1,2-(CH2PBut2)2C6H4): key intermediates in the catalytic methoxycarbonylation of ethane to methylpropanoate", Organometallics, vol. 21, No. 9, pp. 1832-1840 (2002).
Edelbach et al., "Catalytic hydrogenolysis of biphenylene with platinum, palladium, and nickelphosphine complexes", Organometallics, vol. 17, No. 22, pp. 4784-4794 (1998).
Kim et al., "Synthesis and theoretical study of palladium (II) complexes with aminophosphines as 7-membered chelate rings", Bulletin of the Korean Chemical Society, vol. 18, No. 11, pp. 1162-1166 (1997).
Reddy et al., "Unexpected cross-metathesis between Si—C and Si—Si bonds", Chemical Communications, No. 16, pp. 1865-1866 (1996).

Uchimaru et al., "Ring-opening polymerization of 1,1,2,2-tetramethyl-1,2-disilacyclopentane via palladium complex-catalysed Si—Si bond metathesis", Chemistry Letters, No. 2, p. 164 (1995).
Portnoy et al., "Reactions of electron-rich arylpalladium complexes with olefins. Origin of the chelate effect in vinylation catalysis", Organometallics, vol. 13, No. 9, pp. 3465-3479 (1994).
Wurst et al., "Synthesis and structure of the platinum (0) compounds [(dipb)Pt]2(COD) and (dipb)3Pt2 and of the cluster Hg6[Pt(dipb)]4 (dipb=(iPr)2P(CH2)4P(i-Pr)2)", Zeitschrift Für Anorganische Und Allgemeine Chemie, vol. 395, pp. 239-250 (1991).
Tanaka et al., "Synthesis of ketones via carbonylation of organic halides. II. Palladium-catalysed carbonylation of organic halides with terminal acetylenes in the presence of amines. Novel acetylenic ketone synthesis", Nippon Kagaku Kaishi, No. 3, pp. 537-546 (1985).
Molander et al., "Synthesis and application of chiral cyclopropane-based ligands in palladium-catalyzed allylic alkylation", Journal of Organic Chemistry, vol. 69, No. 23, pp. 8062-8069 (2004).
Brauer et al., "Reactions of coordinated ligands. XIV. Synthesis of a tetradentate phosphorus macrocycle in a palladium (II) template", Chemische Berichte, vol. 119, No. 1, pp. 349-365 (1986).
Dias et al., "Synthesis and characterization of .eta.5-monocyclopentadienyl (p-nitrobenzonitrile)ruthenium(II) salts: second harmonic generation powder efficiencies", Journal of Organometallic Chemistry, vol. 475, No. 1-2, pp. 241-245 (1994).
Pugh, R. I. et al. "Tandem isomerisation-carbonylation catalysis: highly active palladium(II) catalysts for the selective methoxycarbonylation of internal alkenes to linear esters", Chemical Communications—Chemcom, Royal Society of Chemistry, GB, No. 16, (Aug. 21, 2001), pp. 1476-1477.
Cullen et al, "Structure of the Hydrogenation Catalyst [(PP)Rh(NBD)]ClO4, (PP)=( 5-[(CH3)3C]2PC5H4)2Fe, and Some Comparative Rate Studies," Organometallics, vol. 2, pp. 714-719, 1983.
Abbenhuis et al., "Successful Application of a "Forgotten" Phosphine in Asymmetric Catalysis: A 9-Phosphabicyclo[3.3.1]non-9-γl Ferrocene Derivative as a Chiral Ligand," Organometallics, vol. 14, pp. 759-766, 1995.
Olah, George A., et al., "AlCl3-Catalyzed Dichlorophosphorylation of Saturated Hydrocarbons with PCl3 in Methylene Chloride Solution," *J. Org. Chem.*, 1990, 55, 1224-1227.
Wei-Yong Yu, et al., "Preparation of Polymer-Protected Pt/Co Bimetallic Colloid and its Catalytic Properties in Selective Hydrogenation of Cinnamaldehyde to Cinnamyl Alcohol," Polymers For Advanced Technologies, GB, John Wiley and Sons, Chichester, Aug. 1, 1996, 719-722, vol. 7, No. 8.
Tolman, "Phosphorous Ligand Exchange Equilibria on Zerovalent Nickel. A Dominant Role for Steric Effects," Journal of the American Chemical Society, vol. 92, No. 10, pp. 2956-2965, 1970.
Tolman, "Steric Effects of Phosphorous Ligands in Organometallic Chemistry and Homogeneous Catalysis," Chemical Reviews, vol. 77, No. 3, pp. 313-348, 1977.
Grimmer, et al., "Zirconium bis-cyclopentadienyl compounds: An investigation into the influence of substituent effects on the ethene polymerisation behaviour of (CpR)2ZrCl2/MAO catalysts," Journal of Molecular Catalysis A: Chemical, vol. 188, No. 1-2, pp. 105-113, 2002.
Machine Translation of JP 08-134218, May 28, 1996.
Office Action for U.S. Appl. No. 11/597,787, issued by the USPTO dated Oct. 8, 2008.
Office Action for U.S. Appl. No. 11/597,787, issued by the USPTO dated Oct. 8, 2009.
Office Action for U.S. Appl. No. 11/597,787, issued by the USPTO dated May 20, 2009.
Office Action for U.S. Appl. No. 10/561,912, issued by the USPTO dated Aug. 25, 2008.
Office Action for U.S. Appl. No. 10/561,912, issued by the USPTO dated Sep. 2, 2009.
Office Action for U.S. Appl. No. 10/561,912, issued by the USPTO dated Jan. 14, 2008.
Office Action for U.S. Appl. No. 10/561,912, issued by the USPTO dated Feb. 11, 2009.

(56) References Cited

OTHER PUBLICATIONS

Office Action for U.S. Appl. No. 10/536,801, issued by the USPTO dated Apr. 8, 2008.
Office Action for U.S. Appl. No. 10/536,801, issued by the USPTO dated Jan. 7, 2010.
Office Action for U.S. Appl. No. 10/536,801, issued by the USPTO dated Jun. 17, 2009.
Office Action issued by the USPTO for U.S. Appl. No. 10/589,971 dated Jul. 27, 2010.
Office Action issued by the USPTO in U.S. Appl. No. 12/518,320 dated Dec. 8, 2010.
Oblad et al., Catalysis and Catalysts. In McKetta ed, *Encyclopedia of Chemical Processing and Design*, pp. 420-490, 1978.
Hartley, Supported Metal Complexes: A New Generation of Catalysts, Section 1.3, pp. 1, 9, 1985.
Armor, "Perspective: Do you really have a better catalyst?," Applied Catalysis A: General, vol. 282, pp. 1-4, 2005.
Hagen, "Industrial Catalysis: A Practical Approach," pp. v-xvii and 1-6, 2006.
Office Action for Taiwanese Application No. 094104929 issued by the Intellectual Property Office of Taiwan dated Sep. 21, 2011.
Rucklidge et al., "The methoxycarbonylation of vinyl acetate catalyzed by palladium complexes of [1,2-phenylenebis(methylene)]bis[di(tert-butyl)phosphine]", Helvetica Chimica ACTA, 89(8), pp. 1783-1800, (2006).
Clegg et al., "Highly active and selective catalysts for the production of methyl propanoate via the methoxycarbonylation of ethane", Chemical Communications, pp. 1877-1878 (1999).
Argouarch, et al., "Synthesis of Some Ferrocene-Based 1,3(phosphanes) with Planar Chirality as the Sole Source of Chirality", European Journal of Organic Chemistry, 2000, vol. 16 pp. 2885-2891.
Examination Report issued by the State Intellectual Property Office of the P.R. China in Application No. GCC/P/2007/8136 dated Nov. 5, 2010.
Examiners First Report issued in Australian Application No. 2007327051 dated May 9, 2012.
Godard, et al., "Systematic Study of the Asymmetric Methoxycarbonylation of Styrene Catalyzed by Palladium Systems Containing Chiral Ferrocenyl Diphosphine Ligands", Helvetica Chimica Acta, 2006 vol. 89(8) pp. 1610-1622.
Gray et al., "The Di-t-Butylphosphinyl Directed *ortho* Metalation Group, Synthesis of Hindered Dialkylarylphosphines," Synlett Letters, vol. 4, pp. 422-424 (1998).
International Preliminary Report on Patentability issued in Application No. PCT/GB2010/052093 dated Jun. 28, 2012.
International Search Report issued in International Application No. PCT/GB2009/050780 dated Oct. 15, 2009.
International Search Report issued in International Application No. PCT/GB2010/052093 dated Apr. 8, 2011.
International Search Report issued in International Application No. PCT/GB2010/052214 dated Mar. 30, 2011.
Japanese Notice of Reasons for Rejection issued in Application No. 2008-525618 dated Apr. 3, 2012.
Japanese Notice of Reasons for Rejection issued in Application No. 2008-540675 dated May 22, 2012.
Kraatz et al., "The reactions of tridentate cationic palladium (II) complexes with olefins and nucleophiles," The Journal of Organometallic Chemistry, vol. 488, No. 1, pp. 223-232 (1995).
Ooka et al., "Highly active and selective palladium catalyst for hydroesterification of styrene and vinyl acetate promoted by polymeric sulfonic acids," Chemical Communications, pp. 1173-1175 (2005).
Rucklidge, et al., "Methoxycarbonylation of vinyl acetate catalysed by palladium complexes of bis(ditertiarybutylphosphinomethyl) benzene and related ligands", Chemical Communications, 2005, vol. 9 pp. 1176-1178.
Russian Office Action issued in Application No. 201170142/28 dated Apr. 20, 2012.
United Kingdom Search Report issued in Application No. GB 1000078.4 dated May 6, 2010.
United Kingdom Search Report issued in Application No. GB0812297.0 dated Jun. 17, 2009.
United Kingdom Search Report issued in Application No. GB0921876.9 dated Oct. 29, 2010.
Wang, et al., "Synthesis and Use in Asymmetric Hydrogenations of Solely Planar Chiral 1,2-Disubstituted and 1,2,3-Trisubstituted Ferrocenyl Diphosphines: A Comparative Study", Organometallics, 2007, vol. 26, pp. 3530-3540.
Written Opinion of the International Searching Authority issued in International Application No. PCT/GB2009/050780 dated Oct. 15, 2009.
Written Opinion of the International Searching Authority issued in International Application No. PCT/GB2010/052093 dated Apr. 8, 2011.
Written Opinion of the International Searching Authority issued in International Application No. PCT/GB2010/052214 dated Mar. 30, 2011.
Examination Report issued from the State Intellectual Property Office of P.R. China issued in Application No. GCC/P/2007/9585 dated Jan. 20, 2012.
Notice of Reason for Rejection issued from the Japanese Office Action in Japanese Application No. 2006-553662 dated Sep. 25, 2012.
Notice of Reason for Rejection issued from the Japanese Office Action in Japanese Application No. 2008-525618 dated Sep. 25, 2012.
Notice of Reasons for Rejection issued from the Japanese Patent Office in Japanese Application No. 2009-504833 dated Jul. 31, 2012.
Notice of Reexamination issued from the Patent Reexamination Board of State Intellectual Property Office of P.R. China in Chinese Application No. 200580011699.0 dated Jul. 30, 2012.
Office Action issued from the Eurasian Patent Organization issued in Application No. 200970528/28 dated Aug. 15, 2012.
Office Action issued in Chinese Application No. 200780044657.6 dated Mar. 20, 2013.
Office Action issued in Chinese Application No. 200980125824.9 dated Feb. 22, 2013.
Office Action issued in Eurasian Application No. 201170142.
Office Action issued in European Application No. 09 772 854.7 dated Apr. 23, 2013.
Office Action issued in Korean Application No. 10-2008-7006106 dated Apr. 24, 2013.
Office Action issued in Malaysian Application No. PI20092250 dated Mar. 29, 2013.
Office Action issued in Mexican Application No. MX/a/2008/001974 dated Mar. 11, 2013.
Office Action issued in Taiwanese Application No. 096145458 dated Mar. 8, 2013.
Office Action issued in Taiwanese Application No. 095141340 dated Apr. 12, 2013.
Kiss, "Palladium-catalyzed Reppe Carbonylation," Chem. Rev. 2001, 101(11): 3435 (Abstract Only).
Notice of Allowance issued in U.S. Appl. No. 11/990,272 dated Jul. 25, 2013.
Office Action issued in Indian Application No. 1366/DELNP/2003 dated Jul. 4, 2013.
Office Action issued in Mexican Application No. MX/a/2010/014404 dated Jun. 25, 2013.
Office Action issued in U.S. Appl. No. 10/589,971 dated Aug. 8, 2013.
Office Action issued in U.S. Appl. No. 13/002,406 dated Aug. 19, 2013.
White et al., "Basic Energy Sciences Advisory Committee Subpanel Workshop Report," Opportunities for Catalysis in the 21st Century, 2002, pp. 1-47.
Written Opinion of the Intellectual Property Office of Singapore issued in Application No. 201204384-0 dated Jul. 5, 2013.
First Examination Report issued in Indian Application No. 841/MUMNP/2009 dated Nov. 29, 2012.

(56) References Cited

OTHER PUBLICATIONS

Notice of Allowance issued in U.S. Appl. No. 12/297,023 dated Dec. 26, 2012.
Notice of Allowance issued in U.S. Appl. No. 12/297,023 dated Feb. 21, 2013.
Office Action issued in Canadian Application No. 2,618,574 dated Dec. 7, 2012.
Office Action issued in Canadian Application No. 2,626,107 dated Nov. 23, 2012.
Office Action issued in Chinese Application No. 200580011699.0 dated Jan. 14, 2013.
Office Action issued in European Application No. 09 772 854.7 dated Oct. 5, 2012.
Office Action issued in Japanese Application No. 2008-540675 dated Nov. 13, 2012.
Office Action issued in Japanese Application No. 2009-538795 dated Feb. 19, 2013.
Office Action issued in Taiwanese Application No. 095128759 dated Jan. 3, 2013.
Office Action issued in Taiwanese Application No. 096113047 dated Jan. 22, 2013.
Office Action issued in U.S. Appl. No. 11/990,272 dated Feb. 6, 2013.
Office Action issued in U.S. Appl. No. 13/002,406 dated Mar. 15, 2013.
Letter Reporting Office Action issued in Australian Application No. 2009265367 dated Aug. 20, 2013.
Letter Reporting Office Action issued in Mexican Application No. MX/a/2009/005568 dated Sep. 12, 2013.
Office Action issued in Canadian Application No. 2,626,107 dated Aug. 8, 2013.
Office Action issued in Canadian Application No. 2,671,409 dated Aug. 23, 2013.
Office Action issued in Chinese Application No. 200780044657.6 dated Sep. 23, 2013.
Office Action issued in Eurasian Application No. 200801345 dated Jun. 27, 2013.
Office Action issued in Eurasian Application No. 201170142/28 dated Aug. 23, 2013.
Office Action issued in Eurasian Application No. 201290605 dated Aug. 22, 2013.
Office Action issued in Indian Application No. 3292/DELNP/2008 dated Sep. 20, 2013.
Office Action issued in Malaysian Application No. PI2011000006 dated Sep. 30, 2013.
Office Action issued in Singapore Application No. SE 2013 01311V dated Aug. 9, 2013.
Office Action for U.S. Appl. No. 12/084,575, issued by the USPTO dated Mar. 19, 2012.
Office Action for U.S. Appl. No. 12/297,023, issued by the USPTO dated Apr. 12, 2012.
Andrews et al., "Syntheses, Spectra, and Structures of (Diphosphine)platinum(II) Carbonate Complexes," Inorganic Chemistry, vol. 35, No. 19, pp. 5478-5483, 1996.
Office Action issued in Korean Patent Office dated Jan. 12, 2012, English translation.
Office Action for U.S. Appl. No. 11/990,272, issued by the USPTO dated May 2, 2012.
Notice of Allowance issued in U.S. Appl. No. 13/002,406 dated Apr. 9, 2014.
Office Action issued in Brazilian Patent Application. PI0507805-9 dated Mar. 24, 2014.
Office Action issued in Canadian Patent Application No. 2,626,107 dated May 9, 2014.
Office Action issued in Chinese Patent Application No. 201080060676.X dated Jan. 27, 2014.
Office Action issued in Eurasian Patent Application No. 200801345/28 dated Jan. 31, 2014.
Office Action issued in Eurasian Patent Application No. 201290605 dated Mar. 12, 2014.
Office Action issued in European Patent Application No. 09772854.7 dated Mar. 11, 2014.
Office Action issued in European Patent Application No. 10172689.1 dated May 30, 2014.
Office Action issued in European Patent Application No. 10172698.1 dated May 30, 2014.
Office Action issued in Gulf Cooperation Council Patent Application No. GCC/P/2005/17210 dated Mar. 5, 2014.
Office Action issued in Japanese Patent Application No. 2009-538795 dated Jan. 21, 2014.
Office Action issued in Japanese Patent Application No. 2013-051058 dated Apr. 8, 2014.
Office Action issued in Korean Patent Application No. 10-2009-7012397 dated Jan. 22, 2014.
Office Action issued in Malaysia Patent Application No. PI20081580 dated Feb. 14, 2014.
Office Action issued in Mexican Application No. MX/a/2010/014404 dated Mar. 31, 2014.
Office Action issued in Mexican Patent Application No. MX/a/2009/005568 dated Mar. 10, 2014.
Office Action issued in Taiwanese Patent Application No. 098122672 dated Mar. 4, 2014.
Office Action issued in Taiwanese Patent Application No. 095141340 dated Mar. 21, 2014.
Office Action issued in U.S. Appl. No. 12/084,575 dated Apr. 25, 2014.
Imwinkelried, "Catalytic Asymmetric Hydrogenation in the Manufacture of d-Biotin and Dextromethorphan," NSCS Spring Meeting 97: Industrial Asymmetric Synthesis, Chimia 51 (1997) 300-302.
Lee et al., "improved Catalysts for the Palladium-Catalyzed Synthesis of Oxindoles by Amide α-Arylation, Rate Acceleration, Use of Aryl Chloride Substrates, and a New Carbene Ligand for Asymmetric Transformations," J. Org. Chem, 2001, 66, 3402-3415.
Letter dated Nov. 27, 2013 reporting Office Action issued in Mexican Application No. MX/a/2010/014404.
Office Action issued in Australian Application No. 2010332501 dated Sep. 5, 2013.
Office Action issued in Chinese Application No. 200980125824.9 dated Oct. 15, 2013.
Office Action issued in Chinese Application No. 201080062848.7 dated Dec. 23, 2013.
Office Action issued in Eurasian Application No. 200970528 dated Nov. 18, 2013.
Office Action issued in Eurasian Application No. 201290514/28 dated Oct. 28, 2013.
Office Action issued in European Application No. 10172689.1 dated Dec. 5, 2013.
Office Action issued in European Application No. 10172698.2 dated Dec. 5, 2013.
Office Action issued in European Application No. 10803478.6 dated Dec. 20, 2013.
Office Action issued in Japanese Application No. 2011-515634 dated Dec. 17, 2013.
Office Action issued in Korean Application No. 10-2008-7014580 dated Jan. 15, 2014.
Office Action issued in Taiwanese Application No. 096145458 dated Oct. 9, 2013.
Office Action issued in U.S. Appl. No. 12/517,215 dated Mar. 12, 2014.
Office Action issued in U.S. Appl. No. 10/589,971 dated Mar. 6, 2014.
Notice of Allowance issued in U.S. Appl. No. 10/589,971 dated Dec. 5, 2014.
Notice of Allowance issued in U.S. Appl. No. 13/002,406 dated Jul. 3, 2014.
Notice of Allowance issued in U.S. Appl. No. 13/520,523 dated Jun. 23, 2014.
Notice of Allowance issued in U.S. Appl. No. 13/520,523 dated Oct. 14, 2014.
Office Action issued in U.S. Appl. No. 13/516,176 dated Oct. 9, 2014.

(56) References Cited

OTHER PUBLICATIONS

Pugh et al., "Methoxycaronylation versus Hydroacylation of Ethene; Dramatic Influence of the Ligand in Cationic Palladium Catalysis," Adv. Synth. Catal., 2002, vol. 344, No. 8, pp. 837-840.
Office Action issued in U.S. Appl. No. 12/084,575 dated Jan. 2, 2015.
Supplemental Notice of Allowance issued in U.S. Appl. No. 13/520,523 dated Feb. 10, 2015.
Office Action issued in U.S. Appl. No. 12/084,575 dated Jul. 24, 2015.
Office Action issued in U.S. Appl. No. 13/516,176 dated Aug. 19, 2015.
Office Action issued in U.S. Appl. No. 13/516,176 dated Mar. 6, 2015.
Corrected Notice of Allowability issued in U.S. Appl. No. 10/589,971 dated Mar. 24, 2015.
Office Action issued in U.S. Appl. No. 13/516,176 dated Jan. 22, 2016.
Office Action issued in U.S. Appl. No. 12/517,215 dated Jan. 4, 2016.
Notice of Allowance issued in U.S. Appl. No. 12/084,575 dated Jan. 14, 2016.
"Basic Energy Sciences Advisory Committee Subpanel Workshop Report," Opportunities for catalysis in the 21st century, 2002, p. 1-46.
Hessler et al., "Synthesis and coordination chemistry of hemilabile P, N-hybrid ligands with terminal 2-pyridyl or groups," Chemische Berichte, Germany 1994, 127(3): 481-488.
Hessler et al., "Water Soluble Cationic Phosphine Ligands Containing m-Guanidinium Phenyl Moieties," Syntheses and Applications in Aqueous Heck Type Reaactions, Journal of Organic Chemistry, 1997, 62(8): 2362-2369.

\* cited by examiner

CARBONYLATION LIGANDS AND THEIR USE IN THE CARBONYLATION OF ETHYLENICALLY UNSATURATED COMPOUNDS

The present invention relates to the novel bidentate ligands, novel catalyst systems incorporating such ligands, and their use in the carbonylation of ethylenically unsaturated compounds.

The carbonylation of ethylenically unsaturated compounds using carbon monoxide in the presence of an alcohol or water and a catalyst system comprising a group 6, 8, 9 or 10 metal, for example, palladium, and a phosphine ligand, for example an alkyl phosphine, cycloalkyl phosphine, aryl phosphine, pyridyl phosphine or bidentate phosphine, has been described in numerous European patents and patent applications, for example EP-A-0055875, EP-A-04489472, EP-A-0106379, EP-A-0235864, EP-A-0274795, EP-A-0499329, EP-A-0386833, EP-A-0441447, EP-A-0489472, EP-A-0282142, EP-A-0227160, EP-A-0495547 and EP-A-0495548. In particular, EP-A-0227160, EP-A-0495547 and EP-A-0495548 disclose that bidentate phosphine ligands provide catalyst systems which enable high reaction rates to be achieved. C3 alkyl bridges between the phosphorus atoms are exemplified in EP0495548 together with tertiary butyl substituents on the phosphorus.

WO96/19434 subsequently disclosed that a particular group of bidentate phosphine compounds having an aryl bridge could provide remarkably stable catalysts which require little or no replenishment; that use of such bidentate catalysts leads to reaction rates which are significantly higher than those previously disclosed; and that little or no impurities are produced at high conversions.

WO 01/68583 discloses rates for the same process as WO 96/19434 when used for higher alkenes and when in the presence of an externally added aprotic solvent.

WO 98/42717 discloses a modification to the bidentate phosphines used in EP0495548 wherein one or both phosphorus atoms are incorporated into an optionally substituted 2-phospha-tricyclo[3.3.1.1 {3,7}]decyl group or a derivative thereof in which one or more of the carbon atoms are replaced by heteroatoms ("2-PA" group). The examples include a number of alkoxycarbonylations of ethene, propene and some higher terminal and internal olefins.

WO 03/070370 extends the teaching of WO 98/42717 to bidentate phosphines having 1, 2 substituted aryl bridges of the type disclosed in WO96/19434. The suitable olefin substrates disclosed include several types having various substituents.

WO 04/103948 describes both the above types of ligand bridges as useful for butadiene carbonylation and WO 05/082830 describes a selection of WO 04/103948 where the tertiary carbon substituents are different on the respective phosphorus atoms.

It has now been found that by further substituting the aromatic structure of the aryl bridge of the type described in WO 96/19434, WO 01/68583 and WO 03/070370 more stable catalysts and hence higher TON's can be achieved.

According to the first aspect of the present invention there is provided a novel bidentate ligand of general formula (I)

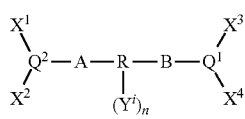
(I)

wherein:
A and B each independently represent a lower alkylene linking group;
R represents a hydrocarbyl aromatic structure having at least one aromatic ring to which $Q^1$ and $Q^2$ are each linked, via the respective linking group, on available adjacent cyclic atoms of the at least one aromatic ring and which is substituted with one or more substituent(s) $Y^i$ on one or more further aromatic cyclic atom(s) of the aromatic structure;
wherein the substituent(s) $Y^i$ on the aromatic structure together have a total number $\Sigma t_i$ of atoms other than hydrogen such that $\Sigma t_i$ is greater than or equal to 4, wherein $t_i$ represents the number of atoms other than hydrogen on a particular substituent $Y^i$;
the groups $X^1$, $X^2$, $X^3$ and $X^4$ independently represent univalent radicals of up to 30 atoms having at least one tertiary carbon atom or $X^1$ and $X^2$ and/or $X^3$ and $X^4$ together form a bivalent radical of up to 40 atoms having at least two tertiary carbon atoms wherein each said univalent or bivalent radical is joined via said at least one or two tertiary carbon atoms respectively to the respective atom $Q^1$ or $Q^2$;
$Q^1$ and $Q^2$ each independently represent phosphorus, arsenic or antimony; n is the total number of substituent(s) $Y^i$; and
i ranges from 0.1 to n.

The above novel bidentate ligands have been found to have surprisingly improved stability in carbonylation reactions. Typically, the turnover number (TON) (moles of metal/moles of product) for the carbonylation reaction, especially, hydroxy- or alkoxy-carbonylation is close to or greater than that for 1,3-bis(di-t-butylphosphino)propane reacted under the same conditions, more preferably, greater than 1,2-bis(di-t-butylphosphinomethyl)benzene reacted under the same conditions. Preferably, such conditions are in continuous reactions but batch reactions will also benefit.

Therefore, according to a second aspect of the present invention there is provided a process for the carbonylation of ethylenically unsaturated compounds comprising reacting said compound with carbon monoxide in the presence of a source of hydroxyl groups and of a catalyst system, the catalyst system obtainable by combining:
(a) a metal of Group 8, 9 or 10 or a compound thereof: and
(b) a bidentate ligand of general formula (I)

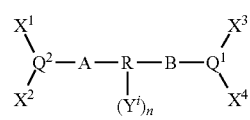

wherein:
A and B each independently represent lower alkylene linking groups;
R represents a hydrocarbyl aromatic structure having at least one aromatic ring to which $Q^1$ and $Q^2$ are each linked, via the respective linking group, on available adjacent cyclic atoms of the at least one aromatic ring and which is substituted with one or more substituent(s) $Y^i$ on one or more further aromatic cyclic atom(s) of the aromatic structure;
wherein the substituent(s) $Y^i$ on the aromatic structure together have a total number $\Sigma t_i$ of atoms other than hydrogen such that $\Sigma t_i$ is greater than or equal to 4, wherein $t_i$ represents the number of atoms other than hydrogen on a particular substituent $Y^i$;
the groups $X^1$, $X^2$, $X^3$ and $X^4$ independently represent univalent radicals of up to 30 atoms having at least one tertiary carbon atom or $X^1$ and $X^2$ and/or $X^3$ and $X^4$ together form a bivalent radical of up to 40 atoms having at least two tertiary carbon atoms, wherein each said univalent or bivalent radical is joined via said at least one or two tertiary carbon atoms respectively to the respective atom $Q^1$ or $Q^2$; and $Q^1$ and $Q^2$ each independently represent phosphorus, arsenic or antimony;

n is the total number of substituent(s) $Y^i$;

i ranges from 1 to n; and, optionally, a source of anions.

Typically, when there is more than one substituent $Y^i$, hereinafter also referred to as simply Y, any two may be located on the same or different aromatic cyclic atoms of the aromatic structure. Preferably, there are ≤10 Y groups, i.e., n is 1 to 10, more preferably there are 1-6 Y groups, and most preferably there are 1-4 Y groups on the aromatic structure and, especially, there are 1, 2 or 3 substituent Y groups on the aromatic structure. The substituted cyclic aromatic atoms may be carbon or hetero, but are preferably carbon.

Preferably, $\Sigma t_i$ is between 4-100, more preferably, 4-60, most preferably, 4-20, especially 4-12.

Preferably, when there is one substituent Y, Y represents a group which is at least as sterically hindering as phenyl and when there are two or more substituents Y they are each as sterically hindering as phenyl and/or combine to form a group which is more sterically hindering than phenyl.

By sterically hindering herein, whether in the context of the groups $R^1$-$R^{12}$ described hereinafter or the substituent Y, we mean the term as readily understood by those skilled in the art but for the avoidance of any doubt, the term more sterically hindering than phenyl can be taken to mean having a lower degree of substitution (DS) than $PH_2Ph$ when $PH_2Y$ (representing the group Y) is reacted with $Ni(0)(CO)_4$ in eightfold excess according to the conditions below. Similarly, references to more sterically hindering than t-butyl can be taken as references to DS values compared with $PH_2$t-Bu etc. If two Y groups are being compared and $PHY^1$ is not more sterically hindered than the reference then $PHY^1Y^2$ should be compared with the reference. Similarly, if three Y groups are being compared and $PHY^1$ or $PHY^1Y^2$ are not already determined to be more sterically hindered than the standard then $PY^1Y^2Y^3$ should be compared. If there are more than three Y groups they should be taken to be more sterically hindered than t-butyl.

Steric hindrance in the context of the invention herein is discussed on page 14 et seq of "Homogenous Transition Metal Catalysis—A Gentle Art", by C. Masters, published by Chapman and Hall 1981.

Tolman ("Phosphorus Ligand Exchange Equilibria on Zerovalent Nickel. A Dominant Role for Steric Effects", Journal of American Chemical Society, 92, 1970, 2956-2965) has concluded that the property of the ligands which primarily determines the stability of the Ni(O) complexes is their size rather than their electronic character.

To determine the relative steric hindrance of a group Y the method of Tolman to determine DS may be used on the phosphorus analogue of the group to be determined as set out above.

Toluene solutions of $Ni(CO)_4$ were treated with an eightfold excess of phosphorus ligand; substitution of CO by ligand was followed by means of the carbonyl stretching vibrations in the infrared spectrum. The solutions were equilibrated by heating in sealed tubes for 64 hr at 100°. Further heating at 100° for an additional 74 hrs did not significantly change the spectra. The frequencies and intensities of the carbonyl stretching bands in the spectra of the equilibriated solutions are then determined. The degree of substitution can be estimated semiquantitatively from the relative intensities and the assumption that the extinction coefficients of the bands are all of the same order of magnitude. For example, in the case of $P(C_6H_{22})_3$ the $A_1$ band of $Ni(CO)_3L$ and the $B_1$ band of $Ni(CO)_2L_2$ are of about the same intensity, so that the degree of substitution is estimated at 1.5. If this experiment fails to distinguish the respective ligands then the diphenyl phosphorus $PPh_2H$ or di-t-butyl phosphorus should be compared to the $PY_2H$ equivalent as the case may be. Still further, if this also fails to distinguish the ligands then the $PPh_3$ or $P(^tBu)_3$ ligand should be compared to $PY_3$, as the case may be. Such further experimentation may be required with small ligands which fully substitute the $Ni(CO)_4$ complex.

The group Y may also be defined by reference to its cone angle which can be defined in the context of the invention as the apex angle of a cylindrical cone centred at the midpoint of the aromatic ring. By midpoint is meant a point in the plane of the ring which is equidistant from the cyclic ring atoms.

Preferably, the cone angle of the at least one group Y or the sum of the cone angles of two or more Y groups is at least 100, more preferably, at least 200, most preferably, at least 30°. Cone angle should be measured according to the method of Tolman {C. A. Tolman Chem. Rev. 77, (1977), 313-348} except that the apex angle of the cone is now centred at the midpoint of the aromatic ring. This modified use of Tolman cone angles has been used in other systems to measure steric effects such as those in cyclopentadienyl zirconium ethene polymerisation catalysts (Journal of Molecular Catalysis: Chemical 188, (2002), 105-113).

The substituents Y are selected to be of the appropriate size to provide steric hindrance with respect to the active site between the $Q^4$ and $Q^2$ atoms. However, it is not known whether the substituent is preventing the metal leaving, directing its incoming pathway, generally providing a more stable catalytic confirmation, or acting otherwise.

A particularly preferred ligand is found when Y represents —$SR^{40}R^{41}R^{42}$ wherein S represents Si, C, N, S, O or aryl and $R^{40}R^{41}R^{42}$ are as defined hereinafter. Preferably each Y and/or combination of two or more Y groups is at least as sterically hindering as t-butyl.

More preferably, when there is only one substituent Y, it is at least as sterically hindering as t-butyl whereas where there are two or more substituents Y, they are each at least as sterically hindering as phenyl and at least as sterically hindering as t-butyl if considered as a single group.

Preferably, when S is aryl, $R^{40}$, $R^{44}$ and $R^{42}$ are independently hydrogen, alkyl, —$BQ^3$-$X^3(X^4)$ (wherein B, $X^3$ and $X^4$ are as defined herein and $Q^3$ is defined as $Q^4$ or $Q^2$ above), phosphorus, aryl, arylene, alkaryl, arylenalkyl, alkenyl, alkynyl, het, hetero, halo, cyano, nitro, —$OR^{19}$, $OC(O)R^{20}$, $C(O)R^{21}$, $C(O)OR^{22}$, —$N(R^{23})R^{24}$, —$C(O)N(R^{25})R^{26}$, —$SR^{29}$, —$C(O)SR^{30}$, —$C(S)N(R^{27})R^{28}$, —$CF_3$, —$SiR^{71}R^{72}R^{73}$ or alkylphosphorus.

$R^{19}$-$R^{30}$ referred to herein may independently be generally selected from hydrogen, unsubstituted or substituted aryl or unsubstituted or substituted alkyl, in addition $R^{21}$ may be nitro, halo, amino or thio.

Preferably, when S is Si, C, N, S or O, $R^{40}$, $R^{41}$ and $R^{42}$ are independently hydrogen, alkyl, phosphorus, aryl, arylene, alkaryl, aralkyl, arylenalkyl, alkenyl, alkynyl, het, hetero, halo, cyano, nitro, —$OR^{19}$, $OC(O)R^{20}$, $C(O)R^{21}$, $C(O)OR^{22}$, —$N(R^{23})R^{24}$, —$C(O)N(R^{25})R^{26}$, —$SR^{29}$, —$C(O)SR^{30}$, —$C(S)N(R^{2-7})R^{28}$, —$CF_3$, —$SiR^{71}R^{72}R^{73}$, or alkylphosphorus wherein at least one of $R^{40}$-$R^{42}$ is not hydrogen and wherein $R^{19}$-$R^{30}$ are as defined herein; and $R^{71}$-$R^{73}$ are defined as $R^{40}$-$R^{42}$ but are preferably $C_1$-$C_4$ alkyl or phenyl.

Preferably, S is Si, C or aryl. However, N, S or O may also be preferred as one or more of the Y groups in combined or in the case of multiple Y groups. For the avoidance of doubt, as oxygen or sulphur can be bivalent, $R^{40}$-$R^{42}$ can also be lone pairs.

Preferably, in addition to group Y, the aromatic structure may be unsubstituted or, when possible be further substituted with groups selected from Y (on the non-aromatic cyclic atoms), alkyl, aryl, arylene, alkaryl, aralkyl, arylenalkyl, alkenyl, alkynyl, het, hetero, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$, —$C(S)N(R^{2-7}) R^{28}$, —$CF_3$, —$SiR^{21}R^{72}R^{23}$, or alkylphosphorus wherein $R^{19}$-$R^{30}$ are as defined herein and in the case of Y or a group fulfilling the definition of Y of the first aspect the attachment is to a non-cyclic aromatic atom of the aromatic structure; and $R^{71}$-$R^{73}$ are defined as $R^{40}$-$R^{42}$ but are preferably $C_1$-$C_4$ alkyl or phenyl. In addition, the at least one aromatic ring can be part of a metallocene complex, for instance when R is a cyclopentadienyl or indenyl anion it may form part of a metal complex such as ferrocenyl, ruthenocyl, molybdenocenyl or indenyl equivalents.

Such complexes should be considered as aromatic structures within the context of the present invention so that, when they include more than one aromatic ring, the substituent(s) $Y^i$ may be on the same aromatic ring as that to which the $Q^1$ and $Q^2$ atoms are linked or a further aromatic ring of the structure. For instance, in the case of a metallocene, the substituent $Y^i$ may be on any one or more rings of the metallocene structure and this may be the same or a different ring to which $Q^1$ and $Q^2$ are linked.

Suitable metallocene type ligands which may be substituted with a group Y as defined herein will be known to the skilled person and are extensively defined in WO 04/024322. A particularly preferred Y substituent for such aromatic anions is when S is Si.

In general, however, when S is aryl, the aryl may be further unsubstituted or substituted with, in addition to $R^{40}$, $R^{41}$, $R^{42}$, any of the further substituents defined for the aromatic structure above.

More preferred Y substituents in the present invention may be selected from t-alkyl or t-alkyl,aryl such as -t-butyl or 2-phenylprop-2-yl, —$SiMe_3$, -phenyl, alkylphenyl-, phenylalkyl- or phosphinoalkyl—such as phosphinomethyl.

Preferably, when S is Si or C and one or more of $R^{40}$-$R^{42}$ are hydrogen, at least one of $R^{40}$-$R^{42}$ should be sufficiently bulky to give the required steric hindrance and such groups are preferably phosphorus, phosphinoalkyl-, a tertiary carbon bearing group such as -t-butyl, -aryl, -alkaryl, -aralkyl or tertiary silyl.

Preferably, the hydrocarbyl aromatic structure has, including substituents, from 5 up to 70 cyclic atoms, more preferably, 5 to 40 cyclic atoms, most preferably, 5-22 cyclic atoms, especially 5 or 6 cyclic atoms, if not a metallocene complex.

Preferably, the aromatic hydrocarbyl structure may be monocyclic or polycyclic. The cyclic aromatic atoms may be carbon or hetero, wherein references to hetero herein are references to sulphur, oxygen and/or nitrogen. However, it is preferred that the $Q^1$ and $Q^2$ atoms are linked to available adjacent cyclic carbon atoms of the at least one aromatic ring. Typically, when the cyclic hydrocarbyl structure is polycylic it is preferably bicyclic or tricyclic. The further cycles in the aromatic structure may or may not themselves be aromatic and aromatic structure should be understood accordingly. A non-aromatic cyclic ring(s) as defined herein may include unsaturated bonds. By cyclic atom is meant an atom which forms part of a cyclic skeleton.

Preferably, the bridging group —$R(Y^i)_n$, whether further substituted or otherwise preferably comprises less than 200 atoms, more preferably, less than 150 atoms, more preferably, less than 100 atoms.

By the term one further aromatic cyclic atom of the aromatic structure is meant any further aromatic cyclic atom in the aromatic structure which is not an available adjacent cyclic atom of the at least one aromatic ring to which the $Q^1$ or $Q^2$ atoms are linked, via the linking group.

Preferably, the immediately adjacent cyclic atoms on either side of the said available adjacent cyclic atoms are preferably not substituted. As an example, an aromatic phenyl ring joined to a $Q^1$ atom via position 1 on the ring and joined to a $Q^2$ atom via position 2 on the ring has preferably one or more said further aromatic cyclic atoms substituted at ring position 4 and/or 5 and the two immediately adjacent cyclic atoms to the said available adjacent cyclic atoms not substituted at positions 3 and 6. However, this is only a preferred substituent arrangement and substitution at ring positions 3 and 6, for example, is possible.

The term aromatic ring means that the at least one ring to which the $Q^2$ and $Q^2$ atom are linked via B & A respectively is aromatic, and aromatic should preferably be interpreted broadly to include not only a phenyl, cyclopentadienyl anion, pyrollyl, pyridinyl, type structures but other rings with aromaticity such as that found in any ring with delocalised Pi electrons able to move freely in the said ring.

Preferred aromatic rings have 5 or 6 atoms in the ring but rings with 4n+2 µl electrons are also possible such as [14] annulene, [18] annulene, etc The aromatic hydrocarbyl structure may be selected from 4 and/or 5 t-alkylbenzene-1,2-diyl, 4,5-diphenyl-benzene-1,2-diyl, 4 and/or 5-phenyl-benzene-1,2-diyl, 4,5-di-t-butyl-benzene-1,2-diyl, 4 or 5-t-butylbenzene-1,2-diyl, 2, 3, 4 and/or 5 t-alkyl-naphthalene-8,9-diyl, 1H-inden-5,6-diyl, 1, 2 and/or 3 methyl-1H-inden-5,6-diyl, 4,7 methano-1H-indene-1,2-diyl, 1, 2 and/or 3-dimethyl-1H-inden 5,6-diyls, 1,3-bis(trimethylsilyl)-isobenzofuran 5,6-diyl, 4-(trimethylsilyl) benzene-1,2 diyl, 4-phosphinomethyl benzene-1,2 diyl, 4-(2'-phenylprop-2'-yl)benzene-1,2 diyl, 4-dimethylsilylbenzene-1,2diyl, 4-di-t-butyl,methylsilyl benzene-1,2diyl, 4-(t-butyldimethylsilyl)-benzene-1,2diyl, 4-t-butylsilyl-benzene-1,2diyl, 4-(tri-t-butylsilyl)-benzene-1,2diyl, 4-(2'-tert-butylprop-2'-yl)benzene-1,2 diyl, 4-(2',2',3',4',4' pentamethyl-pent-3'-yl)-benzene-1,2diyl, 4-(2',2',4',4'-tetramethyl,3'-t-butyl-pent-3'-yl)-benzene-1,2 diyl, 4-(or 1')t-alkylferrocene-1,2-diyl, 4,5-diphenylferrocene-1,2-diyl, 4-(or 1')phenyl-ferrocene-1,2-diyl, 4,5-di-t-butyl-ferrocene-1,2-diyl, 4-(or 1')t-butylferrocene-1,2-diyl, 4-(or 1')(trimethylsilyl) ferrocene-1,2 diyl, 4-(or 1')phosphinomethyl ferrocene-1,2 diyl, 4-(or 1')(2'-phenylprop-2'-yl) ferrocene 1,2 diyl, 4-(or 1')dimethylsilylferrocene-1,2diyl, 4-(or 1')di-t-butyl,methylsilyl ferrocene-1,2diyl, 4-(or 1')(t-butyldimethylsilyl)-ferrocene-1,2diyl, 4-(or 1')t-butylsilyl-ferrocene-1,2diyl, 4-(or 1')(tri-t-butylsilyl)-ferrocene-1,2diyl, 4-(or 1') (2'-tert-butylprop-2'-yl)ferrocene-1,2 diyl, 4-(or 1')(2',2',3',4',4' pentamethyl-pent-3'-yl)-ferrocene-1,2diyl, 4-(or 1')(2',2',4',4'-tetramethyl,3'-t-butyl-pent-3'-yl)-ferrocene-1,2 diyl.

In the structures herein, where there is more than one stereisomeric form possible, all such stereoisomers are intended.

As mentioned above, in some embodiments, there may be two or more of said Y and/or non-Y substituents on further aromatic cyclic atoms of the aromatic structure. Optionally, the said two or more substituents may, especially when themselves on neighbouring cyclic aromatic atoms, combine to form a further ring structure such as a cycloaliphatic ring structure.

Such cycloaliphatic ring structures may be saturated or unsaturated, bridged or unbridged, substituted with alkyl, Y groups as defined herein, aryl, arylene, alkaryl, aralkyl, arylenalkyl, alkenyl, alkynyl, het, hetero, halo, cyano, nitro, —OR$^{19}$, —OC(O)R$^{20}$, —C(O) R$^{21}$—C(O)OR$^{22}$, —N(R$^{23}$)R$^{24}$, —C(O)N(R$^{28}$)R$^{28}$, —SR$^{29}$, —C(O)SR$^{33}$, —C(S)N(R$^{27}$) R$^{28}$, —CF$_3$, —SiR$^{71}$R$^{72}$R$^{73}$, or phosphinoalkyl wherein, when present, at least one of R$^{40}$-R$^{42}$ is not hydrogen and wherein R$^{19}$-R$^{30}$ are as defined herein; and R$^{71}$-R$^{73}$ are defined as R$^{40}$-R$^{42}$ but are preferably C$_1$-C$_4$ alkyl or phenyl and/or be interrupted by one or more (preferably less than a total of 4) oxygen, nitrogen, sulphur, silicon atoms or by silano or dialkyl silicon groups or mixtures thereof.

Examples of such structures include piperidine, pyridine, morpholine, cyclohexane, cycloheptane, cyclooctane, cyclononane, furan, dioxane, alkyl substituted DIOP, 2-alkyl substituted 1,3 dioxane, cyclopentanone, cyclohexanone, cyclopentene, cyclohexene, cyclohexadiene, 1,4 dithiane, piperizine, pyrollidine, thiomorpholine, cyclohexenone, bicyclo[4.2.0]octane, bicyclo[4.3.0]nonane, adamantane, tetrahydropyran, dihydropyran, tetrahydrothiopyran, tetrahydrofuran-2-one, delta valerolactone, gamma-butyrolactone, glutaric anhydride, dihydroimidazole, triazacyclononane, triazacyclodecane, thiazolidine, hexahydro-1H-indene (5,6 diyl), octahydro-4,7 methano-indene (1,2 diyl) and tetrahydro-1H-indene (5,6 diyl) all of which may be unsubstituted or substituted as defined for aryl herein.

However, whether forming combined groups or otherwise, it is preferred that the immediate adjacent aromatic cyclic atoms, on either side of the said available adjacent cyclic atoms to which Q$^1$ and Q$^2$ are linked, via the said linking group, are unsubstituted and preferable substitution is elsewhere on the at least one aromatic ring or elsewhere in the aromatic structure when the aromatic structure comprises more than one aromatic ring and the preferred position of combined Y substituents should be understood accordingly.

Typically, the group X$^2$ represents CR$^1$(R$^2$) (R$^3$), X$^2$ represents CR$^4$ (R$^5$) (R$^6$), X$^3$ represents CR$^7$(R$^8$) (R$^9$) and X$^4$ represents CR$^{10}$ (R$^{11}$)(R$^{12}$) wherein R$^2$ to R$^{22}$ represent alkyl, aryl or het.

Particularly preferred is when the organic groups R$^1$-R$^3$, R$^4$-R$^6$, R$^7$-R$^9$ and/or R$^{10}$-R$^{12}$ or, alternatively, R$^4$-R$^6$ and/or R$^7$-R$^{12}$ when associated with their respective tertiary carbon atom(s) form composite groups which are at least as sterically hindering as t-butyl(s).

The steric groups may be cyclic, part-cyclic or acyclic. When cyclic or part cyclic, the group may be substituted or unsubstituted or saturated or unsaturated. The cyclic or part cyclic groups may preferably contain, including the tertiary carbon atom(s), from C$_4$-C$_{34}$, more preferably C$_8$-C$_{24}$, most preferably C$_{10}$-C$_{20}$ carbon atoms in the cyclic structure. The cyclic structure may be substituted by one or more substituents selected from halo, cyano, nitro, OR$^{19}$, OC(O)R$^{20}$, C(O)R$^{21}$, C(O)OR$^{22}$, NR$^{23}$R$^{24}$, C(O)NR$^{25}$R$^{26}$, SR$^{29}$, R$^{28}$, C(O)SR$^{30}$, C(S)NR$^{27}$R$^{28}$, aryl or Het, wherein R$^{19}$ to R$^{30}$ each independently represent hydrogen, aryl or alkyl, and/or be interrupted by one or more oxygen or sulphur atoms, or by silano or dialkylsilicon groups.

In particular, when cyclic, X$^1$, X$^2$, X$^3$ and/or X$^4$ may represent congressyl, norbornyl, 1-norbornadienyl or adamantyl, or X$^1$ and X$^2$ together with Q$^2$ to which they are attached form an optionally substituted 2-Q$^2$-tricyclo[3.3.1.1{3,7}]decyl group or derivative thereof, or X$^1$ and X$^2$ together with Q$^2$ to which they are attached form a ring system of formula 1a

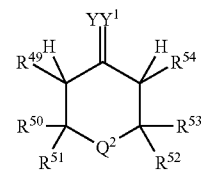

(1a)

Similarly, X$^3$ and X$^4$ together with Q$^1$ to which they are attached may form an optionally substituted 2-Q$^1$-tricyclo[3.3.1.1{3,7}]decyl group or derivative thereof, or X$^3$ and X$^4$ together with Q$^1$ to which they are attached may form a ring system of formula 1b

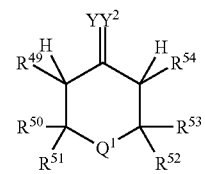

(1b)

Alternatively, one or more of the groups X$^1$, X$^2$, X$^3$ and/or X$^4$ may represent a solid phase to which the ligand is attached.

Particularly preferred is when X$^1$, X$^2$, X$^3$ and X$^4$ or X$^1$ and X$^2$ together with its respective Q$^2$ atom and X$^3$ and X$^4$ together with its respective Q$^1$ atom are the same or when X$^1$ and X$^3$ are the same whilst X$^2$ and X$^4$ are different but the same as each other.

In preferred embodiments, R$^1$ to R$^{12}$ each independently represent alkyl, aryl, or Het;
R$^{19}$ to R$^{33}$ each independently represent hydrogen, alkyl, aryl or Het;
R$^{49}$ and R$^{54}$, when present, each independently represent hydrogen, alkyl or aryl;
R$^{50}$ to R$^{53}$, when present, each independently represent alkyl, aryl or Het;
YY$^1$ and YY$^2$, when present, each independently represent oxygen, sulfur or N—R$^{55}$, wherein R$^{55}$ represents hydrogen, alkyl or aryl.

Preferably, R$^1$ to R$^{12}$ each independently represent alkyl or aryl. More preferably, R$^1$ to R$^{12}$ each independently represent C$_1$ to C$_6$ alkyl, C$_1$-C$_6$ alkyl phenyl (wherein the phenyl group is optionally substituted as aryl as defined herein) or phenyl (wherein the phenyl group is optionally substituted as aryl as defined herein). Even more preferably, R$^1$ to R$^{12}$ each independently represent C$_1$ to C$_6$ alkyl, which is optionally substituted as alkyl as defined herein. Most preferably, R$^1$ to R$^{12}$ each represent non-substituted C$_1$ to C$_6$ alkyl such as methyl, ethyl, n-propyl, iso-propyl, n-butyl, iso-butyl, tert-butyl, pentyl, hexyl and cyclohexyl, especially methyl.

In a particularly preferred embodiment of the present invention R$^1$, R$^4$, R$^7$ and R$^{10}$ each represent the same alkyl, aryl or Het moiety as defined herein, $R^2$, $R^5$, $R^8$ and $R^{11}$ each represent the same alkyl, aryl or Het moiety as defined herein, and $R^3$, $R^6$, $R^9$ and $R^{12}$ each represent the same alkyl, aryl or Het moiety as defined herein. More preferably $R^1$, $R^4$, $R^7$ and $R^{10}$ each represent the same $C_1$-$C_6$ alkyl, particularly non-substituted $C_1$-$C_6$ alkyl, such as methyl, ethyl, n-propyl, iso-propyl, n-butyl, iso-butyl, tert-butyl, pentyl, hexyl or cyclohexyl; $R^2$, $R^5$, $R^8$ and $R^{11}$ each independently represent the same $C_1$-$C_6$ alkyl as defined above; and $R^3$, $R^6$, $R^9$ and $R^{92}$ each independently represent the same $C_1$-$C_6$ alkyl as defined above. For example: $R^1$, $R^4$, $R^7$ and $R^{10}$ each represent methyl; $R^2$, $R^5$, $R^8$ and $R^{11}$ each represent ethyl; and, $R^3$, $R^6$, $R^9$ and $R^{12}$ each represent n-butyl or n-pentyl.

In an especially preferred embodiment of the present invention each $R^1$ to $R^{92}$ group represents the same alkyl, aryl, or Het moiety as defined herein. Preferably, when alkyl groups, each $R^1$ to $R^{92}$ represents the same $C_1$ to $C_6$ alkyl group, particularly non-substituted $C_1$-$C_6$ alkyl, such as methyl, ethyl, n-propyl, iso-propyl, n-butyl, iso-butyl, tert-butyl, pentyl, hexyl and cyclohexyl. More preferably, each $R^1$ to $R^{12}$ represents methyl or tert-butyl, most preferably, methyl.

The term "lower alkylene" which A and B represent in a compound of formula 1, when used herein, includes $C_0$-$C_{10}$ or $C_1$ to $C_{10}$ groups which, in the latter case, can be bonded at two places on the group to thereby connect the group $Q^1$ or $Q^2$ to the R group, and, in the latter case, is otherwise defined in the same way as "alkyl" below. Nevertheless, in the latter case, methylene is most preferred. In the former case, by $C_0$ is meant that the group $Q^1$ or $Q^2$ is connected directly to the R group and there is no $C_1$-$C_{10}$ lower alkylene group and in this case only one of A and B is a $C_1$-$C_{10}$ lower alkylene. In any case, when one of the groups A or B is $C_0$ then the other group cannot be $C_0$ and must be a $C_1$-$C_{10}$ group as defined herein and, therefore, at least one of A and B is a $C_1$-$C_{10}$ "lower alkylene" group.

The term "alkyl" when used herein, means $C_1$ to $C_{10}$ alkyl and includes methyl, ethyl, ethenyl, propyl, propenyl butyl, butenyl, pentyl, pentenyl, hexyl, hexenyl and heptyl groups. Unless otherwise specified, alkyl groups may, when there is a sufficient number of carbon atoms, be linear or branched (particularly preferred branched groups include t-butyl and isopropyl), be saturated or unsaturated, be cyclic, acyclic or part cyclic/acyclic, be unsubstituted, substituted or terminated by one or more substituents selected from halo, cyano, nitro, $OR^{19}$, $OC(O)R^{29}$, $C(O)R^{21}$, $C(O)OR^{22}$, $NR^{23}R^{24}$, $C(O)NR^{25}R^{26}$, $SR^{29}$, $C(O)SR^{90}$, $C(S)NR^{27}R^{28}$, unsubstituted or substituted aryl, or unsubstituted or substituted Het, wherein $R^{19}$ to $R^{20}$ each independently represent hydrogen, halo, unsubstituted or substituted aryl or unsubstituted or substituted alkyl, or, in the case of $R^{21}$, halo, nitro, cyano and amino and/or be interrupted by one or more (preferably less than 4) oxygen, sulphur, silicon atoms, or by silano or dialkylsilicon groups, or mixtures thereof.

The term "Ar" or "aryl" when used herein, includes five-to-ten-membered, preferably five to eight membered, carbocyclic aromatic or pseudo aromatic groups, such as phenyl, cyclopentadienyl and indenyl anions and naphthyl, which groups may be unsubstituted or substituted with one or more substituents selected from unsubstituted or substituted aryl, alkyl (which group may itself be unsubstituted or substituted or terminated as defined herein), Het (which group may itself be unsubstituted or substituted or terminated as defined herein), halo, cyano, nitro, $OR^{19}$, $OC(O)R^{20}$, $C(O)R^{21}$, $C(O)OR^{22}$, $NR^{23}R^{24}$, $C(O)NR^{26}R^{26}$, $SR^{29}$, $C(O)SR^{30}$ or $C(S)NR^{27}R^{28}$ wherein $R^{19}$ to $R^{30}$ each independently represent hydrogen, unsubstituted or substituted aryl or alkyl (which alkyl group may itself be unsubstituted or substituted or terminated as defined herein), or, in the case of $R^{21}$, halo, nitro, cyano or amino.

The term "alkenyl" when used herein, means $C_2$ to $C_{10}$ alkenyl and includes ethenyl, propenyl, butenyl, pentenyl, and hexenyl groups. Unless otherwise specified, alkenyl groups may, when there is a sufficient number of carbon atoms, be linear or branched, be saturated or unsaturated, be cyclic, acyclic or part cyclic/acyclic, be unsubstituted, substituted or terminated by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{26}R^{26}$, $SR^{29}$, $C(O)SR^{30}$, $C(S)NR^{27}R^{28}$, unsubstituted or substituted aryl, or unsubstituted or substituted Het, wherein $R^{19}$ to $R^{30}$ are defined as for alkyl above and/or be interrupted by one or more (preferably less than 4) oxygen, sulphur, silicon atoms, or by silano or dialkylsilicon groups, or mixtures thereof.

The term "alkynyl" when used herein, means $C_2$ to $C_{10}$ alkynyl and includes ethynyl, propynyl, butynyl, pentynyl, and hexynyl groups. Unless otherwise specified, alkynyl groups may, when there is a sufficient number of carbon atoms, be linear or branched, be saturated or unsaturated, be cyclic, acyclic or part cyclic/acyclic, be unsubstituted, substituted or terminated by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{26}R^{26}$, $SR^{29}$, $C(O)SR^{30}$, $C(S)NR^{27}R^{28}$, unsubstituted or substituted aryl, or unsubstituted or substituted Het, wherein $R^{19}$ to $R^{30}$ are defined as for alkyl above and/or be interrupted by one or more (preferably less than 4) oxygen, sulphur, silicon atoms, or by silano or dialkylsilicon groups, or mixtures thereof.

The terms "alkyl", "aralkyl", "alkaryl", "arylenealkyl" or the like should, in the absence of information to the contrary, be taken to be in accordance with the above definition of "alkyl" as far as the alkyl or alk portion of the group is concerned.

The above Ar or aryl groups may be attached by one or more covalent bonds but references to "arylene" or "arylenealkyl" or the like herein should be understood as two covalent bond attachment but otherwise be defined as Ar or aryl above as far as the arylene portion of the group is concerned. References to "alkaryl", "aralkyl" or the like should be taken as references to Ar or aryl above as far as the Ar or aryl portion of the group is concerned.

Halo groups with which the above-mentioned groups may be substituted or terminated include fluoro, chloro, bromo and iodo.

The term "Het", when used herein, includes four- to twelve-membered, preferably four- to ten-membered ring systems, which rings contain one or more heteroatoms selected from nitrogen, oxygen, sulfur and mixtures thereof, and which rings contain no, one or more double bonds or may be non-aromatic, partly aromatic or wholly aromatic in character. The ring systems may be monocyclic, bicyclic or fused. Each "Het" group identified herein may be unsubstituted or substituted by one or more substituents selected from halo, cyano, nitro, oxo, alkyl (which alkyl group may itself be unsubstituted or substituted or terminated as defined herein) —$OR^{19}$, —$OC(O)R^{20}$, —$C(O)R^{21}$, —$C(O)OR^{22}$, —$N(R^{23})R^{24}$,$C(O)N(R^{25})$ $R^{26}$, —$SR^{29}$, —$C(O)SR^{30}$ or —$C(S)N(R^{27})$ $R^{28}$ wherein $R^{19}$ to $R^{30}$ each independently represent hydrogen, unsubstituted or substituted aryl or alkyl (which alkyl group itself may be unsubstituted or substituted or terminated as defined herein) or, in the case of $R^{21}$, halo, nitro, amino or cyano. The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl. Substitution at Het may be at a carbon atom of the Het ring or, where appropriate, at one or more of the heteroatoms.

"Het" groups may also be in the form of an N oxide.

The term hetero as mentioned herein means nitrogen, oxygen, sulfur or mixtures thereof.

The adamantyl, congressyl, norbornyl or 1-norborndienyl group may optionally comprise, besides hydrogen atoms, one or more substituents selected from alkyl, $-OR^{19}$, $-OC(O)R^{29}$, halo, nitro, $-C(O)R^{21}$, $-C(O)OR^{22}$, cyano, aryl, $-N(R^{23})R^{24}$, $-C(O)N(R^{25})R^{26}$, $-C(S)(R^{27})\,R^{29}$, $-SR^{29}$, $-C(O)SR^{30}$—$P(R^{56})R^{57}$, $-PO(R^{58})\,(R^{59})$, $-PO_3H_2$, $-PO(OR^{60})(OR^{61})$, or $-SO_3R^{62}$, wherein $R^{19}$-$R^{30}$, alkyl, halo, cyano and aryl are as defined herein and $R^{56}$ to $R^{62}$ each independently represent hydrogen, alkyl, aryl or Het.

Suitably, when the adamantyl, congressyl, norbornyl or 1-norborndienyl group is substituted with one or more substituents as defined above, highly preferred substituents include unsubstituted $C_1$ to $C_8$ alkyl, $-OR^{19}$, $-OC(O)R^{29}$, phenyl, $-C(O)OR^{22}$, fluoro, $-SO_3H$, $-N(R^{23})R^{24}$, $-P(R^{56})_R^{57}$, $-C(O)N(R^{25})R^{26}$ and $-PO(R^{58})(R^{59})$, $-CF_3$, wherein $R^{19}$ represents hydrogen, unsubstituted $C_1$-$C_8$ alkyl or phenyl, $R^{20}$, $R^{22}$, $R^{23}$, $R^{24}$, $R^{25}$, $R^{26}$ each independently represent hydrogen or unsubstituted $C_1$-$C_8$ alkyl, $R^{56}$ to $R^{59}$ each independently represent unsubstituted $C_1$-$C_8$ alkyl or phenyl. In a particularly preferred embodiment the substituents are $C_1$ to $C_8$ alkyl, more preferably, methyl such as found in 1,3 dimethyl adamantyl.

Suitably, the adamantyl, congressyl, norbornyl or 1-norborndienyl group may comprise, besides hydrogen atoms, up to 10 substituents as defined above, preferably up to 5 substituents as defined above, more preferably up to 3 substituents as defined above. Suitably, when the adamantyl, congressyl, norbornyl or 1-norborndienyl group comprises, besides hydrogen atoms, one or more substituents as defined herein, preferably each substituent is identical. Preferred substituents are unsubstituted $C_1$-$C_8$ alkyl and trifluoromethyl, particularly unsubstituted $C_1$-$C_8$ alkyl such as methyl. A highly preferred adamantyl, congressyl, norbornyl or 1-norborndienyl group comprises hydrogen atoms only i.e. the adamantyl congressyl, norbornyl or 1-norborndienyl group is not substituted.

Preferably, when more than one adamantyl, congressyl, norbornyl or 1-norborndienyl group is present in a compound of formula 1, each such group is identical.

The 2-$Q^2$(or $Q^2$)-tricyclo[3.3.1.1.{3,7}]decyl group (referred to hereinafter as a 2-meta-adamantyl group for convenience wherein 2-meta-adamantyl is a reference to $Q^1$ or $Q^2$ being an arsenic, antimony or phosphorus atom i.e. 2-arsa-adamantyl and/or 2-stiba-adamantyl and/or 2-phospha-adamantyl, preferably, 2-phospha-adamantyl) may optionally comprise, beside hydrogen atoms, one or more substituents. Suitable substituents include those substituents as defined herein in respect of the adamantyl group. Highly preferred substituents include alkyl, particularly unsubstituted $C_1$-$C_8$ alkyl, especially methyl, trifluoromethyl, $-OR^{19}$ wherein $R^{29}$ is as defined herein particularly unsubstituted $C_1$-$C_8$ alkyl or aryl, and 4-dodecylphenyl. When the 2-meta-adamantyl group includes more than one substituent, preferably each substituent is identical.

Preferably, the 2-meta-adamantyl group is substituted on one or more of the 1, 3, 5 or 7 positions with a substituent as defined herein. More preferably, the 2-meta-adamantyl group is substituted on each of the 1, 3 and 5 positions. Suitably, such an arrangement means the Q atom of the 2-meta-adamantyl group is bonded to carbon atoms in the adamantyl skeleton having no hydrogen atoms. Most preferably, the 2-meta-adamantyl group is substituted on each of the 1, 3, 5 and 7 positions. When the 2-meta-adamantyl group includes more than 1 substituent preferably each substituent is identical. Especially preferred substituents are unsubstituted $C_1$-$C_8$ alkyl and haloakyls, particularly unsubstituted $C_1$-$C_8$ alkyl such as methyl and fluorinated $C_1$-$C_8$ alkyl such as trifluoromethyl.

Preferably, 2-meta-adamantyl represents unsubstituted 2-meta-adamantyl or 2-meta-adamantyl substituted with one or more unsubstituted $C_1$-$C_8$ alkyl substituents, or a combination thereof.

Preferably, the 2-meta-adamantyl group includes additional heteroatoms, other than the 2-Q atom, in the 2-meta-adamantyl skeleton. Suitable additional heteroatoms include oxygen and sulphur atoms, especially oxygen atoms. More preferably, the 2-meta-adamantyl group includes one or more additional heteroatoms in the 6, 9 and 10 positions. Even more preferably, the 2-meta-adamantyl group includes an additional heteroatom in each of the 6, 9 and 10 positions. Most preferably, when the 2-meta-adamantyl group includes two or more additional heteroatoms in the 2-meta-adamantyl skeleton, each of the additional heteroatoms are identical. Preferably, the 2-meta-adamantyl includes one or more oxygen atoms in the 2-meta-adamantyl skeleton. An especially preferred 2-meta-adamantyl group, which may optionally be substituted with one or more substituents as defined herein, includes an oxygen atom in each of the 6, 9 and 10 positions of the 2-meta-adamantyl skeleton.

Highly preferred 2-meta-adamantyl groups as defined herein include 2-phospha-1,3,5,7-tetramethyl-6,9,10-trioxadamantyl, 2-phospha-1,3,5-trimethyl-6,9,10-trioxadamantyl, 2-phospha-1,3,5,7-tetra(trifluoromethyl)-6,9,10-trioxadamantyl group, and 2-phospha-1,3,5-tri(trifluoromethyl)-6,9,10-trioxadamantyl group. Most preferably, the 2-phospha-adamantyl is selected from 2-phospha-1,3,5,7-tetramethyl-6,9,10-trioxadamantyl group or 2-phospha-1,3,5,-trimethyl-6,9,10-trioxadamantyl group.

Preferably, when more than one 2-meta-adamantyl group is present in a compound of formula 1, each 2-meta-adamantyl group is identical. However, it can also be advantageous if asymmetric ligands are prepared and if such ligands include a 2-meta-adamantyl group incorporating the $Q^1$ atom then other groups can be found on the $Q^2$ atom or vice versa.

The 2-meta-adamantyl group may be prepared by methods well known to those skilled in the art. Suitably, certain 2-phospha-adamantyl compounds are obtainable from Cytec Canada Inc, Canada. Likewise corresponding 2-meta-adamantyl compounds of formula I etc may be obtained from the same supplier or prepared by analogous methods.

Preferred embodiments of the present invention include those wherein:

$X^3$ represents $CR^7(R^8)\,(R^9)$, $X^4$ represents $CR^{10}(R^{11})(R^{12})$, $X^2$ represents $CR^1\,(Fe)\,(R^3)$ and $X^2$ represents $CR^4\,(R^5)(R^6)$;

$X^3$ represents $CR^7(R^8)\,(R^9)$, $X^4$ represents $CR^{10}(R^{11})(R^{12})$, and $X^1$ and $X^1$ together with $Q^2$ to which they are attached form a 2-phospha-adamantyl group;

$X^3$ represents $CR^7(R^8)\,(R^9)$, $X^4$ represents $CR^{10}\,(R^{11})(R^{12})$; and $X^1$ and $X^1$ together with $Q^2$ to which they are attached form a ring system of formula 1a;

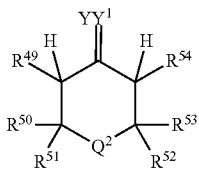
(1a)

$X^3$ represents $CR^7(R^8)$ $(R^9)$, $X^4$ represents adamantyl, and $X^1$ and $X^2$ together with $Q^2$ to which they are attached form a 2-phospha-adamantyl group;
$X^3$ represents $CR^7(R^8)$ $(R^9)$, $X^4$ represents adamantyl and $X^1$ and $X^2$ together with $Q^2$ to which they are attached form a ring system of formula 1a;

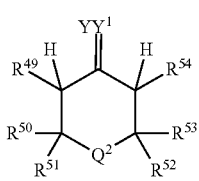
(1a)

$X^3$ represents $CR^7(R^8)$ $(R^9)$, $X^4$ represents adamantyl, $X^1$ represents $CR^1$ $(R^2)$ $(R^3)$ and $X^2$ represents $CR^4$ $(R^5)$ $(R^6)$;
$X^3$ represents $CR^7(R^8)$ $(R^9)$, $X^4$ represents congressyl, and $X^1$ and $X^2$ together with $Q^2$ to which they are attached form a 2-phospha-adamantyl group;
$X^3$ represents $CR^7(R^8)(R^9)$, $X^4$ represents congressyl, $X^1$ represents $CR^1$ $(R^2)$ $(R^3)$ and $X^2$ represents $CR^4$ $(R^5)$ $(R^6)$;
$X^3$ and $X^4$ independently represent adamantyl, and $X^2$ and $X^2$ together with $Q^2$ to which they are attached form a 2-phospha-adamantyl group;
$X^3$ and $X^4$ independently represent adamantyl, and $X^2$ and $X^2$ together with $Q^2$ to which they are attached form a ring system of formula 1a;

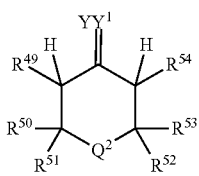
(1a)

$X^3$ and $X^4$ independently represent adamantyl, $X^1$ represents $CR^1$ $(R^2)$ $(R^3)$ and $X^2$ represents $CR^4$ $(R^5)$ $(R^6)$;
$X^2$, $X^2$, $X^3$ and $X^4$ represent adamantyl;
$X^3$ and $X^4$ together with $Q^2$ to which they are attached may form a ring system of formula 1b

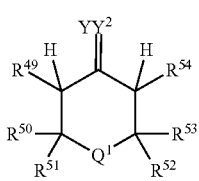
(1b)

and $X^2$ and $X^2$ together with $Q^2$ to which they are attached form a ring system of formula 1a;

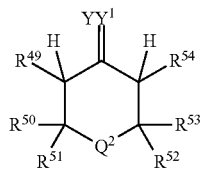
(1a)

$X^3$ and $X^4$ independently represent congressyl, and $X^1$ and $X^2$ together with $Q^2$ to which they are attached form a 2-phospha-adamantyl group;
$X^3$ and $X^4$ together with $Q^1$ to which they are attached may form a ring system of formula 1b

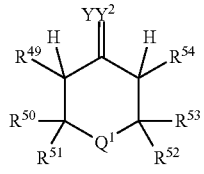
(1b)

and $X^1$ and $X^2$ together with $Q^2$, to which they are attached form a 2-phospha-adamantyl group;
$X^3$ and $X^4$ independently represent congressyl, and $X^1$ represents $CR^1$ $(R^2)$ $(R^3)$ and $X^2$ represents $CR^4$ $(R^5)$ $(R^6)$;
$X^3$ and $X^4$ together with $Q^1$ to which they are attached may form a ring system of formula 1b (1b)

$X^1$ represents $CR^1$ $(R^2)(R^3)$ and $X^2$ represents $CR^4(R^5)$ $(R^6)$;
$X^3$ and $X^4$ together with $Q^2$ to which they are attached form a 2-phospha-adamantyl group, and $X^2$ and $X^2$ together with $Q^2$ to which they are attached form a 2-phospha-adamantyl group Highly preferred embodiments of the present invention include those wherein:
$X^3$ represents $CR^2(R^8)$ $(R^9)$, $X^4$ represents $CR^{10}(R^{11})(R^{12})$, $X^1$ represents $CR^1(R^2)$ $(R^3)$ and $X^2$ represents $CR^4(R^5)$ $(R^6)$; especially where $R^1$-$R^{12}$ are methyl.

Preferably in a compound of formula 1, $X^3$ is identical to $X^4$ and/or $X^2$ is identical to $X^2$.

Particularly preferred combinations in the present invention include those wherein:—
(1) $X^3$ represents $CR^2(R^8)$ $(R^9)$, $X_4$ represents $CR^{10}$ $(R^{11})$ $(R^{12})$, $X^1$ represents $CR^1$ $(R^2)$ $(R^3)$ and $X^2$ represents $CR^4(R^5)$ $(R^6)$;
A and B are the same and represent —$CH_2$—;
$Q^2$ and $Q^2$ both represent phosphorus linked to the R group at ring positions 1 and 2;
R represents 4-(trimethylsilyl)-benzene-1,2-diyl
(2) $X^3$ represents $CR^2(R^8)$ $(R^9)$, $X^4$ represents $CR^{10}$ $(R^{11})$ $(R^{12})$, $X^1$ represents $CR^1$ $(R^2)$ $(R^3)$ and $X^2$ represents $CR^4(R^5)$ $(R^6)$;
A and B are the same and represent —$CH_2$—;

Q¹ and Q² both represent phosphorus linked to the R group at ring positions 1 and 2;
R represents 4-t-butyl-benzene-1,2-diyl.
(3) X³ and X⁴ together with Q¹ to which they are attached form a 2-phospha-adamantyl group, and, X¹ and X² together with Q² to which they are attached form a 2-phospha-adamantyl group;
A and B are the same and represent —CH₂—;
Q¹ and Q² both represent phosphorus linked to the R group at ring positions 1 and 2;
R represents 4-(trimethylsilyl)-benzene-1,2-diyl.
(4) X¹, X², X³ and X⁴ represent adamantyl;
A and B are the same and represent —CH₂—;
Q¹ and Q² both represent phosphorus linked to the R group at ring positions 1 and 2;
R represents 4-(trimethylsilyl)-benzene-1,2-diyl.

Preferably, in the compound of formula 1, A and B each independently represents $C_1$ to $C_6$ alkylene which is optionally substituted as defined herein, for example with alkyl groups. Preferably, the lower alkylene groups which A and B represent are non-substituted. Particularly preferred alkylene which A and B may independently represent are —CH₂— or —C₂H₄—. Most preferably, each of A and B represent the same alkylene as defined herein, particularly —CH₂—. Alternatively, one of A or B is $C_0$ ie Q² or Q¹ is connected directly to the group R and the other Q group is not connected directly to the group R and is a $C_1$ to $C_6$ alkylene, preferably —CH₂— or —C₂H₄—, most preferably, —CH₂.

Still further preferred compounds of formula I include those wherein:
R¹ to R¹² are alkyl and are the same and preferably, each represents $C_1$ to $C_6$ alkyl, particularly methyl.

Especially preferred specific compounds of formula I include those wherein:
each R¹ to R¹² is the same and represents methyl;
A and B are the same and represent —CH₂—;
R represents 4-t-butyl-benzene-1,2-diyl or 4(trimethylsilyl)-benzene-1,2-diyl.

Examples of suitable bidentate ligands are 1,2-bis(di-t-butylphosphinomethyl)-4,5-diphenyl benzene; 1,2-bis(di-t-butylphosphinomethyl)-4-phenylbenzene; 1,2-bis(di-t-butylphosphinomethyl)-4,5-bis-(trimethylsilyl)benzene; 1,2-bis(di-t-butylphosphinomethyl)-4-(trimethylsilyl)benzene; 1,2-bis(2-phosphinomethyl-1,3,5,7-tetramethyl-6,9,10-trioxa-adamantyl)-4,5-diphenylbenzene; 1,2-bis(2-phosphinomethyl-1,3,5,7-tetramethyl-6,9,10-trioxa-adamantyl)-4-phenylbenzene; 1,2-bis(2-phosphinomethyl-1,3,5,7-tetramethyl-6,9,10-trioxa-adamantyl)-4,5-bis-(trimethylsilyl)benzene; 1,2-bis(2-phosphinomethyl-1,3,5,7-tetramethyl-6,9,10-trioxa-adamantyl)-4-(trimethylsilyl)benzene; 1,2-bis(di-adamantylphosphinomethyl)-4,5 diphenylbenzene; 1,2-bis(di-adamantylphosphinomethyl)-4-phenyl benzene; 1,2-bis(di-adamantylphosphinomethyl)-4,5 bis-(trimethylsilyl)benzene; 1,2-bis(di-adamantylphosphinomethyl)-4-(trimethylsilyl)benzene; 1-(P,P adamantyl, t-butyl phosphinomethyl)-2-(di-t-butylphosphinomethyl)-4,5-diphenylbenzene; 1-(P,P adamantyl, t-butyl phosphinomethyl)-2-(di-t-butylphosphinomethyl)-4-phenylbenzene; 1-(P,P adamantyl, t-butyl phosphinomethyl)-2-(di-t-butylphosphinomethyl)-4,5-bis-(trimethylsilyl)benzene; 1-(P,P adamantyl, t-butyl phosphinomethyl)-2-(di-t-butylphosphinomethyl)-4-(trimethylsilyl)benzene; 1-(2-phosphinomethyl-1,3,5,7-tetramethyl-6,9,10-trioxa-adamantyl)-1-(di-t-butylphosphinomethyl)-4,5-diphenylbenzene; 1-(2-phosphinomethyl-1,3,5,7-tetramethyl-6,9,10-trioxa-adamantyl)-2-(di-t-butylphosphinomethyl)-4-phenyl benzene; 1-(2-phosphinomethyl-1,3,5,7-tetramethyl-6,9,10-trioxa-adamantyl)-(di-t-butylphosphinomethyl)-4,5-bis-(trimethylsilyl)benzene; 1-(2-phosphinomethyl-1,3,5,7-tetramethyl-6,9,10-trioxa-adamantyl) 2 (di-t-butylphosphinomethyl)-4-(trimethylsilyl)benzene; 1-(2-phosphinomethyl-1,3,5,7-tetramethyl-6,9,10-trioxa-adamantyl)-2-(diadamantylphosphinomethyl)-4,5-diphenyl benzene; 1-(2-phosphinomethyl-1,3,5,7-tetramethyl-6,9,10-trioxa-adamantyl)-2-(diadamantylphosphinomethyl)-4-phenyl benzene; 1-(2-phosphinomethyl-1,3,5,7-tetramethyl-6,9,10-trioxa-adamantyl)-2-(diadamantylphosphinomethyl)-4,5-bis-(trimethylsilyl)benzene; 1-(2-phosphinomethyl-1,3,5,7-tetramethyl-6,9,10-trioxa-adamantyl)-2-(diadamantylphosphinomethyl)-4-(trimethylsilyl)benzene; 1-(di-t-butylphosphinomethyl)-2-(diadamantylphosphinomethyl)-4,5-diphenyl benzene; 1-(di-t-butylphosphinomethyl)-2-(diadamantylphosphinomethyl)-4-phenyl benzene; 1-(di-t-butylphosphinomethyl)-2-(diadamantylphosphinomethyl)-4,5-bis-(trimethylsilyl)benzene; 1-(di-t-butylphosphinomethyl)-2-(diadamantylphosphinomethyl)-4-(trimethylsilyl)benzene; 1,2-bis(2-phosphinomethyl-1,3,5-trimethyl-6,9,10-trioxatricyclo-{3.3.1.1[3.7]}decyl)-4,5-diphenyl benzene; 1,2-bis(2-phosphinomethyl-1,3,5-trimethyl-6,9,10-trioxatricyclo-{3.3.1.1[3.7]}decyl)-4-phenyl benzene; 1,2-bis(2-phosphinomethyl-1,3,5-trimethyl-6,9,10-trioxatricyclo-{3.3.1.1[3.7]}decyl)-4,5-bis-(trimethylsilyl)benzene; 1,2-bis(2-phosphinomethyl-1,3,5-trimethyl-6,9,10-trioxatricyclo-{3.3.1.1[3.7]}decyl)-4-(trimethylsilyl)benzene; 1-(2-phosphinomethyl-1,3,5-trimethyl-6,9,10-trioxatricyclo-{3.3.1.1[3.7]}decyl)-2-(di-t-butylphosphinomethyl)-4,5-diphenyl benzene; 1-(2-phosphinomethyl-1,3,5-trimethyl-6,9,10-trioxatricyclo-{3.3.1.1[3.7]}decyl)-2-(di-t-butylphosphinomethyl)-4-phenyl benzene; 1-(2-phosphinomethyl-1,3,5-trimethyl-6,9,10-trioxatricyclo-{3.3.1.1[3.7]}decyl)-2-(di-t-butylphosphinomethyl)-4,5-bis-(trimethylsilyl)benzene; 1-(2-phosphinomethyl-1,3,5-trimethyl-6,9,10-trioxatricyclo-{3.3.1.1[3.7]}decyl)-2-(di-t-butylphosphinomethyl)-4-(trimethylsilyl)benzene; 1-(2-phosphinomethyl-1,3,5-trimethyl-6,9,10-trioxatricyclo-{3.3.1.1[3.7]}decyl)-2-(diadamantylphosphinomethyl)-4,5-diphenyl benzene; 1-(2-phosphinomethyl-1,3,5-trimethyl-6,9,10-trioxatricyclo-{3.3.1.1[3.7]}decyl)-2-(diadamantylphosphinomethyl)-4-phenyl benzene; 1-(2-phosphinomethyl-1,3,5-trimethyl-6,9,10-trioxatricyclo-{3.3.1.1[3.7]}decyl)-2-(diadamantylphosphinomethyl)-4,5-bis-(trimethylsilyl)benzene; 1-(2-phosphinomethyl-1,3,5-trimethyl-6,9,10-trioxatricyclo-{3.3.1.1[3.7]}decyl)-2-(diadamantylphosphinomethyl)-4-(trimethylsilyl)benzene; 1,2-bis-perfluoro(2-phosphinomethyl-1,3,5,7-tetramethyl-6,9,10-trioxatricyclo{3.3.1.1[3.7]}-decyl)-4,5-diphenyl benzene; 1,2-bis-perfluoro(2-phosphinomethyl-1,3,5,7-tetramethyl-6,9,10-trioxatricyclo{3.3.1.1[3.7]}decyl)-4-phenyl benzene; 1,2-bis-perfluoro(2-phosphinomethyl-1,3,5,7-tetramethyl-6,9,10-trioxatricyclo{3.3.1.1[3.7]}-decyl)-4,5-bis-(trimethylsilyl)benzene; 1,2-bis-perfluoro(2-phosphinomethyl-1,3,5,7-tetramethyl-6,9,10-trioxatricyclo{3.3.1.1[3.7]}decyl)-4-(trimethylsilyl)benzene; 1,2-bis-(2-phosphinomethyl-1,3,5,7-tetra(trifluoro-methyl)-6,9,10-trioxatricyclo{3.3.1.1[3.7]}decyl)-4,5-diphenyl benzene; 1,2-bis-(2-phosphinomethyl-1,3,5,7-tetra(trifluoro-methyl)-6,9,10-trioxatricyclo{3.3.1.1[3.7]}decyl)-4-phenyl benzene; 1,2-bis-(2-phosphinomethyl-1,3,5,7-tetra(trifluoro-methyl)-6,9,10-trioxatricyclo{3.3.1.1[3.7]}decyl)-4,5-bis-(trimethylsilyl)benzene; 1,2-bis-(2-phosphinomethyl-1,3,5,7-tetra (trifluoro-methyl)-6,9,10-trioxatricyclo{3.3.1.1[3.7]}decyl)-4-(trimethylsilyl)benzene; 1,2-bis(di-t-butylphosphinomethyl)-4,5-di-(2'-phenylprop-2'-yl)

benzene; 1,2-bis(di-t-butylphosphinomethyl)-4-(2'-phenylprop-2'-yl)benzene; 1,2-bis(di-t-butylphosphinomethyl)-4,5-di-t-butyl benzene; 1,2-bis(di-t-butylphosphinomethyl)-4-t-butylbenzene; 1,2-bis(2-phosphinomethyl-1,3,5,7-tetramethyl-6,9,10-trioxa-adamantyl)-4,5-di-(2'-phenylprop-2'-yl)benzene; 1,2-bis(2-phosphinomethyl-1,3,5,7-tetramethyl-6,9,10-trioxa-adamantyl)-4-(2'-phenylprop-2'-yl)benzene; 1,2-bis(2-phosphinomethyl-1,3,5,7-tetramethyl-6,9,10-trioxa-adamantyl)-4,5-(di-t-butyl)benzene; 1,2-bis(2-phosphinomethyl-1,3,5,7-tetramethyl-6,9,10-trioxa-adamantyl)-4-t-butylbenzene; 1,2-bis(di-adamantylphosphinomethyl)-4,5-di-(2'-phenylprop-2'-yl) benzene; 1,2-bis(di-adamantylphosphinomethyl)-4-(2'-phenylprop-2'-yl) benzene; 1,2-bis(di-adamantylphosphinomethyl)-4,5-(di-t-butyl)benzene; 1,2-bis(di-adamantylphosphinomethyl)-4-t-butyl benzene; 1-(P,P adamantyl, t-butyl phosphinomethyl)-2-(di-t-butyl-phosphinomethyl)-4,5-di-(2'-phenylprop-2'-yl)benzene; 1-(P,P adamantyl, t-butyl phosphinomethyl)-2-(di-t-butyl-phosphinomethyl)-4-(2'-phenylprop-2'-yl)benzene; 1-(P,P adamantyl, t-butyl phosphinomethyl)-2-(di-t-butylphosphinomethyl)-4,5-(di-t-butyl)benzene; 1-(P,P adamantyl, t-butyl phosphinomethyl)-2-(di-t-butylphosphinomethyl)-4-t-butylbenzene; 1-(2-phosphinomethyl-1,3,5,7-tetramethyl-6,9,10-trioxa-adamantyl)-2-(di-t-butylphosphinomethyl)-4,5-di-(2'-phenylprop-2'-yl)benzene; 1-(2-phosphinomethyl-1,3,5,7-tetramethyl-6,9,10-trioxa-adamantyl)-2-(di-t-butylphosphinomethyl)-4-(2'-phenylprop-2'-yl)benzene; 1-(2-phosphinomethyl-1,3,5,7-tetramethyl-6,9,10-trioxa-adamantyl)-2-(di-t-butylphosphinomethyl)-4,5-(di-t-butyl)benzene; 1-(2-phosphinomethyl-1,3,5,7-tetramethyl-6,9,10-trioxa-adamantyl)-2-(di-t-butylphosphinomethyl)-4-t-butyl benzene; 1-(2-phosphinomethyl-1,3,5,7-tetramethyl-6,9,10-trioxa-adamantyl)-2-(diadamantylphosphinomethyl)-4,5-di-(2'-phenylprop-2'-yl) benzene; 1-(2-phosphinomethyl-1,3,5,7-tetramethyl-6,9,10-trioxa-adamantyl)-2-(diadamantylphosphinomethyl)-4-(2'-phenylprop-2'-yl) benzene; 1-(2-phosphinomethyl-1,3,5,7-tetramethyl-6,9,10-trioxa-adamantyl)-2-(diadamantylphosphinomethyl)-4,5-(di-t-butyl)benzene; 1-(2-phosphinomethyl-1,3,5,7-tetramethyl-6,9,10-trioxa-adamantyl)-2-(diadamantylphosphinomethyl)-4-t-butyl benzene; 1-(di-t-butylphosphinomethyl)-2-(diadamantylphosphinomethyl)-4,5-di-(2'-phenylprop-2'-yl)benzene; 1-(di-t-butylphosphinomethyl)-2-(diadamantylphosphinomethyl)-4-(2'-phenylprop-2'-yl)benzene; 1-(di-t-butylphosphinomethyl)-2-(diadamantylphosphinomethyl)-4,5-(di-t-butyl)benzene; 1-(di-t-butylphosphinomethyl)-2-(diadamantylphosphinomethyl)-4-t-butyl benzene; 1,2-bis(2-phosphinomethyl-1,3,5-trimethyl-6,9,10-trioxatricyclo-{3.3.1.1[3.7]}decyl)-4,5-di-(2'-phenylprop-2'-yl) benzene; 1,2-bis(2-phosphinomethyl-1,3,5-trimethyl-6,9,10-trioxatricyclo-{3.3.1.1[3.7]}decyl)-4-(2'-phenylprop-2'-yl) benzene; 1,2-bis(2-phosphinomethyl-1,3,5-trimethyl-6,9,10-trioxatricyclo-{3.3.1.1[3.7]}decyl)-4,5-(di-t-butyl)benzene; 1,2-bis(2-phosphinomethyl-1,3,5-trimethyl-6,9,10-trioxatricyclo-{3.3.1.1[3.7]}decyl)-4-t-butyl benzene; 1-(2-phosphinomethyl-1,3,5-trimethyl-6,9,10-trioxatricyclo-{3.3.1.1[3.7]}decyl)-2-(di-t-butylphosphinomethyl)-4,5-di-(2'-phenylprop-2'-yl)benzene; 1-(2-phosphinomethyl-1,3,5-trimethyl-6,9,10-trioxatricyclo-{3.3.1.1[3.7]}decyl)-2-(di-t-butylphosphinomethyl)-4-(2'-phenylprop-2'-yl) benzene; 1-(2-phosphinomethyl-1,3,5-trimethyl-6,9,10-trioxatricyclo-{3.3.1.1[3.7]}decyl)-2-(di-t-butylphosphinomethyl)-4,5-(di-t-butyl)benzene; 1-(2-phosphinomethyl-1,3,5-trimethyl-6,9,10-trioxatricyclo-{3.3.1.1[3.7]}decyl)-2-(di-t-butylphosphinomethyl)-4-t-butyl benzene; 1-(2-phosphinomethyl-1,3,5-trimethyl-6,9,10-trioxatricyclo-{3.3.1.1[3.7]}decyl)-2-(diadamantylphosphinomethyl)-4,5-di-(2'-phenylprop-2'-yl) benzene; 1-(2-phosphinomethyl-1,3,5-trimethyl-6,9,10-trioxatricyclo-{3.3.1.1[3.7]}decyl)-2-(diadamantylphosphinomethyl)-4-(2'-phenylprop-2'-yl) benzene; 1-(2-phosphinomethyl-1,3,5-trimethyl-6,9,10-trioxatricyclo-{3.3.1.1[3.7]}decyl)-2-(diadamantylphosphinomethyl)-4,5-(di-t-butyl)benzene; 1-(2-phosphinomethyl-1,3,5-trimethyl-6,9,10-trioxatricyclo-{3.3.1.1[3.7]}decyl)-2-(diadamantylphosphinomethyl)-4-t-butyl benzene; 1,2-bis-perfluoro(2-phosphinomethyl-1,3,5,7-tetramethyl-6,9,10-trioxatricyclo{3.3.1.1[3.7]}-decyl)-4,5-di-(2'-phenylprop-2'-yl)benzene; 1,2-bis-perfluoro(2-phosphinomethyl-1,3,5,7-tetramethyl-6,9,10-trioxatricyclo{3.3.1.1[3.7]}decyl)-4-(2'-phenylprop-2'-yl)benzene; 1,2-bis-perfluoro(2-phosphinomethyl-1,3,5,7-tetramethyl-6,9,10-trioxatricyclo{3.3.1.1[3.7]}-decyl)-4,5-(di-t-butyl)benzene; 1,2-bis-perfluoro(2-phosphinomethyl-1,3,5,7-tetramethyl-6,9,10-trioxatricyclo{3.3.1.1[3.7]}decyl)-4-t-butyl benzene; 1,2-bis-(2-phosphinomethyl-1,3,5,7-tetra(trifluoro-methyl)-6,9,10-trioxatricyclo{3.3.1.1[3.7]}decyl)-4,5-di-(2'-phenylprop-2'-yl) benzene; 1,2-bis-(2-phosphinomethyl-1,3,5,7-tetra(trifluoro-methyl)-6,9,10-trioxatricyclo{3.3.1.1[3.7]}decyl)-4-(2'-phenylprop-2'-yl) benzene; 1,2-bis-(2-phosphinomethyl-1,3,5,7-tetra(trifluoro-methyl)-6,9,10-trioxatricyclo{3.3.1.1[3.7]}decyl)-4,5-(di-t-butyl)benzene; 1,2-bis-(2-phosphinomethyl-1,3,5,7-tetra(trifluoro-methyl)-6,9,10-trioxatricyclo{3.3.1.1[3.7]}decyl)-4-t-butyl benzene and 1-(8-phosphinomethyl-1,3,5,7-tetramethyl-2,4,6-trioxatricyclo{3.3.1.1[3.7]}decyl)-2-(di-t-butylphosphinomethyl)-5-(trimethylsilyl) benzene.

Examples of suitable bidentate ferrocene type ligands are 1,2-bis(di-t-butylphosphinomethyl)-4,5-diphenyl ferrocene; 1,2-bis(di-t-butylphosphinomethyl)-4-(or 1')phenylferrocene; 1,2-bis(di-t-butylphosphinomethyl)-4,5-bis-(trimethylsilyl) ferrocene; 1,2-bis(di-t-butylphosphinomethyl)-4-(or 1')(trimethylsilyl)ferrocene; 1,2-bis(2-phosphinomethyl-1,3,5,7-tetramethyl-6,9,10-trioxa-adamantyl)-4,5-diphenyl-ferrocene; 1,2-bis(2-phosphinomethyl-1,3,5,7-tetramethyl-6,9,10-trioxa-adamantyl) 4-(or 1')phenylferrocene; 1,2-bis(2-phosphinomethyl-1,3,5,7-tetramethyl-6,9,10-trioxa-adamantyl)-4,5-bis-(trimethylsilyl)ferrocene; 1,2-bis(2-phosphinomethyl-1,3,5,7-tetramethyl-6,9,10-trioxa-adamantyl) 4-(or 1')(trimethylsilyl)ferrocene; 1,2-bis(di-adamantylphosphinomethyl)-4,5 diphenylferrocene; 1,2-bis(di-adamantylphosphinomethyl)-4-(or 1')phenyl ferrocene; 1,2-bis(di-adamantylphosphinomethyl)-4,5 bis-(trimethylsilyl)ferrocene; 1,2-bis(di-adamantylphosphinomethyl)-4-(or 1')(trimethylsilyl) ferrocene; 1-(P,P adamantyl, t-butyl phosphinomethyl)-2-(di-t-butylphosphinomethyl)-4,5-diphenyl-ferrocene; 1-(P,P adamantyl, t-butyl phosphinomethyl)-2-(di-t-butylphosphinomethyl)-4-(or 1')phenylferrocene; 1-(P,P adamantyl, t-butyl phosphinomethyl)-2-(di-t-butyl-phosphinomethyl)-4,5-bis-(trimethylsilyl)ferrocene; 1-(P,P adamantyl, t-butyl phosphinomethyl)-2-(di-t-butylphosphinomethyl)-4-(or 1')(trimethylsilyl)ferrocene; 1-(2-phosphinomethyl-1,3,5,7-tetramethyl-6,9,10-trioxa-adamantyl)-2-(di-t-butylphosphinomethyl)-4,5-diphenylferrocene; 1-(2-phosphinomethyl-1,3,5,7-tetramethyl-6,9,10-trioxa-adamantyl)-2-(di-t-butylphosphinomethyl)-4-(or 1')phenyl ferrocene; 1-(2-phosphinomethyl-1,3,5,7-tetramethyl-6,9,10-trioxa-adamantyl)-2-(di-t-butylphosphinomethyl)-4,5-bis-(trimethylsilyl)ferrocene; 1-(2-phosphinomethyl-1,3,5,7-tetramethyl-6,9,10-trioxa-adamantyl) 2 (di-t-butylphosphinomethyl)-4-(or 1')(trimethylsilyl) ferrocene;

1-(2-phosphinomethyl-1,3,5,7-tetramethyl-6,9,10-trioxa-adamantyl)-2-(diadamantylphosphinomethyl)-4,5-diphenyl ferrocene; 1-(2-phosphinomethyl-1,3,5,7-tetramethyl-6,9,10-trioxa-adamantyl)-2-(diadamantylphosphinomethyl)-4-(or 1')phenyl ferrocene; 1-(2-phosphinomethyl-1,3,5,7-tetramethyl-6,9,10-trioxa-adamantyl)-2-(diadamantylphosphinomethyl)-4,5-bis-(trimethylsilyl) ferrocene; 1-(2-phosphinomethyl-1,3,5,7-tetramethyl-6,9,10-trioxa-adamantyl)-2-(diadamantylphosphinomethyl)-4-(or 1')(trimethylsilyl) ferrocene; 1-(di-t-butylphosphinomethyl)-2-(diadamantylphosphinomethyl)-4,5-diphenyl ferrocene; 1-(di-t-butylphosphinomethyl)-2-(diadamantylphosphinomethyl)-4-(or 1')phenyl ferrocene; 1-(di-t-butylphosphinomethyl)-2-(diadamantylphosphinomethyl)-4,5-bis-(trimethylsilyl) ferrocene; 1-(di-t-butylphosphinomethyl)-2-(diadamantylphosphinomethyl)-4-(or 1')(trimethylsilyl) ferrocene; 1,2-bis(2-phosphinomethyl-1,3,5-trimethyl-6,9,10-trioxatricyclo-{3.3.1.1[3.7]}decyl)-4,5-diphenyl ferrocene; 1,2-bis(2-phosphinomethyl-1,3,5-trimethyl-6,9,10-trioxatricyclo-{3.3.1.1[3.7]}decyl)-4-(or 1')phenyl ferrocene; 1,2-bis(2-phosphinomethyl-1,3,5-trimethyl-6,9,10-trioxatricyclo-{3.3.1.1[3.7]}decyl)-4,5-bis-(trimethylsilyl) ferrocene; 1,2-bis(2-phosphinomethyl-1,3,5-trimethyl-6,9,10-trioxatricyclo-{3.3.1.1[3.7]}decyl)-4-(or 1')(trimethylsilyl) ferrocene; 1-(2-phosphinomethyl-1,3,5-trimethyl-6,9,10-trioxatricyclo-{3.3.1.1[3.7]}decyl)-2-(di-t-butylphosphinomethyl)-4,5-diphenyl ferrocene; 1-(2-phosphinomethyl-1,3,5-trimethyl-6,9,10-trioxatricyclo-{3.3.1.1[3.7]}decyl)-2-(di-t-butylphosphinomethyl)-4-(or 1')phenyl ferrocene; 1-(2-phosphinomethyl-1,3,5-trimethyl-6,9,10-trioxatricyclo-{3.3.1.1[3.7]}decyl)-2-(di-t-butylphosphinomethyl)-4,5-bis-(trimethylsilyl) ferrocene; 1-(2-phosphinomethyl-1,3,5-trimethyl-6,9,10-trioxatricyclo-{3.3.1.1[3.7]}decyl)-2-(di-t-butylphosphinomethyl)-4-(or 1')(trimethylsilyl) ferrocene; 1-(2-phosphinomethyl-1,3,5-trimethyl-6,9,10-trioxatricyclo-{3.3.1.1[3.7]}decyl)-2-(diadamantylphosphinomethyl)-4,5-diphenyl ferrocene; 1-(2-phosphinomethyl-1,3,5-trimethyl-6,9,10-trioxatricyclo-{3.3.1.1[3.7]}decyl)-2-(diadamantylphosphinomethyl)-4-(or 1')phenyl ferrocene; 1-(2-phosphinomethyl-1,3,5-trimethyl-6,9,10-trioxatricyclo-{3.3.1.1[3.7]}decyl)-2-(diadamantylphosphinomethyl)-4,5-bis-(trimethylsilyl) ferrocene; 1-(2-phosphinomethyl-1,3,5-trimethyl-6,9,10-trioxatricyclo-{3.3.1.1[3.7]}decyl)-2-(diadamantylphosphinomethyl)-4-(or 1')(trimethylsilyl) ferrocene; 1,2-bis-perfluoro(2-phosphinomethyl-1,3,5,7-tetramethyl-6,9,10-trioxatricyclo{3.3.1.1[3.7]}-decyl)-4,5-diphenyl ferrocene; 1,2-bis-perfluoro(2-phosphinomethyl-1,3,5,7-tetramethyl-6,9,10-trioxatricyclo{3.3.1.1[3.7]}decyl)-4-(or 1')phenyl ferrocene; 1,2-bis-perfluoro(2-phosphinomethyl-1,3,5,7-tetramethyl-6,9,10-trioxatricyclo{3.3.1.1[3.7]}-decyl)-4,5-bis-(trimethylsilyl) ferrocene; 1,2-bis-perfluoro(2-phosphinomethyl-1,3,5,7-tetramethyl-6,9,10-trioxatricyclo{3.3.1.1[3.7]}decyl)-4-(or 1')(trimethylsilyl) ferrocene; 1,2-bis-(2-phosphinomethyl-1,3,5,7-tetra(trifluoro-methyl)-6,9,10-trioxatricyclo{3.3.1.1[3.7]}decyl)-4,5-diphenyl ferrocene; 1,2-bis-(2-phosphinomethyl-1,3,5,7-tetra(trifluoro-methyl)-6,9,10-trioxatricyclo{3.3.1.1[3.7]}decyl)-4-(or 1')phenyl ferrocene; 1,2-bis-(2-phosphinomethyl-1,3,5,7-tetra(trifluoro-methyl)-6,9,10-trioxatricyclo{3.3.1.1[3.7]}decyl)-4,5-bis-(trimethylsilyl) ferrocene; 1,2-bis-(2-phosphinomethyl-1,3,5,7-tetra(trifluoro-methyl)-6,9,10-trioxatricyclo{3.3.1.1[3.7]}decyl)-4-(or 1')(trimethylsilyl) ferrocene; 1,2-bis(di-t-butylphosphinomethyl)-4,5-di-(2'-phenylprop-2'-yl)ferrocene; 1,2-bis(di-t-butylphosphinomethyl)-4-(or 1')(2'-phenylprop-2'-yl)ferrocene; 1,2-bis(di-t-butylphosphinomethyl)-4,5-di-t-butyl ferrocene; 1,2-bis(di-t-butylphosphinomethyl)-4-(or 1')t-butylferrocene; 1,2-bis(2-phosphinomethyl-1,3,5,7-tetramethyl-6,9,10-trioxa-adamantyl)-4,5-di-(2'-phenylprop-2'-yl)ferrocene; 1,2-bis(2-phosphinomethyl-1,3,5,7-tetramethyl-6,9,10-trioxa-adamantyl)-4-(or 1')(2'-phenylprop-2'-yl)ferrocene; 1,2-bis(2-phosphinomethyl-1,3,5,7-tetramethyl-6,9,10-trioxa-adamantyl)-4,5-(di-t-butyl)ferrocene; 1,2-bis(2-phosphinomethyl-1,3,5,7-tetramethyl-6,9,10-trioxa-adamantyl)-4-(or 1')t-butylferrocene; 1,2-bis(di-adamantylphosphinomethyl)-4,5-di-(2'-phenylprop-2'-yl) ferrocene; 1,2-bis(di-adamantylphosphinomethyl)-4-(or 1')(2'-phenylprop-2'-yl) ferrocene; 1,2-bis(di-adamantylphosphinomethyl)-4,5-(di-t-butyl) ferrocene; 1,2-bis(di-adamantylphosphinomethyl)-4-(or 1')t-butyl ferrocene; 1-(P,P adamantyl, t-butyl phosphinomethyl)-2-(di-t-butylphosphinomethyl)-4,5-di-(2'-phenylprop-2'-yl)ferrocene; 1-(P,P adamantyl, t-butyl phosphinomethyl)-2-(di-t-butylphosphinomethyl)-4-(or 1')(2'-phenylprop-2'-yl)ferrocene; 1-(P,P adamantyl, t-butyl phosphinomethyl)-2-(di-t-butylphosphinomethyl)-4,5-(di-t-butyl)ferrocene; 1-(P,P adamantyl, t-butyl phosphinomethyl)-2-(di-t-butylphosphinomethyl)-4-(or 1')t-butylferrocene; 1-(2-phosphinomethyl-1,3,5,7-tetramethyl-6,9,10-trioxa-adamantyl)-2-(di-t-butylphosphinomethyl)-4,5-di-(2'-phenylprop-2'-yl)ferrocene; 1-(2-phosphinomethyl-1,3,5,7-tetramethyl-6,9,10-trioxa-adamantyl)-2-(di-t-butylphosphinomethyl)-4-(or 1')(2'-phenylprop-2'-yl) ferrocene; 1-(2-phosphinomethyl-1,3,5,7-tetramethyl-6,9,10-trioxa-adamantyl)-2-(di-t-butylphosphinomethyl)-4,5-(di-t-butyl)ferrocene; 1-(2-phosphinomethyl-1,3,5,7-tetramethyl-6,9,10-trioxa-adamantyl)-2-(di-t-butylphosphinomethyl)-4-(or 1')t-butyl ferrocene; 1-(2-phosphinomethyl-1,3,5,7-tetramethyl-6,9,10-trioxa-adamantyl)-2-(diadamantylphosphinomethyl)-4,5-di-(2'-phenylprop-2'-yl) ferrocene; 1-(2-phosphinomethyl-1,3,5,7-tetramethyl-6,9,10-trioxa-adamantyl)-2-(diadamantylphosphinomethyl)-4-(or 1')(2'-phenylprop-2'-yl) ferrocene; 1-(2-phosphinomethyl-1,3,5,7-tetramethyl-6,9,10-trioxa-adamantyl)-2-(diadamantylphosphinomethyl)-4,5-(di-t-butyl) ferrocene; 1-(2-phosphinomethyl-1,3,5,7-tetramethyl-6,9,10-trioxa-adamantyl)-2-(diadamantylphosphinomethyl)-4-(or 1')t-butyl ferrocene; 1-(di-t-butylphosphinomethyl)-2-(diadamantylphosphinomethyl)-4,5-di-(2'-phenylprop-2'-yl) ferrocene; 1-(di-t-butylphosphinomethyl)-2-(diadamantylphosphinomethyl)-4-(or 1')(2'-phenylprop-2'-yl) ferrocene; 1-(di-t-butylphosphinomethyl)-2-(diadamantylphosphinomethyl)-4,5-(di-t-butyl) ferrocene; 1-(di-t-butylphosphinomethyl)-2-(diadamantylphosphinomethyl)-4-(or 1')t-butyl ferrocene; 1,2-bis(2-phosphinomethyl-1,3,5-trimethyl-6,9,10-trioxatricyclo-{3.3.1.1[3.7]}decyl)-4,5-di-(2'-phenylprop-2'-yl) ferrocene; 1,2-bis(2-phosphinomethyl-1,3,5-trimethyl-6,9,10-trioxatricyclo-{3.3.1.1[3.7]}decyl)-4-(or 1')(2'-phenylprop-2'-yl) ferrocene; 1,2-bis(2-phosphinomethyl-1,3,5-trimethyl-6,9,10-trioxatricyclo-{3.3.1.1[3.7]}decyl)-4,5-(di-t-butyl) ferrocene; 1,2-bis(2-phosphinomethyl-1,3,5-trimethyl-6,9,10-trioxatricyclo-{3.3.1.1[3.7]}decyl)-4-(or 1')t-butyl ferrocene; 1-(2-phosphinomethyl-1,3,5-trimethyl-6,9,10-trioxatricyclo-{3.3.1.1[3.7]}decyl)-2-(di-t-butylphosphinomethyl)-4,5-di-(2'-phenylprop-2'-yl) ferrocene; 1-(2-phosphinomethyl-1,3,5-trimethyl-6,9,10-trioxatricyclo-{3.3.1.1[3.7]}decyl)-2-(di-t-butylphosphinomethyl)-4-(or 1')(2'-phenylprop-2'-yl) ferrocene; 1-(2-phosphinomethyl-1,3,5-trimethyl-6,9,10-trioxatricyclo-{3.3.1.1[3.7]}decyl)-2-(di-t-butylphosphinomethyl)-4,5-(di-t-butyl) ferrocene; 1-(2-phosphinomethyl-1,3,5-trimethyl-6,9,10-trioxatricyclo-{3.3.1.1[3.7]}decyl)-2-(di-t-butylphosphinomethyl)-4-(or 1')t-butyl ferrocene; 1-(2-phosphinomethyl-1,3,5-trimethyl-6,9,10-trioxatricyclo-{3.3.1.1[3.7]}decyl)-2-(diadamantylphosphinomethyl)-4,5-di-(2'-phenylprop-2'-yl) ferrocene; 1-(2-phosphinomethyl-1,3,5-trimethyl-6,9,10-trioxatricyclo-{3.3.1.1[3.7]}decyl)-2-(diadamantylphosphinomethyl)-4-(or 1')(2'-phenylprop-2'-yl) ferrocene; 1-(2-phosphinomethyl-1,3,5-trimethyl-6,9,10-trioxatricyclo-{3.3.1.1[3.7]}decyl)-2-(diadamantylphosphinomethyl)-4,5-(di-t-butyl) ferrocene; 1-(2-phosphinomethyl-1,3,5-trimethyl-6,9,10-trioxatricyclo-{3.3.1.1[3.7]}decyl)-2-(diadamantylphosphinomethyl)-4-(or 1')$_t$-butyl ferrocene; 1,2-bis-perfluoro(2-phosphinomethyl-1,3,5,7-tetramethyl-6,9,10-trioxatricyclo{3.3.1.1[3.7]}-decyl)-4,5-di-(2'-phenylprop-2'-yl) ferrocene; 1,2-bis-perfluoro(2-phosphinomethyl-1,3,5,7-tetramethyl-6,9,10-trioxatricyclo{3.3.1.1[3.7]}decyl)-4-(or 1')(2'-phenylprop-2'-yl) ferrocene; 1,2-bis-perfluoro(2-phosphinomethyl-1,3,5,7-tetramethyl-6,9,10-trioxatricyclo{3.3.1.1[3.7]}-decyl)-4,5-(di-t-butyl) ferrocene; 1,2-bis-perfluoro(2-phosphinomethyl-1,3,5,7-tetramethyl-6,9,10-trioxatricyclo{3.3.1.1[3.7]}decyl)-4-(or 1')t-butyl ferrocene; 1,2-bis-(2-phosphinomethyl-1,3,5,7-tetra(trifluoro-methyl)-6,9,10-trioxatricyclo{3.3.1.1[3.7]}decyl)-4,5-di-(2'-phenylprop-2'-yl) ferrocene; 1,2-bis-(2-phosphinomethyl-1,3,5,7-tetra(trifluoro-methyl)-6,9,10-trioxatricyclo{3.3.1.1[3.7]}decyl)-4-(or 1')(2'-phenylprop-2'-yl) ferrocene; 1,2-bis-(2-phosphinomethyl-1,3,5,7-tetra(trifluoro-methyl)-6,9,10-trioxatricyclo{3.3.1.1[3.7]}decyl)-4,5-(di-t-butyl) ferrocene; 1,2-bis-(2-phosphinomethyl-1,3,5,7-tetra(trifluoro-methyl)-6,9,10-trioxatricyclo{3.3.1.1[3.7]}decyl)-4-(or 1')t-butyl ferrocene.

The invention also extends to a modification of all the above examples of suitable bidentate ligands and suitable bidentate ferrocene type ligands wherein one of the methylene linking groups attached to the aromatic ring is removed so that the respective phosphorus atom is attached directly to the ring representing R. In these modified examples, when one methylene has been removed, the other methylene group linking the other phosphorus atom is still present so that a $C_3$ bridge connects the two phosphorus atoms representing $Q^1$ and $Q^2$ in each example above.

Selected structures of ligands of the invention include:—

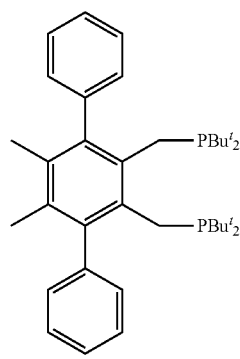

1,2-bis(di-tert-butylphosphinomethyl)-3,6-diphenyl-4,5-dimethyl benzene

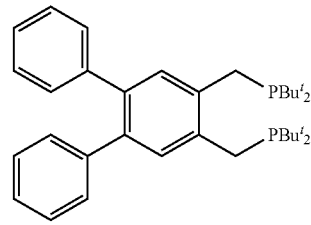

1,2bis(di-tert-butyl(phosphinomethyl)-4,5-diphenyl benzene

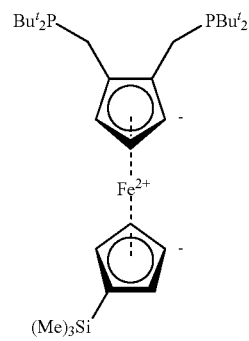

1,2-bis(di-tert-butylphospinomethyl)-1'-trimethylsilyl ferrocene

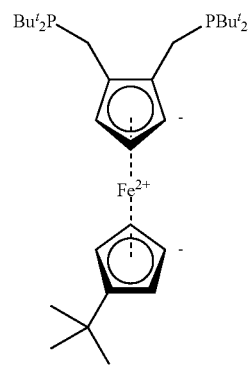

1,2-bis(di-tert-butylphospinomethyl)-1'-tert-butyl ferrocene

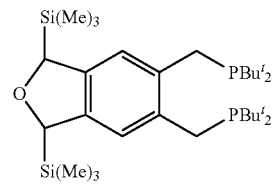

5,6-bis(di-tert-butylphosphinomethyl)-1,3-bis-trimethylsilyl-1,3-dihydroisobenzofuran

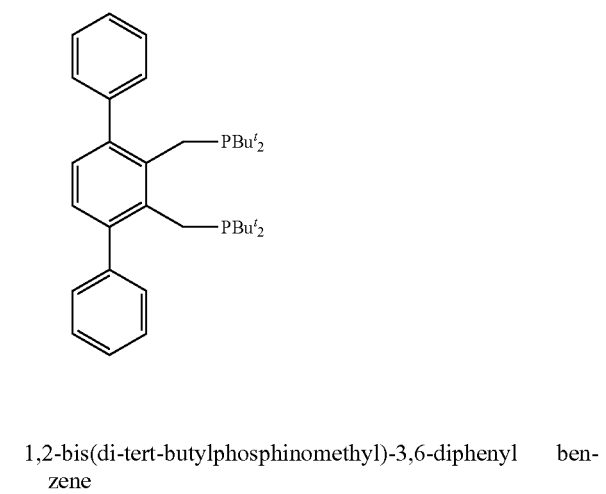

1,2-bis(di-tert-butylphosphinomethyl)-3,6-diphenyl benzene

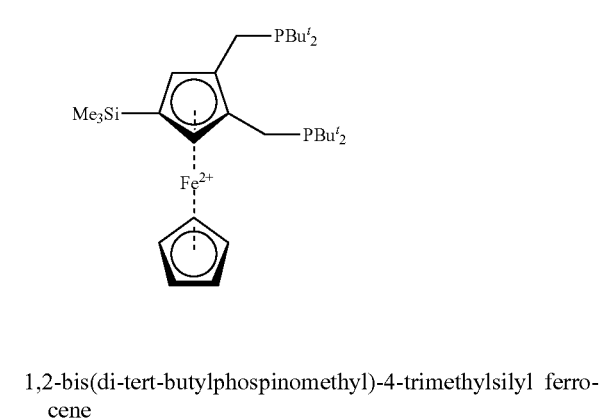

1,2-bis(di-tert-butylphospinomethyl)-4-trimethylsilyl ferrocene

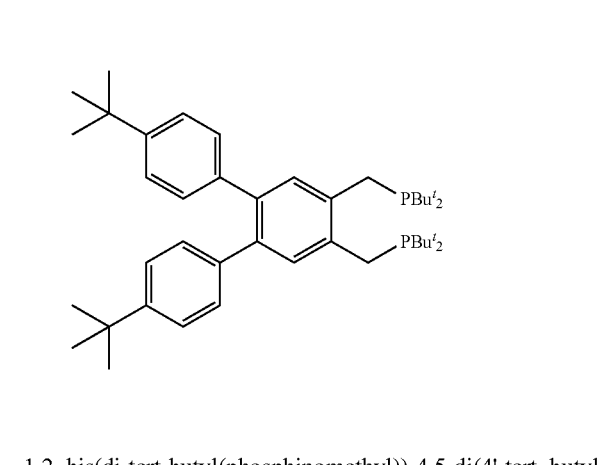

1,2 bis(di-tert-butyl(phosphinomethyl))-4,5-di(4'-tert butyl phenyl)benzene

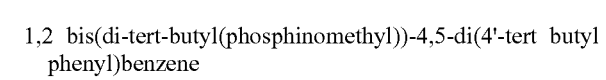

1,2-bis(di-tert-butyl(phosphinomethyl))-4-trimethylsilyl benzene

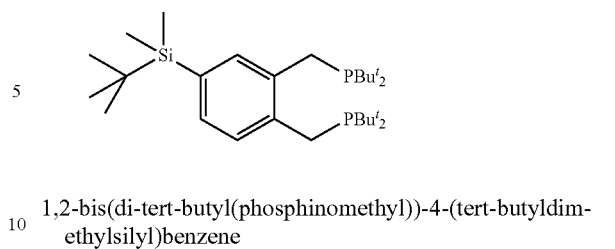

1,2-bis(di-tert-butyl(phosphinomethyl))-4-(tert-butyldimethylsilyl)benzene

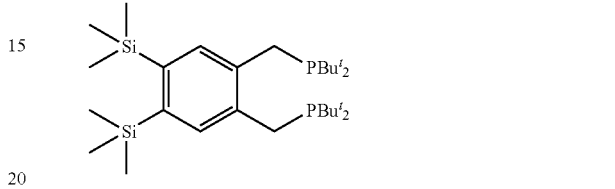

1,2-bis(di-tert-butyl(phosphinomethyl))-4,5-bis(trimethylsilyl)benzene

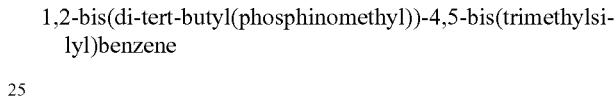

1,2-bis(di-tert-butyl(phosphinomethyl))-4-tert-butyl benzene

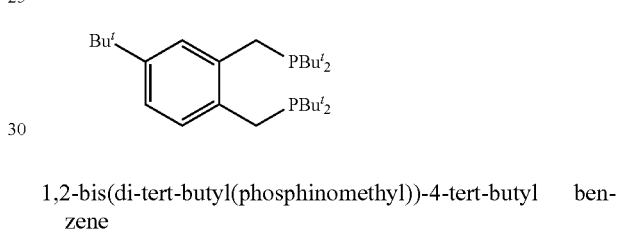

1,2-bis(di-tert-butyl(phosphinomethyl))-4,5-di-tert-butyl benzene

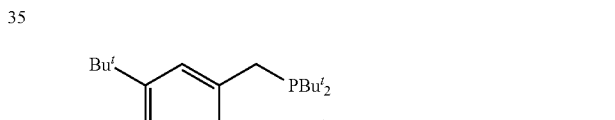

1,2-bis(di-tert-butyl(phosphinomethyl))-4-(tri-tert-butylmethyl)benzene

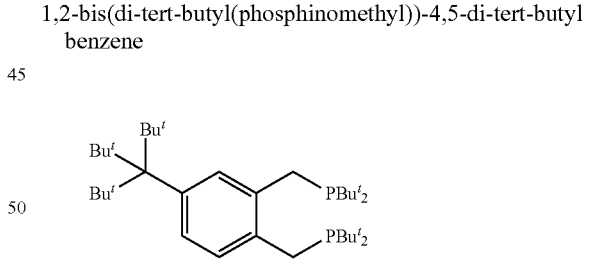

1,2-bis(di-tert-butyl(phosphinomethyl))-4-(tri-tert-butylsilyl)benzene

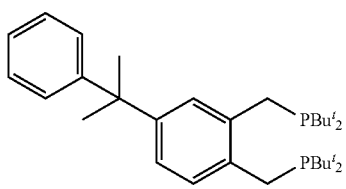

1,2-bis(di-tert-butyl(phosphinomethyl))-4-(2'-phenylprop-2'-yl)benzene

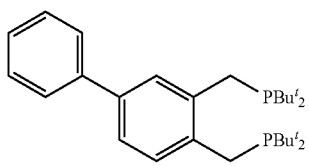

1,2-bis(di-tert-butyl(phosphinomethyl))-4-phenyl benzene

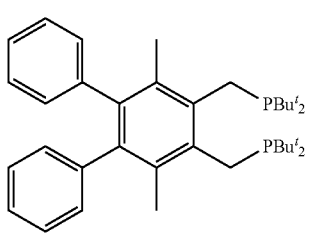

1,2-bis(di-tert-butyl(phosphinomethyl))-3,6-dimethyl-4,5-diphenyl benzene

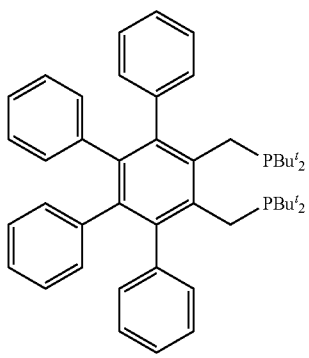

1,2-bis(di-tert-butyl(phosphinomethyl))-3,4,5,6-tetraphenyl benzene

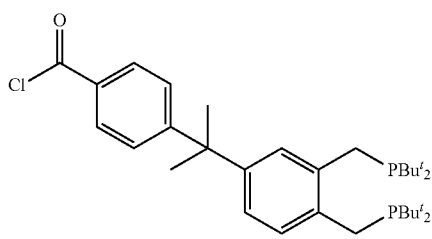

4-(1-{3,4-Bis-[(di-tert-butyl-phosphanyl)-methyl]-phenyl}-1-methyl-ethyl)-benzoyl chloride

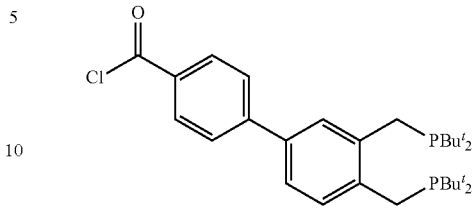

1,2-bis(di-tert-butyl(phosphinomethyl))-4-(4'-chlorocarbonyl-phenyl)benzene

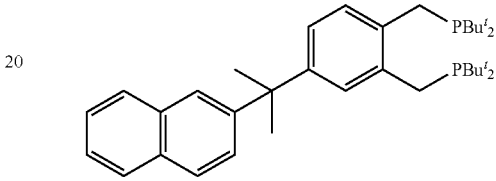

1,2-bis(di-tert-butyl(phosphinomethyl))-4-(2'-naphthyl-prop-2'-yl) benzene

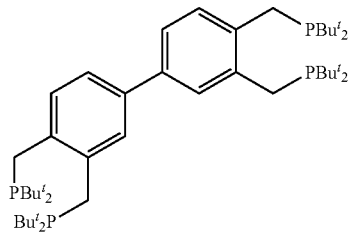

1,2-bis(di-tert-butyl(phosphinomethyl))-4-(3',4'-bis(di-tert-butyl(phosphinomethyl))phenyl)benzene

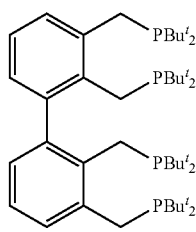

1,2-bis(di-tert-butyl(phosphinomethyl))-3-(2',3'-bis(di-tert-butyl(phosphinomethyl))phenyl)benzene

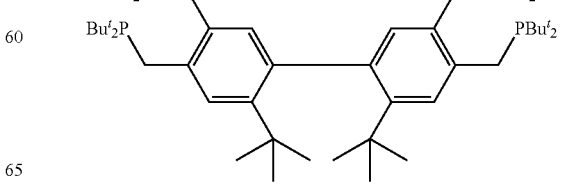

1,2-bis(di-tert-butyl(phosphinomethyl))-4-tertbutyl-5-(2'-tertbutyl-4',5'-bis(di-tert-butyl(phosphinomethyl))phenyl)benzene In the above example, structures of ligands of general formula (I), one or more of the $X^1$-$X^4$ tertiary carbon bearing groups, t-butyl, attached to the $Q^1$ and/or $Q^2$ group phosphorus may be replaced by a suitable alternative. Preferred alternatives are adamantyl, 1,3 dimethyl adamantyl, congressyl, norbornyl or 1-norbondienyl, or $X^1$ and $X^2$ together and/or $X^3$ and $X^4$ together form together with the phosphorus a 2-phospha-tricyclo[3.3.1.1{3,7}decyl group such as 2-phospha-1,3,5,7-tetramethyl-6,9,10-trioxadamantyl or 2-phospha-1,3,5-trimethyl-6,9,10-trioxadamantyl. In most embodiments, it is preferred that the $X^1$-$X^4$ groups or the combined $X^1/X^2$ and $X^3/X^4$ groups are the same but it may also be advantageous to use different groups to produce asymmetry around the active site in these selected ligands and generally in this invention.

Similarly, in all the above example structures of ligands of general formula (I) including the t-butyl alternatives, one of the methylene linking groups representing A or B in formula (I), may as an alternative, be removed so that the respective phosphorus atom, representing $Q^1$ and $Q^2$ is attached directly to the aromatic ring representing R. In these modified example structures, the other methylene group linking the other phosphorus atom is still present so that a $C_3$ bridge connects the two respective phosphorus atoms representing $Q^1$ and $Q^2$ in each example structure.

Preferably, $Q^2$ is phosphorus and preferably, independently, phosphorus.

Preferably, the bidentate ligand is a bidentate phosphine, arsine or stibine ligand, preferably, a phosphine ligand.

For the avoidance of doubt, references to Group 8, 9 or 10 metals herein should be taken to include Groups 8, 9 and 10 in the modern periodic table nomenclature. By the term "Group 8, 9 or 10" we preferably select metals such as Ru, Rh, Os, Ir, Pt and Pd. Preferably, the metals are selected from Ru, Pt and Pd. More preferably, the metal is Pd.

Suitable compounds of such Group 8, 9 or 10 metals include salts of such metals with, or compounds comprising weakly coordinated anions derived from, nitric acid; sulphuric acid; lower alkanoic (up to $C_{12}$) acids such as acetic acid and propionic acid; sulphonic acids such as methane sulphonic acid, chlorosulphonic acid, fluorosulphonic acid, trifluoromethane sulphonic acid, benzene sulphonic acid, naphthalene sulphonic acid, toluene sulphonic acid, e.g. p-toluene sulphonic acid, t-butyl sulphonic acid, and 2-hydroxypropane sulphonic acid; sulphonated ion exchange resins (including low acid level sulphonic resins) perhalic acid such as perchloric acid; halogenated carboxylic acids such as trichloroacetic acid and trifluoroacetic acid; orthophosphoric acid; phosphonic acids such as benzenephosphonic acid; and acids derived from interactions between Lewis acids and Broensted acids. Other sources which may provide suitable anions include the optionally halogenated tetraphenyl borate derivatives, e.g. perfluorotetraphenyl borate. Additionally, zero valent palladium complexes particularly those with labile ligands, e.g. triphenylphosphine or alkenes such as dibenzylideneacetone or styrene or tri(dibenzylideneacetone)dipalladium may be used. The above anions may be introduced directly as a compound of the metal but should preferably be introduced to the catalyst system independently of the metal or metal compound.

The anion may be derived from or introduced as one or more of an acid having a pKa measured in dilute aqueous solution at 18° C. of less than 6, more preferably, less than 5, most preferably less than 4, a salt with a cation that does not interfere with the reaction, e.g. metal salts or largely organic salts such as alkyl ammonium, and a precursor, such as an ester, that can break down under reaction conditions to generate the anion in situ. Suitable acids and salts include the acids and salts listed supra.

Particularly preferred acid promoters for an alkoxycarbonylation are the sulfonic acids, including the sulfonated ion exchange resins, and the carboxylic acids listed supra. The low level acid ion exchange resins that may be used preferably provide a level of $SO_3H$/Pd ratio in the reaction of less than 35 mol/mol, more preferably less than 25 mol/mol, most preferably less than 15 mol/mol. Typical ranges for the $SO_3H$ concentration provided by the resin are in the range 1-40 mol/mol Pd, more typically, 2-30 mol/mol Pd, most typically 3-20 mol/mol Pd.

Generally the anion(s) can be selected which is appropriate to the reaction. Certain ethylenically unsaturated compounds may be more sensitive to the pKa of the acid of the anion than others and conditions and solvent can be varied as appropriate within the skill of the person in the art For instance, in butadiene carbonylation the pKa of the acid of the anion should be greater than 2 in dilute aqueous solution at 18° C., more preferably, having a pka between 2 and 5.

In a carbonylation reaction, the quantity of anion present is not critical to the catalytic behaviour of the catalyst system. The molar ratio of anion to Group 8, 9 or 10 metal or compound may be from 1:1 to 10000:1, preferably from 10:1 to 2000:1 and particularly from 100:1 to 1000:1. Where the anion is provided by an acid and salt, the relative proportion of the acid and salt is not critical. However, where an anion is provided by acid or partially provided by acid the ratio of acid to group 8, 9 or 10 metal is preferably, in the same ratios as the anion to metal or compound above. By $H^+$ is meant the amount of active acidic sites so that a mole of monobasic acid would have 1 mole of $H^+$ whereas a mole of dibasic acid would have 2 moles of $H^+$ and tribasic acids etc should be interpreted accordingly. Similarly, by $C^{2+}$ is meant moles of metal having a $2^+$ cationic charge so that for $M^+$ ions the ratio of the metal cation should be adjusted accordingly. For example, an $M^+$ cation should be taken as having 0.5 moles of $C^{2+}$ per mole of $M^+$.

In an alkoxycarbonylation reaction, preferably, the ratio of bidentate ligand to acid is at least 1:2 mol/mol($H^+$) and preferably, the ratio of bidentate ligand to group 8, 9 or 10 metal is at least 1:1 mol/mol($C^{2+}$). Preferably, the ligand is in excess of metal mol/mol($C^{2+}$) and preferably in excess of a ratio of 1:2 mol/mol($H^+$) with the acid. Excess ligand is advantageous as the ligand itself may act as a base to buffer the acid levels in the reaction and prevent degradation of substrate. On the other hand the presence of acid activates the reaction mix and improves the overall rate of reaction.

In an hydroxycarbonylation reaction, preferably, the ratio of bidentate ligand to acid is at least 1:2 mol/mol($H^+$) and preferably, the ratio of bidentate ligand to group 8, 9 or 10 metal is at least 1:1 mol/mol($C^{2+}$). Preferably, the ligand is in excess of metal mol/mol($C^{2+}$). Excess ligand may be advantageous as the ligand itself may act as a base to buffer the acid levels in the reaction and prevent degradation of substrate. On the other hand the presence of acid activates the reaction mix and improves the overall rate of reaction.

As mentioned, the catalyst system of the present invention may be used homogeneously or heterogeneously. Preferably, the catalyst system is used homogeneously.

Suitably, the process of the invention may be used to catalyse the carbonylation of ethylenically unsaturated compounds in the presence of carbon monoxide and a hydroxyl group containing compound and, optionally, a source of anions. The ligands of the invention yield a surprisingly high TON in carbonylation reactions such as ethylene, propylene, 1,3-butadiene, pentenenitrile, and octene carbonylation. Consequently, the commercial viability of a carbonylation process will be increased by employing the process of the invention.

Advantageously, use of the catalyst system of the present invention in the carbonylation of ethylenically unsaturated compounds etc also gives good rates especially for alkoxy- and hydroxycarbonylation.

References to ethylenically unsaturated compounds herein should be taken to include any one or more unsaturated C—C bond(s) in a compound such as those found in alkenes, alkynes, conjugated and unconjugated dienes, functional alkenes etc.

Suitable ethylenically unsaturated compounds for the invention are ethylenically unsaturated compounds having from 2 to 50 carbon atoms per molecule, or mixtures thereof. Suitable ethylenically unsaturated compounds may have one or more isolated or conjugated unsaturated bonds per molecule. Preferred are compounds having from 2 to 20 carbon atoms, or mixtures thereof, yet more preferred are compounds having at most 18 carbon atoms, yet more at most 16 carbon atoms, again more preferred compounds have at most 10 carbon atoms. The ethylenically unsaturated compound may further comprise functional groups or heteroatoms, such as nitrogen, sulphur or oxide. Examples include carboxylic acids, esters or nitriles as functional groups. In a preferred group of processes, the ethylenically unsaturated compound is an olefin or a mixture of olefins. Suitable ethylenically unsaturated compounds include acetylene, methyl acetylene, propyl acetylene, 1,3-butadiene, ethylene, propylene, butylene, isobutylene, pentenes, pentene nitriles, alkyl pentenoates such as methyl 3-pentenoates, pentene acids (such as 2- and 3-pentenoic acid), heptenes, vinyl esters such as vinyl acetate, octenes, dodecenes.

Particularly preferred ethylenically unsaturated compounds are ethylene, vinyl acetate, 1,3-butadiene, alkyl pentenoates, pentenenitriles, pentene acids (such as 3 pentenoic acid), acetylene, heptenes, butylene, octenes, dodecenes and propylene.

Especially preferred ethylenically unsaturated compounds are ethylene, propylene, heptenes, octenes, dodecenes, vinyl acetate, 1,3-butadiene and pentene nitriles.

Still further, it is possible to carbonylate mixtures of alkenes containing internal double bonds and/or branched alkenes with saturated hydrocarbons. Examples are raffinate 1, raffinate 2 and other mixed streams derived from a cracker, or mixed streams derived from alkene dimerisation (butene dimerisation is one specific example) and fischer tropsch reactions.

References to vinyl esters herein include references to substituted or unsubstituted vinyl ester of formula (IV):

wherein $R^{62}$ may be selected from hydrogen, alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{27}R^{28}$, $SR^{29}$, $C(O)SR^{30}$ wherein $R^{49}$-$R^{30}$ are as defined herein.

Preferably, $R^{62}$ is selected from hydrogen, alkyl, phenyl or alkylphenyl, more preferably, hydrogen, phenyl, $C_1$-$C_6$ alkylphenyl or $C_1$-$C_6$ alkyl, such as methyl, ethyl, propyl, butyl, pentyl and hexyl, even more preferably, $C_1$-$C_6$ alkyl, especially methyl.

Preferably, $R^{63}$-$R^{65}$ each independently represents hydrogen, alkyl, aryl or Het as defined herein. Most preferably, $R^{63}$-$R^{65}$ independently represents hydrogen.

Optionally, however, reference to ethylenically unsaturated compounds herein can exclude vinyl esters including vinyl acetate.

Where a compound of a formula herein (e.g. formulas I or IV) contains an alkenyl group or a cycloalkyl moiety as defined, cis (E) and trans (Z) isomerism may also occur. The present invention includes the individual stereoisomers of the compounds of any of the formulas defined herein and, where appropriate, the individual tautomeric forms thereof, together with mixtures thereof. Separation of diastereoisomers or cis and trans isomers may be achieved by conventional techniques, e.g. by fractional crystallisation, chromatography or H.P.L.C. of a stereoisomeric mixture of a compound one of the formulas or a suitable salt or derivative thereof. An individual enantiomer of a compound of one of the formulas may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

All stereoisomers are included within the scope of the process of the invention.

It will be appreciated by those skilled in the art that the compounds of formula (I) may function as ligands that coordinate with the Group 8, 9 or 10 metal or compound thereof to form the compounds for use in the invention. Typically, the Group 8, 9 or 10 metal or compound thereof coordinates to the one or more phosphorus, arsenic and/or antimony atoms of the compound of formula (I).

As mentioned above, the present invention provides a process for the carbonylation of ethylenically unsaturated compound comprising contacting an ethylenically unsaturated compound with carbon monoxide and a source of hydroxyl groups such as water or an alkanol in the presence of a catalyst compound as defined in the present invention.

Suitably, the source of hydroxyl groups includes an organic molecule having an hydroxyl functional group. Preferably, the organic molecule having a hydroxyl functional group may be branched or linear, and comprises an alkanol, particularly a $C_1$-$C_{30}$ alkanol, including aryl alkanols, which may be optionally substituted with one or more substituents selected from alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{27}R^{28}$, $SR^{29}$ or $C(O)SR^{30}$ as defined herein. Highly preferred alkanols are $C_1$-$C_8$ alkanols such as methanol, ethanol, propanol, iso-propanol, iso-butanol, t-butyl alcohol, n-butanol, phenol and chlorocapryl alcohol. Although the monoalkanols are most preferred, poly-alkanols, preferably, selected from di-octa ols such as diols, triols, tetra-ols and sugars may also be utilised. Typically, such polyalkanols are selected from 1,2-ethanediol, 1,3-propanediol, glycerol, 1,2,4 butanetriol, 2-(hydroxymethyl)-1,3-propanediol, 1,2,6 trihydroxyhexane, pentaerythritol, 1,1,1 tri(hydroxymethyl)ethane, nannose, sorbase, galactose and other sugars. Preferred sugars include sucrose, fructose and glucose. Especially preferred alkanols are methanol and ethanol. The most preferred alkanol is methanol.

The amount of alcohol is not critical. Generally, amounts are used in excess of the amount of substrate to be carbonylated. Thus the alcohol may serve as the reaction solvent as well, although, if desired, separate solvents may also be used.

It will be appreciated that the end product of the reaction is determined at least in part by the source of alkanol used. For instance, use of methanol produces the corresponding methyl ester. Conversely, use of water produces the corresponding acids. Accordingly, the invention provides a convenient way of adding the group —C(O)O $C_1$-$C_{30}$ alkyl or aryl or —C(O)OH across the ethylenically unsaturated bond.

In the process according to the second aspect of the present invention, the carbon monoxide may be used in pure form or diluted with an inert gas such as nitrogen, carbon dioxide or a noble gas such as argon. Small amounts of hydrogen, typically less than 5% by volume, may also be present.

The ratio (volume/volume) of ethylenically unsaturated compounds to hydroxyl group source in a liquid phase reaction medium may vary between wide limits and suitably lies in the range of 1:0.1 to 1:10, preferably from between 2:1 to 1:2 and up to a large excess of alkanol or water when the latter is also the reaction solvent such as up to a 100:1 excess of alkanol or water. However, if the ethylenically unsaturated compound is a gas at the reaction temperature it may be present at lower levels in the liquid phase reaction medium such as at a ratio to hydroxyl group source of 1:20,000 to 1:10 more preferably, 1:10,000 to 1:50, most preferably, 1:5000 to 1:500

The amount of the catalyst of the invention used in the carbonylation process is not critical. Good results may be obtained when, preferably, the amount of Group 8, 9 or 10 metal is in the range $10^{-7}$ to $10^{-1}$, more preferably, $10^{-6}$ to $10^{-2}$, most preferably, $10^{-5}$ to $10^{-2}$ moles per mole of ethylenically unsaturated compound in the liquid phase carbonylation reaction medium.

Suitably, although non-essential to the invention, the carbonylation of ethylenically unsaturated compound as defined herein may be performed in one or more aprotic solvents.

Suitable solvents include ketones, such as for example methylbutylketone; ethers, such as for example anisole (methyl phenyl ether), 2,5,8-trioxanonane (diglyme), diethyl ether, dimethyl ether, tetrahydrofuran, diphenylether, diisopropylether and the dimethylether of di-ethylene-glycol; esters, such as for example methylacetate, dimethyladipate methyl benzoate, dimethyl phthalate and butyrolactone; amides, such as for example dimethylacetamide, N-methylpyrrolidone and dimethyl formamide; sulfoxides and sulphones, such as for example dimethylsulphoxide, di-isopropylsulphone, sulfolane (tetrahydrothiophene-2,2-dioxide), 2-methylsulfolane, diethyl sulphone, tetrahydrothiophene 1,1-dioxide and 2-methyl-4-ethylsulfolane; aromatic compounds, including halo variants of such compounds e.g. benzene, toluene, ethyl benzene o-xylene, m-xylene, p-xylene, chlorobenzene, o-dichlorobenzene, m-dichlorobenzene: alkanes, including halo variants of such compounds egg, hexane, heptane, 2,2,3-trimethylpentane, methylene chloride and carbon tetrachloride; nitriles e.g. benzonitrile and acetonitrile.

Very suitable are aprotic solvents having a dielectric constant that is below a value of 50, more preferably in the range of 3 to 8, at 298.15 K and $1 \times 10^5$ $Nm^{-2}$. In the present context, the dielectric constant for a given solvent is used in its normal meaning of representing the ratio of the capacity of a condenser with that substance as dielectric to the capacity of the same condenser with a vacuum for dielectric. Values for the dielectric constants of common organic liquids can be found in general reference books, such as the Handbook of Chemistry and Physics, 76$^{th}$ edition, edited by David R. Lide et al, and published by CRC press in 1995, and are usually quoted for a temperature of about 20° C. or 25° C., i.e. about 293.15 k or 298.15 K, and atmospheric pressure, i.e. about $1 \times 10^5$ $Nm^{-2}$, or can readily be converted to that temperature and pressure using the conversion factors quoted. If no literature data for a particular compound is available, the dielectric constant may be readily measured using established physico-chemical methods.

For example, the dielectric constant of anisole is 4.3 (at 294.2 K), of diethyl ether is 4.3 (at 293.2 K), of sulfolane is 43.4 (at 303.2 K), of methylpentanoate is 5.0 (at 293.2 K), of diphenylether is 3.7 (at 283.2 K), of dimethyladipate is 6.8 (at 293.2 K), of tetrahydrofuran is 7.5 (at 295.2 K), of methylnonanoate is 3.9 (at 293.2 K). A preferred aprotic solvent is anisole.

In the presence of an alkanol, an aprotic solvent will be generated by the reaction as the ester carbonylation product of the ethylenically unsaturated compound, carbon monoxide and the alkanol is an aprotic solvent.

The process may be carried out in an excess of aprotic solvent, i.e. at a ratio (v/v) of aprotic solvent to alkanol of at least 1:1. Preferably, this ratio ranges from 1:1 to 10:1 and more preferably from 1:1 to 5:1. Most preferably the ratio (v/v) ranges from 1.5:1 to 3:1.

Despite the foregoing it is preferred that the reaction is carried out in the absence of any external added aprotic solvent i.e. in the absence of an aprotic solvent not generated by the reaction itself.

During hydroxycarbonylation, the presence of a protic solvent is also preferred. The protic solvent may include a carboxylic acid or an alcohol. Mixtures of the aprotic and protic solvents may also be employed.

Hydrogen may be added to the carbonylation reaction to improve reaction rate. Suitable levels of hydrogen when utilised may be in the ratio of between 0.1 and 20% vol/vol of the carbon monoxide, more preferably, 1-20% vol/vol of the carbon monoxide, more preferably, 2-15% vol/vol of the carbon monoxide, most preferably 3-10% vol/vol of carbon monoxide.

The catalyst compounds of the present invention may act as a "heterogeneous" catalyst or a "homogeneous" catalyst, preferably, a homogenous catalyst.

By the term "homogeneous" catalyst we mean a catalyst, i.e. a compound of the invention, which is not supported but is simply admixed or formed in-situ with the reactants of the carbonylation reaction (e.g. the ethylenically unsaturated compound, the hydroxyl containing compound and carbon monoxide), preferably in a suitable solvent as described herein.

By the term "heterogeneous" catalyst we mean a catalyst, i.e. the compound of the invention, which is carried on a support.

Thus according to a further aspect, the present invention provides a process for the carbonylation of ethylenically unsaturated compounds as defined herein wherein the process is carried out with the catalyst comprising a support, preferably an insoluble support.

Preferably, the support comprises a polymer such as a polyolefin, polystyrene or polystyrene copolymer such as a divinylbenzene copolymer or other suitable polymers or copolymers known to those skilled in the art; a silicon derivative such as a functionalised silica, a silicone or a silicone rubber; or other porous particulate material such as for example inorganic oxides and inorganic chlorides.

Preferably the support material is porous silica which has a surface area in the range of from 10 to 700 m$^2$/g, a total pore volume in the range of from 0.1 to 4.0 cc/g and an average particle size in the range of from 10 to 500 µm. More preferably, the surface area is in the range of from 50 to 500 m$^2$/g, the pore volume is in the range of from 0.5 to 2.5 cc/g and the average particle size is in the range of from 20 to 200 µm. Most desirably the surface area is in the range of from 100 to 400 m$^2$/g, the pore volume is in the range of from 0.8 to 3.0 cc/g and the average particle size is in the range of from 30 to 100 µm. The average pore size of typical porous support materials is in the range of from 10 to 1000 Å. Preferably, a support material is used that has an average pore diameter of from 50 to 500 Å, and most desirably from 75 to 350 Å. It may be particularly desirable to dehydrate the silica at a temperature of from 100° C. to 800° C. anywhere from 3 to 24 hours.

Suitably, the support may be flexible or a rigid support, the insoluble support is coated and/or impregnated with the compounds of the process of the invention by techniques well known to those skilled in the art.

Alternatively, the compounds of the process of the invention are fixed to the surface of an insoluble support, optionally via a covalent bond, and the arrangement optionally includes a bifunctional spacer molecule to space the compound from the insoluble support.

The compounds of the invention may be fixed to the surface of the insoluble support by promoting reaction of a functional group present in the compound of formula 1, for example a substituent of the aromatic structure, with a complimentary reactive group present on or previously inserted into the support. The combination of the reactive group of the support with a complimentary substituent of the compound of the invention provides a heterogeneous catalyst where the compound of the invention and the support are linked via a linkage such as an ether, ester, amide, amine, urea, keto group.

The choice of reaction conditions to link a compound of the process of the present invention to the support depends upon the ethylenically unsaturated compound and the groups of the support. For example, reagents such as carbodiimides, 1,1'-carbonyldiimidazole, and processes such as the use of mixed anhydrides, reductive amination may be employed.

According to a further aspect, the present invention provides the use of the process or ligand catalyst composition of any aspect of the invention wherein the catalyst is attached to a support.

Additionally, the bidentate phosphine may be bonded to a suitable polymeric substrate via at least one of the bridge substituents, the bridging group R, the linking group A or the linking group B e.g. 1,2 bis(di-t-butylphosphinomethyl)-4-t-butyl-benzene may be bonded, preferably, via the 3, 5 or 6 cyclic carbons of the benzene group to polystyrene to give an immobile heterogeneous catalyst.

The amount of bidentate ligand used can vary within wide limits. Preferably, the bidentate ligand is present in an amount such that the ratio of the number of moles of the bidentate ligand present to the number of moles of the Group 8, or 10 metal present is from 1 to 50 e.g. 1 to 15 and particularly from 1 to 10 mol per mol of metal. More preferably, the mol: mol range of compounds of formula 1 to Group 8, 9 or 10 metal is in the range of 1:1 to 20:1, most preferably in the range of 1:1 to 10:1 or even 1:1 to 1.5:1. Conveniently, the possibility of applying these low molar ratios is advantageous, as it avoids the use of an excess of the compound of formula I and hence minimises the consumption of these usually expensive compounds. Suitably, the catalysts of the invention are prepared in a separate step preceding their use in-situ in the carbonylation reaction.

Conveniently, the process of the invention may be carried out by dissolving the Group 8, 9 or 10 metal or compound thereof as defined herein in a suitable solvent such as one of the alkanols or aprotic solvents previously described (a particularly preferred solvent would be the ester or acid product of the specific carbonylation reaction e.g. 2-acetoxymethylpropionate or 3-acetoxymethylpropionate for vinyl acetate carbonylation or methyl propionate for ethylene carbonylation) and subsequently admixing with a compound of formula 1 as defined herein.

The carbon monoxide may be used in the presence of other gases which are inert in the reaction. Examples of such gases include hydrogen, nitrogen, carbon dioxide and the noble gases such as argon.

The product of the reaction may be separated from the other components by any suitable means. However, it is an advantage of the present process that significantly fewer by-products are formed thereby reducing the need for further purification after the initial separation of the product as may be evidenced by the generally significantly higher selectivity. A further advantage is that the other components which contain the catalyst system which may be recycled and/or reused in further reactions with minimal supplementation of fresh catalyst.

Preferably, the carbonylation is carried out at temperatures of between −30 to 170° C., more preferably −10° C. to 160° C., most preferably 20° C. to 150° C. An especially preferred temperature is one chosen between 40° C. to 150° C. Advantageously, the carbonylation can be carried out at moderate temperatures, it is particularly advantageous to be able to carry out the reaction at room temperature (20° C.)

Preferably, when operating a low temperature carbonylation, the carbonylation is carried out between −30° C. to 49° C., more preferably, −10° C. to 45° C., still more preferably 0° C. to 45° C., most preferably 10° C. to 45° C. Especially preferred is a range of 10 to 35° C.

Preferably, the carbonylation is carried out at a CO partial pressure of between $0.80 \times 10^5$ N·m$^{-2}$–$90 \times 10^5$ N·m$^{-2}$, more preferably $1 \times 10^5$ N·m$^{-2}$–$65 \times 10^5$ N·m$^{-2}$, most preferably $1-50 \times 10^5$ N·m$^{-2}$. Especially preferred is a CO partial pressure of 5 to $45 \times 10^5$ N·m$^{-2}$.

Preferably, a low pressure carbonylation is also envisaged. Preferably, when operating a low pressure carbonylation the carbonylation is carried out at a CO partial pressure of between 0.1 to $5 \times 10^5$ N·m$^{-2}$, more preferably 0.2 to $2 \times 10^5$ N·m$^{-2}$, most preferably 0.5 to $1.5 \times 10^5$ N·m$^{-2}$.

There is no particular restriction on the duration of the carbonylation except that carbonylation in a timescale which is commercially acceptable is obviously preferred. Carbonylation in a batch reaction may take place in up to 48 hours, more typically, in up to 24 hours and most typically in up to 12 hours. Typically, carbonylation is for at least 5 minutes, more typically, at least 30 minutes, most typically, at least 1 hour. In a continuous reaction such time scales are obviously irrelevant and a continuous reaction can continue as long as the TON is commercially acceptable before catalyst requires replenishment.

The catalyst system of the present invention is preferably constituted in the liquid phase which may be formed by one or more of the reactants or by the use of a suitable solvent.

The use of stabilising compounds with the catalyst system may also be beneficial in improving recovery of metal which has been lost from the catalyst system. When the catalyst system is utilized in a liquid reaction medium such stabilizing compounds may assist recovery of the group 8, 9 or 10 metal.

Preferably, therefore, the catalyst system includes in a liquid reaction medium a polymeric dispersant dissolved in a liquid carrier, said polymeric dispersant being capable of stabilising a colloidal suspension of particles of the group 8, 9 or 10 metal or metal compound of the catalyst system within the liquid carrier.

The liquid reaction medium may be a solvent for the reaction or may comprise one or more of the reactants or reaction products themselves. The reactants and reaction products in liquid form may be miscible with or dissolved in a solvent or liquid diluent.

The polymeric dispersant is soluble in the liquid reaction medium, but should not significantly increase the viscosity of the reaction medium in a way which would be detrimental to reaction kinetics or heat transfer. The solubility of the dispersant in the liquid medium under the reaction conditions of temperature and pressure should not be so great as to deter significantly the adsorption of the dispersant molecules onto the metal particles.

The polymeric dispersant is capable of stabilising a colloidal suspension of particles of said group 8, 9 or 10 metal or metal compound within the liquid reaction medium such that the metal particles formed as a result of catalyst degradation are held in suspension in the liquid reaction medium and are discharged from the reactor along with the liquid for reclamation and optionally for re-use in making further quantities of catalyst. The metal particles are normally of colloidal dimensions, e.g. in the range 5-100 nm average particle size although larger particles may form in some cases. Portions of the polymeric dispersant are adsorbed onto the surface of the metal particles whilst the remainder of the dispersant molecules remain at least partially solvated by the liquid reaction medium and in this way the dispersed group 8, 9 or 10 metal particles are stabilised against settling on the walls of the reactor or in reactor dead spaces and against forming agglomerates of metal particles which may grow by collision of particles and eventually coagulate. Some agglomeration of particles may occur even in the presence of a suitable dispersant but when the dispersant type and concentration is optimised then such agglomeration should be at a relatively low level and the agglomerates may form only loosely so that they may be broken up and the particles redispersed by agitation.

The polymeric dispersant may include homopolymers or copolymers including polymers such as graft copolymers and star polymers.

Preferably, the polymeric dispersant has sufficiently acidic or basic functionality to substantially stabilise the colloidal suspension of said group 8, 9 or 10 metal or metal compound.

By substantially stabilise is meant that the precipitation of the group 8, 9 or 10 metal from the solution phase is substantially avoided.

Particularly preferred dispersants for this purpose include acidic or basic polymers including carboxylic acids, sulphonic acids, amines and amides such as polyacrylates or heterocycle, particularly nitrogen heterocycle, substituted polyvinyl polymers such as polyvinyl pyrrolidone or copolymers of the aforesaid.

Examples of such polymeric dispersants may be selected from polyvinylpyrrolidone, polyacrylamide, polyacrylonitrile, polyethylenimine, polyglycine, polyacrylic acid, polymethacrylic acid, poly(3-hydroxybutyricacid), poly-L-leucine, poly-L-methionine, poly-L-proline, poly-L-serine, poly-L-tyrosine, poly(vinylbenzenesulphonic acid) and poly(vinylsulphonic acid), acylated polyethylenimine. Suitable acylated polyethylenimines are described in BASF patent publication EP1330309 A1 and U.S. Pat. No. 6,723,882.

Preferably, the polymeric dispersant incorporates acidic or basic moieties either pendant or within the polymer backbone. Preferably, the acidic moieties have a dissociation constant ($pK_a$) of less than 6.0, more preferably, less than 5.0, most preferably less than 4.5. Preferably, the basic moieties have a base dissociation constant ($pK_b$) being of less than 6.0, more preferably less than 5.0 and most preferably less than 4.5, $pK_a$ and $pK_b$ being measured in dilute aqueous solution at 25° C.

Suitable polymeric dispersants, in addition to being soluble in the reaction medium at reaction conditions, contain at least one acidic or basic moiety, either within the polymer backbone or as a pendant group. We have found that polymers incorporating acid and amide moieties such as polyvinylpyrrolidone (PVP) and polyacrylates such as polyacrylic acid (PAA) are particularly suitable. The molecular weight of the polymer which is suitable for use in the invention depends upon the nature of the reaction medium and the solubility of the polymer therein. We have found that normally the average molecular weight is less than 100,000. Preferably, the average molecular weight is in the range 1,000-200,000, more preferably, 5,000-100,000, most preferably, 10,000-40,000 e.g. Mw is preferably in the range 10,000-80,000, more preferably 20,000-60,000 when PVP is used and of the order of 1,000-10,000 in the case of PAA.

The effective concentration of the dispersant within the reaction medium should be determined for each reaction/catalyst system which is to be used.

The dispersed group 8, 9 or 10 metal may be recovered from the liquid stream removed from the reactor e.g. by filtration and then either disposed of or processed for re-use as a catalyst or other applications. In a continuous process the liquid stream may be circulated through an external heat-exchanger and in such cases it may be convenient to locate filters for the palladium particles in these circulation apparatus.

Preferably, the polymer:metal mass ratio in g/g is between 1:1 and 1000:1, more preferably, between 1:1 and 400:1, most preferably, between 1:1 and 200:1. Preferably, the polymer:metal mass ratio in g/g is up to 1000, more preferably, up to 400, most preferably, up to 200.

It will be appreciated that any of the features set forth in the first aspect of the invention may be regarded as preferred features of the second, third, fourth, fifth or other aspect of the present invention and vice versa.

The invention not only extends to novel bidentate ligands of formula (I) but also novel complexes of such ligands with the metal of Group 8, 9 or 10 or a compound thereof.

The invention will now be described and illustrated by way of the following non-limiting examples and comparative examples.

SYNTHESIS EXAMPLES

Preparation of Example Ligands of the Invention is as Follows

Compound 1

Synthesis of 1,2-bis(di-tert-butylphosphinomethyl)-4trimethylsilyl benzene

Part (I)

Synthesis of 4-trimethylsilyl-o-xylene

Magnesium ribbon (2.91 g, 115.41 mmol) was added to a schlenk flask. To this was added a few (3-4) crystals of iodine. THF (150 ml) was then added to give an orange/yellow solution. 4-bromo-o-xylene (19.41 g, 104.91 mmol) was diluted with THF (80 ml) and then added slowly over one hour to the magnesium suspension, the reaction flask being placed in a warm (50° C.) water bath for the duration of the reaction. This gave a dark orange/brown solution with some insoluble magnesium. This solution was then heated to 85° C. for one hour. The solution was then allowed to cool to room temperature before being cannula transferred into a clean schlenk away for the unreacted magnesium. The THF solution was then cooled to −78° C. before trimethylsilyl chloride (13.41 ml, 104.91 mmol) was added by syringe. The resultant solution was then allowed to stir at −78° C. for thirty minutes before being allowed to warm to room temperature. The resultant solution was then stirred at room temperature overnight. The solution was quenched by the addition of water (100 ml). Ether (100 ml) was then added and the biphasic mixture separated. The aqueous layer was washed with ether (100 ml) and the organic extracts combined. The organic extracts were then dried over sodium sulphate before being filtered. The filtrate was then dried under vacuum to give a colourless oil. Yield=14.47 g, 77%.

Part (II)

The 4-trimethylsilyl-o-xylene (5.00 g, 28.1 mmol) (prepared in Part (I) was diluted with heptane (100 ml) and to this was added NaOBu$^t$ (8.1 g, 84.3 mmol), TMEDA (12.6 ml, 84.3 mmol) and Bu"Li (2.5M in hexanes, 33.7 ml, 84.3 mmol). The butyl lithium was added dropwise and gave an immediate colour change from colourless to yellow to orange to dark red. The solution was then heated to 65° C. for three hours. This gave a brown/orange suspension. The suspension was cooled to room temperature and the supernatant liquid removed by cannula. The brown precipitate residue was then washed with pentane (100 ml). The pentane washings were then removed by cannula. The solid residue was then suspended in pentane (100 ml) and then cooled in a cold water bath. Bu$^t_2$PCl (7.5 ml, 39.3 mmol) was then added dropwise to the suspension. The resultant suspension was then stirred for three hours and stood overnight. Water (100 ml) was degassed with nitrogen gas for 30 minutes and then added to the suspension. This gave a biphasic solution. The upper (organic phase) was diluted with pentane (100 ml) and the organic phase removed by cannula into a clean schlenk flask. The pentane extract was then dried over sodium sulphate and transferred into a clean schlenk flask by cannula. The solvent was then removed under vacuum to give orange oil. To this was added methanol (100 ml) which give a biphasic solution. This was then heated to reflux (70° C.) which gave a pale yellow solution and some colourless insoluble material. The solution was then cooled to room temperature and filtered into a clean schlenk flask. The solution was then placed in the freezer at −20° C. overnight. This gave the deposition of an off-white solid. The remaining methanol solution was then removed by cannula and the solid dried under vacuum. The solid was isolated in the glovebox. Yield=4.70 g, 36%. 92% pure. $^{31}$P {$^1$H} NMR (CDCl$_3$, 161.9 MHz, δ); 27.3 (s), 26.1 (s) ppm.

Compound 2

Synthesis of 1,2-bis(di-tert-butylphosphinomethyl)-4-tert-butyl-benzene

The 4-tert-butyl-o-xylene (4.55 g, 28.1 mmol) (Aldrich) was diluted with heptane (100 ml) and to this was added NaOBu$^t$ (8.1 g, 84.3 mmol), TMEDA (12.6 ml, 84.3 mmol) and Bu"Li (2.5M in hexanes, 33.7 ml, 84.3 mmol). The butyl lithium was added dropwise and gave an immediate colour change from colourless to yellow to orange to dark red. The solution was then heated to 65° C. for three hours. This gave a brown/orange suspension. The suspension was cooled to room temperature and the supernatant liquid removed by cannula the brown precipitate residue was then washed with pentane (100 ml. The pentane washings were then removed by cannula. The solid residue was then suspended in pentane (100 ml) and then cooled in a cold water bath. Bu$^t_2$PCl (7.5 ml, 39.3 mmol) was then added dropwise to the suspension. The resultant suspension was then stirred for three hours and stood overnight. Water (100 ml) was degassed with nitrogen gas for 30 minutes and then added to the suspension. This gave a biphasic solution. The upper (organic phase) was diluted with pentane (100 ml) and the organic phase removed by cannula into a clean schlenk flask. The pentane extract was then dried over sodium sulphate and transferred into a clean schlenk flask by cannula. The solvent was then removed under vacuum to give orange oil. To this was added methanol (100 ml) which give a biphasic solution. This was then heated to reflux (70° C.) which gave a pale yellow solution and some colourless insoluble material. The solution was then cooled to room temperature and filtered into a clean schlenk flask. The solution was then placed in the freezer at −20° C. overnight. This gave the deposition of an off-white solid. The remaining methanol solution was then removed by cannula and the solid dried under vacuum. The solid was isolated in the glovebox. Yield=4.20 g, 33%. 95% pure. $^{31}$P {$^1$H} NMR (CDCl$_3$, 161.9 MHz, δ); 27.1 (s), 26.3 (s) ppm.

Compound 3

Synthesis of 1,2-bis(di-tert-butylphosphinomethyl)-1'-(triphenylsilyl) ferrocene Part (I)

Preparation of 1-bromo-1'-triphenylsilyl ferrocene

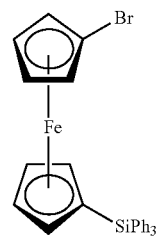

To 1,1'-dibromoferrocene (10.14 g, 29.49 mmol) in dry THF (200 ml) cooled to −78° C. (dry ice/acetone bath) was added n-butyllithium (12.56 ml, 28.02 mmol, 0.95 eq) and the reaction was stirred under N$_2$ for 30 min. Chlorotriphenylsilane (8.26 g, 28.02 mmol, 0.95 eq) dissolved in the minimum amount of dry THF was then added dropwise and the solution was then allowed to warm up to room temperature and further stirred for twelve hours resulting in a red solution.

The reaction was then quenched with water, and stirred for a further fifteen minutes. The ethereal layer, containing product was separated and the aqueous layer was further extracted several times with diethyl ether. The combined ether fractions were dried over magnesium sulphate and filtered through celite. The ether solvent was removed by rotary evaporator (resulting in red oil). The product was purified by column chromatography. Starting material was removed with petrol and the product was then obtained with petrol/10% Et$_2$O as an orange band. The resulting oil was finally dried under vacuum leaving pure product as orange crystals: (11.09 g, 72% yield).

Part (II)

Preparation of 1-dimethylaminomethyl-1'-triphenylsilyl ferrocene

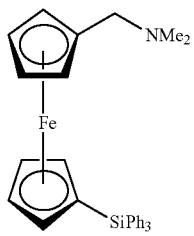

To 1-bromo-1'-triphenylsilyl ferrocene (8 g, 15.29 mmol) in dry diethyl ether (100 ml) was added n-butyllithium (6.73 ml, 16.82 mmol, 1.1 eq) and the reaction was stirred under N$_2$ for 1 hour at room temperature. Dry THF (100 ml) was then added and solution was then cooled to −78° C. (dry ice/acetone bath) and quenched with Eschenmoser's salt (3.11 g, 16.82 mmol, 1.1 eq). The solution was then allowed to warm up to room temperature and further stirred for twelve hours resulting in a yellow solution.

The reaction was then quenched with water, and stirred for a further fifteen minutes. The ethereal layer, containing product was separated and the aqueous layer was further extracted several times with diethyl ether. The combined ether fractions were dried over magnesium sulphate and filtered through celite. The ether solvent was removed by rotary evaporator (resulting in red oil). The product was purified by column chromatography. Starting material was removed with petrol (10% Et$_2$O) and the product was then obtained with 1:1 petrol/Et$_2$O (5% triethylamine). The resulting red oil was finally dried under vacuum leaving pure product as red/orange crystals: (3 g, 39% yield).

Part (III)

Preparation of 1,2-bis-dimethylaminomethyl-1'-triphenylsilyl ferrocene

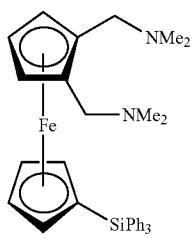

To 1-dimethylaminomethyl-1'-triphenylsilyl ferrocene (2.66 g, 5.30 mmol) in dry diethyl ether (100 ml) was added n-butyllithium (2.55 ml, 6.36 mmol, 1.2 eq) and the reaction was stirred under N$_2$ for 1 hour at room temperature. Dry THF (100 ml) was then added and solution was then cooled to −78° C. (dry ice/acetone bath) and quenched with Eschenmoser's salt (1.08 g, 5.83 mmol, 1.1 eq). The solution was then allowed to warm up to room temperature and further stirred for twelve hours resulting in an orange solution.

The reaction was then quenched with water, and stirred for a further fifteen minutes. The ethereal layer, containing product was separated and the aqueous layer was further extracted several times with diethyl ether. The combined ether fractions were dried over magnesium sulphate and filtered through celite. The ether solvent was removed by rotary evaporator (resulting in red oil). The product was purified by column chromatography. Starting material was removed with petrol (10% Et$_2$O) and the product was then obtained with 1:1 petrol/Et$_2$O (5% triethylamine). The resulting red oil was finally dried under vacuum: (2.94 g, 99% yield).

Part (IV)

1,2-bis(dimethylaminomethyl)-1'-(triphenylsilyl) ferrocene (5.15 g, 9.23 mmol) and di-tert-butylphosphine (4.00 g, 27.40 mmol) were added together in a schlenk flask. To this was added acetic acid:acetic anhydride (100 ml: 10 ml) which had been degassed with nitrogen for 30 minutes. The resultant suspension was then heated to 130° C. for five hours. The solution was then cooled to room temperature and the solvent removed under vacuum. The residue was suspended in methanol (50 ml) and stirred for 20 minutes. The methanol was then removed under vacuum. The residue was then suspended in ethanol (50 ml) and the ethanol suspension heated to reflux. This gave a red solution which was then allowed to cool to room temperature before being placed in the freezer overnight at −20° C. This gave the precipitation of an red-orange solid. The mother liquor was cannula transferred into a clean schlenk and the residue dried under vacuum. This solid was then isolated in the glovebox. Yield=2.8 g, 40%. 95% pure. $^{31}$P {$^1$H} NMR (CDCl$_3$, 161.9 MHz, δ); 23.5 ppm Compound 4

Synthesis of 1,2-bis(di-tert-butylphosphinomethyl)-1'-3-bis(triphenylsilyl)ferrocene Part (I)

Preparation of 1-dimethylaminomethyl-2,1'-bis-triphenylsilyl ferrocene

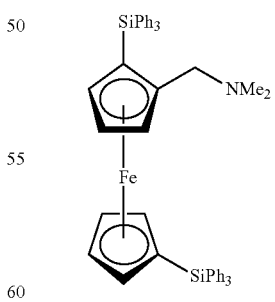

To dimethylaminomethylferrocene (20 g, 82.26 mmol) in dry diethyl ether (300 ml) was added n-butyllithium (82.26 ml, 205.65 mmol, 2.5 eq) and TMEDA (13.66 ml, 90.49 mmol, 1.1 eq) and the reaction was stirred under N$_2$ for 12 hours at room temperature. The solution was then cooled to −78° C. (dry ice/acetone bath) and quenched with chlorotriphenylsilane (50.94 g, 172.75 mmol, 2.1 eq) dissolved in dry THF (200 ml). The solution was then allowed to warm up to room temperature and further stirred for twelve hours resulting in a red solution.

The reaction was then quenched with water, and stirred for a further fifteen minutes. The ethereal layer, containing product was separated and the aqueous layer was further extracted several times with diethyl ether. The combined ether fractions were dried over magnesium sulphate and filtered through celite. The ether solvent was removed by rotary evaporator (resulting in red oil). The product was purified by layering the oil with petrol and Et$_2$O and leaving to crystallize overnight. The liquid residue was decanted and the orange/red crystals were dried under vacuum. A second crop of orange/red crystals were obtained with the layering of the decanted liquid and repeating the process: (42.75 g, 68% yield).

Part (II)

Preparation of 1,2-bis-dimethylaminomethyl-3,1'-bis-triphenylsilyl ferrocene

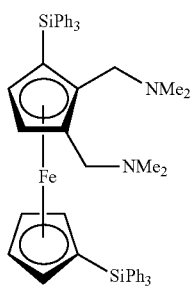

To 1-dimethylaminomethyl-2,1'-bis-triphenylsilyl ferrocene (40 g, 52.63 mmol) in dry diethyl ether (400 ml) was added n-butyllithium (25.26 ml, 63.16 mmol, 1.2 eq) and the reaction was stirred under N$_2$ for 20 hours at room temperature. Dry THF (250 ml) was then added and solution was then cooled to −78° C. (dry ice/acetone bath) and quenched with Eschenmoser's salt (12.65 g, 68.42 mmol, 1.3 eq). The solution was then allowed to warm up to room temperature and further stirred for twelve hours resulting in an orange solution.

The reaction was then quenched with water, and stirred for a further fifteen minutes. The ethereal layer, containing product was separated and the aqueous layer was further extracted several times with diethyl ether. The combined ether fractions were dried over magnesium sulphate and filtered through celite.

The ether solvent was removed by rotary evaporator (resulting in red oil). The product was purified by layering the oil with the minimum Et$_2$O and a layer of petrol and leaving to crystallize overnight. The liquid residue was decanted and the red crystals were dried under vacuum. A second crop of red crystals were obtained with the layering of the decanted liquid and repeating the process: (21.50 g, 50% yield).

Part (III)

The 1,2-bis(dimethylaminomethyl)-1'-3-bis(triphenylsilyl)ferrocene (15.37 g, 18.84 mmol) and di-tert-butylphosphine (8.00 g, 54.79 mmol) were added together in a schlenk flask. To this was added acetic acid:acetic anhydride (100 ml: 10 ml) which had been degassed with nitrogen for 30 minutes. The resultant suspension was then heated to 130° C. for four hours. The solution was then cooled to room temperature and the solvent removed under vacuum. The residue was suspended in methanol (100 ml) and stirred for 20 minutes. The methanol was then removed under vacuum. The residue was then suspended in ethanol (50 ml) and the ethanol suspension heated to 80° C. The resultant suspension was then allowed to cool to room temperature and the ethanol soluble material filtered into a clean schlenk. The residue was dried under vacuum to give a pale orange solid. Yield=8.0 g, 42%. 95% pure. $^{31}$P {$^{1}$H} NMR (CDCl$_3$, 161.9 MHz, 5); 23.9 (s), 20.4 (s) ppm Compound 5

Synthesis of 1,2-bis(di-tert-butylphosphinomethyl)-3-(triphenylsilyl)ferrocene

Part (I)

Preparation of 1-dimethylaminomethyl-2-triphenylsilyl ferrocene

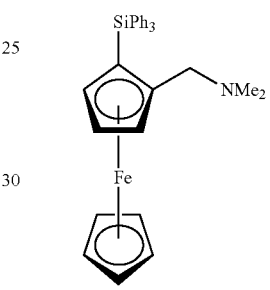

To dimethylaminomethylferrocene (20 g, 82.26 mmol) in dry diethyl ether (300 ml) was added n-butyllithium (41.13 ml, 102.82 mmol, 1.25 eq) and TMEDA (13.66 ml, 90.49 mmol, 1.1 eq) and the reaction was stirred under N$_2$ for 12 hours at room temperature. The solution was then cooled to −78° C. (dry ice/acetone bath) and quenched with chlorotriphenylsilane (25.48 g, 86.38 mmol, 1.05 eq) dissolved in dry THF (200 ml). The solution was then allowed to warm up to room temperature and further stirred for twelve hours resulting in a red solution.

The reaction was then quenched with water, and stirred for a further fifteen minutes. The ethereal layer, containing product was separated and the aqueous layer was further extracted several times with diethyl ether. The combined ether fractions were dried over magnesium sulphate and filtered through celite. The ether solvent was removed by rotary evaporator (resulting in red oil). The product was purified by layering the oil with petrol and Et$_2$O and leaving to crystallize overnight. The liquid residue was decanted and the orange/red crystals were dried under vacuum. A second crop of orange/red crystals were obtained with the layering of the decanted liquid and repeating the process: (25.63 g, 62% yield).

Part (II)

Preparation of 1,2-bis-dimethylaminomethyl-3,1'-bis-triphenylsilyl ferrocene

To 1-dimethylaminomethyl-2-triphenylsilyl ferrocene (20 g, 39.87 mmol) in dry diethyl ether (400 ml) was added n-butyllithium (19.13 ml, 47.84 mmol, 1.2 eq) and the reaction was stirred under N$_2$ for 20 hours at room temperature. Dry THF (250 ml) was then added and solution was then cooled to −78° C. (dry ice/acetone bath) and quenched with Eschenmoser's salt (9.59 g, 51.83 mmol, 1.3 eq). The solution was then allowed to warm up to room temperature and further stirred for twelve hours resulting in an orange solution.

The reaction was then quenched with water, and stirred for a further fifteen minutes. The ethereal layer, containing product was separated and the aqueous layer was further extracted several times with diethyl ether. The combined ether fractions were dried over magnesium sulphate and filtered through celite. The ether solvent was removed by rotary evaporator (resulting in red oil). The product was purified by layering the oil with the minimum Et$_2$O and a layer of petrol and leaving to crystallize overnight. The liquid residue was decanted and the red crystals were dried under vacuum. A second crop of red crystals were obtained with the layering of the decanted liquid and repeating the process: (14.7 g, 66% yield).

Part (III)

The diamine from Part (II) (5.00 g, 8.96 mmol) and di-tert-butylphosphine (3.50 g, 23.97 mmol) were added together in a schlenk flask. To this was added acetic acid: acetic anhydride (100 ml: 10 ml) which had been degassed with nitrogen for 30 minutes. The resultant suspension was then heated to 130° C. for three hours. The solution was then cooled to room temperature and the solvent removed under vacuum. The residue was suspended in methanol (50 ml) and stirred for 20 minutes. The methanol was then removed under vacuum. Pentane (50 ml) was then added and the pentane soluble material cannula transferred into a clean schlenk. The solvent was the removed under vacuum to give an orange/red oily solid. Yield=2.0 g, 30%. 90% pure. $^{31}$P {$^1$H} NMR (CDCl$_3$, 161.9 MHz, 5); 26.0 (s), 20.3 (s) ppm Compound 6

Preparation of 1,2-bis(di-1-(3,5-dimethyladamantyl) phosphinomethyl)-1'-trimethylsilyl-ferrocene Part (I)

Preparation of 1-bromo-1'-trimethylsilyl ferrocene

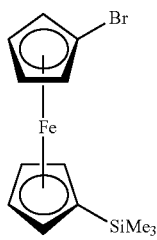

To 1,1'-dibromoferrocene (10 g, 29.08 mmol) in dry THF (200 ml) cooled to −78° C. (dry ice/acetone bath) was added n-butyllithium (11.05 ml, 27.63 mmol, 0.95 eq) and the reaction was stirred under N$_2$ for 30 min. Chlorotrimethylsilane (3.7 ml, 29.08 mmol, 1 eq) was then added dropwise and the solution was then allowed to warm up to room temperature and further stirred for twelve hours resulting in a red solution.

The reaction was then quenched with water, and stirred for a further fifteen minutes. The ethereal layer, containing product was separated and the aqueous layer was further extracted several times with diethyl ether. The combined ether fractions were dried over magnesium sulphate and filtered through celite. The ether solvent was removed by rotary evaporator (resulting in red oil). The product was purified as the initial red band (petrol) by column chromatography. The resulting red oil was finally dried under vacuum: (7.11 g, 73% yield).

Part (II)

Preparation of 1-dimethylaminomethyl-1'-trimethylsilyl ferrocene

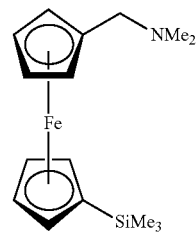

To 1-bromo-1'-trimethylsilyl ferrocene (5.52 g, 16.37 mmol) in dry diethyl ether (100 ml) was added n-butyllithium (7.2 ml, 18.01 mmol, 1.1 eq) and the reaction was stirred under N$_2$ for 1 hour at room temperature. Dry THF (100 ml) was then added and solution was then cooled to −78° C. (dry ice/acetone bath) and quenched with Eschenmoser's salt (3.33 g, 18 mmol, 1 eq). The solution was then allowed to warm up to room temperature and further stirred for twelve hours resulting in a yellow solution.

The reaction was then quenched with water, and stirred for a further fifteen minutes. The ethereal layer, containing product was separated and the aqueous layer was further extracted several times with diethyl ether. The combined ether fractions were dried over magnesium sulphate and filtered through celite. The ether solvent was removed by rotary evaporator (resulting in red oil). The product was purified by column chromatography. Starting material was removed with petrol (10% Et$_2$O) and the product was then obtained with 1:1 petrol/Et$_2$O (5% triethylamine). The resulting red oil was finally dried under vacuum: (4.09 g, 79% yield).

Part (III)

Preparation of 1,2-bis-dimethylaminomethyl-1'-trimethylsilyl ferrocene

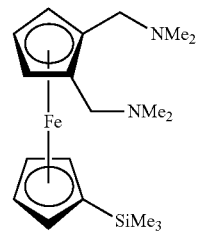

To 1-dimethylaminomethyl-1'-trimethylsilyl ferrocene (3.86 g, 12.24 mmol) in dry diethyl ether (100 ml) was added n-butyllithium (5.88 ml, 14.69 mmol, 1.2 eq) and the reaction was stirred under N$_2$ for 1 hour at room temperature. Dry THF (100 ml) was then added and solution was then cooled to −78° C. (dry ice/acetone bath) and quenched with Eschenmoser's salt (2.50 g, 13.47 mmol, 1.1 eq). The solution was then allowed to warm up to room temperature and further stirred for twelve hours resulting in an orange solution.

The reaction was then quenched with water, and stirred for a further fifteen minutes. The ethereal layer, containing product was separated and the aqueous layer was further extracted several times with diethyl ether. The combined ether fractions were dried over magnesium sulphate and filtered through celite.

The ether solvent was removed by rotary evaporator (resulting in red oil). The product was purified by column chromatography. Starting material was removed with petrol (10% $Et_2O$) and the product was then obtained with 1:1 petrol/$Et_2O$ (5% triethylamine). The resulting red oil was finally dried under vacuum: (4.33 g, 95% yield).

Part (IV)

Synthesis of 1,2-bis(di-1(3,5-dimethyladamantyl) phosphinomethyl)-1'(trimethylsilyl)ferrocene The diamine Part (III) (1.00 g, 2.68 mmol) was dissolved in acetic acid: acetic anhydride (18 ml: 2 ml) which had been degassed with nitrogen for 10 minutes. The diamine solution was then transferred by cannula into a 500 ml schlenk flask containing the dimethyl adamantyl phosphine (1.98 g, 5.36 mmol). The resultant suspension was then heated to 130° C. for five hours. The solution was then cooled to room temperature and the solvent removed under vacuum. The residue was suspended in methanol (50 ml) and stirred for 20 minutes. The methanol was then removed under vacuum. The residue was then washed with ethanol (50 ml) and the ethanol washings removed by cannula. The remaining solid was then dried under vacuum and isolated in the glovebox as a yellow/orange solid. Yield=1.10 g, 41%. 86% pure. $^{31}P\{^1H\}$ NMR ($CDCl_3$, 161.9 MHz, δ); 18.7 ppm. Compound 7

Preparation of 1,2-bis(di-tert-butyl(phosphinomethyl) 3,5,1' tris-triphenylsilyl ferrocene Part (I)

Preparation of 1,2-bis-dimethylaminomethyl-3,5, 1'tris-triphenylsilyl ferrocene

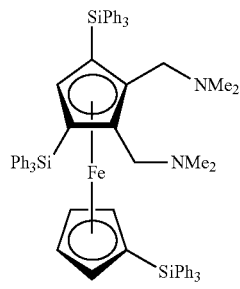

To 1,2-bis-dimethylaminomethyl-3,1'-bis-triphenylsilyl ferrocene (10.2 g, 12.48 mmol) (prepared as in compound 4 above) in dry diethyl ether (200 ml) was added n-butyl-lithium (5.99 ml, 14.98 mmol, 1.2 eq) and the reaction was stirred under $N_2$ for 4 hours at room temperature. The solution was then cooled to −78° C. (dry ice/acetone bath) and quenched dropwise with chlorotriphenylsilane (4.78 g, 16.23 mmol, 1.3 eq) dissolved in the minimum amount of dry diethyl ether. The solution was then allowed to warm up to room temperature and further stirred for twelve hours resulting in a red solution.

The reaction was then quenched with water, and stirred for a further fifteen minutes. The ethereal layer, containing product was separated and the aqueous layer was further extracted several times with diethyl ether. The combined ether fractions were dried over magnesium sulphate and filtered through celite. The ether solvent was removed by rotary evaporator (resulting in red oil). The product was purified by layering the oil with the minimum $Et_2O$ and a layer of petrol and leaving to crystallize overnight. The liquid residue was decanted and the red crystals obtained were dried under vacuum: (10.41 g, 78% yield).

The produced 1,2-bis-dimethylaminomethyl-3,5,1'-tris-triphenylsilyl ferrocene (18.24 mmol) was made into the di-tert-butylphosphine as follows.

Part (II)

Synthesis of 1,2-bis(di-tert-butylphosphinomethyl)-1'-3-5-tris(triphenylsilyl)ferrocene The diamine from Part (I) (10.41 g, 9.69 mmol) and di-tert-butylphosphine (5.00 g, 34.2 mmol) were added together in a schlenk flask. To this was added acetic acid: acetic anhydride (100 ml: 10 ml) which had been degassed with nitrogen for 30 minutes. The resultant suspension was then heated to 130° C. for four hours. The solution was then cooled to room temperature and the solvent removed under vacuum. The residue was suspended in methanol (100 ml) and stirred for 20 minutes. The methanol was then removed under vacuum. Pentane (50 ml) was then added and the pentane soluble material cannula transferred into a clean schlenk. The solvent was the removed under vacuum to give a pale orange/brown solid. Yield=1.7 g, 14%. 95% pure. $^{31}P\{^1H\}$ NMR ($CDCl_3$, 161.9 MHz, δ); 23.9 (s), 20.4 (s) ppm Compound 8

Preparation of 1,2-bis(di-tert-butylphosphinomethyl)-3,1'-bis-trimethylsilyl ferrocene Part (I)

Preparation of 1-dimethylaminomethyl-2,1'-bis-trimethylsilyl ferrocene

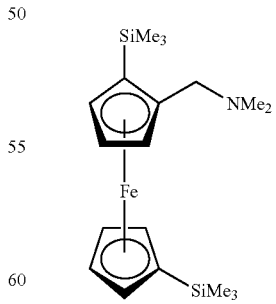

To dimethylaminomethylferrocene (30 g, 123.39 mmol) (Aldrich) in dry diethyl ether (200 ml) was added n-butyl-lithium (123.39 ml, 308.48 mmol, 2.5 eq) and TMEDA (20.48 ml, 135.73 mmol, 1.1 eq) and the reaction was stirred under $N_2$ for 12 hours at room temperature. The solution was then cooled to −78° C. (dry ice/acetone bath) and quenched with chlorotrimethylsilane (34.45 ml, 271.46 mmol, 2.2 eq). The solution was then allowed to warm up to room temperature and further stirred for twelve hours resulting in an orange solution.

The reaction was then quenched with water, and stirred for a further fifteen minutes. The ethereal layer, containing product was separated and the aqueous layer was further extracted several times with diethyl ether. The combined ether fractions were dried over magnesium sulphate and filtered through celite. The ether solvent was removed by rotary evaporator (resulting in red oil). The product was purified by column chromatography (large scale column). Small amounts of starting material were removed with petrol (5% triethylamine) and the product was then obtained with 1:1 petrol/$Et_2O$ (5% triethylamine). The resulting red oil was finally dried under vacuum: (40 g, 84% yield).

Part (II)

Preparation of 1,2-bis-dimethylaminomethyl-3,1′-bis-trimethylsilyl ferrocene

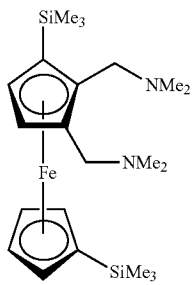

To 1-dimethylaminomethyl-2,1′-bis-trimethylsilyl ferrocene (30 g, 77.42 mmol) in dry diethyl ether (200 ml) was added n-butyllithium (37.2 ml, 92.91 mmol, 1.2 eq) and the reaction was stirred under $N_2$ for 20 hours at room temperature. Dry THF (250 ml) was then added and solution was then cooled to −78° C. (dry ice/acetone bath) and quenched with Eschenmoser's salt (17.18 g, 92.91 mmol, 1.2 eq). The solution was then allowed to warm up to room temperature and further stirred for twelve hours resulting in a red solution.

The reaction was then quenched with water, and stirred for a further fifteen minutes. The ethereal layer, containing product was separated and the aqueous layer was further extracted several times with diethyl ether. The combined ether fractions were dried over magnesium sulphate and filtered through celite. The ether solvent was removed by rotary evaporator (resulting in red oil). The product was purified by column chromatography (large scale column). Small amounts of starting material were removed with petrol (5% triethylamine) and the product was then obtained with 1:1 petrol/$Et_2O$ (5% triethylamine). The resulting red oil was finally dried under vacuum: (32.11 g, 93% yield).

Part (III)

Compound 8 was prepared as compound 3 above using 1,2-dimethylaminomethyl-3,1′-bis-trimethylsilyl ferrocene (9.23 mmol) instead of 1,2-bis(dimethylaminomethyl)-1′-(triphenylsilyl)ferrocene.

Compound A

Synthesis of 1,2-bis(di-tert-butylphosphinomethyl)-4-$CMe_2$Ph-benzene

Part (I)

Synthesis of 4-$CMe_2$Ph-o-xylene

The 3,4-dimethylbenzophenone (15.0 g, 71.43 mmol) was added to a 500 ml schlenk flask, to this was added benzoic acid (150 mg). The solid was then dissolved in toluene (100 ml). To this was then added trimethyl aluminium (2.0M in toluene, 100 ml, 200 mmol). The resultant solution was then heated to 125° C. for hours. The solution was then allowed to cool to room temperature and was then quenched by the very slow addition of water (100 ml). This gave a white suspension, diethyl ether (150 ml) was then added and the suspension filtered. The filtrate was then dried over sodium sulphate and filtered. The filtrate was then dried under vacuum, this gave a colourless oil, yield=13.4 g, 84%.

The 4-$CMe_2$Ph-o-xylene ((13.0 g, 58.0 mmol) from Part I above and NaOBu$^t$ (16.7 g, 174.1 mmol) were added together in a schlenk flask. To this was then added heptane (150 ml) and TMEDA (26.1 ml, 174.1 mmol), Bu$^n$Li (2.5M in hexanes, 69.6 ml, 174.1 mmol) was then added slowly. The addition of the butyl lithium gave an immediate colour change from colourless to yellow to orange to dark red. The resultant solution was then heated to 70° C. for three hours. This gave a dark red suspension. The suspension was cooled to room temperature and the supernatant liquid removed by cannula the brown precipitate residue was then washed with pentane (200 ml). The pentane washings were then removed by cannula. The solid residue was then suspended in pentane (250 ml) and then cooled to 0° C. Bu$^t_2$PCl (19.8 ml, 104.5 mmol) was then added dropwise to the suspension. The resultant suspension was then stirred for overnight. Water (100 ml) was degassed with nitrogen gas for 30 minutes and then added to the suspension. This gave a biphasic solution. The upper (organic phase) was diluted with pentane (100 ml) and the organic phase removed by cannula into a clean schlenk flask. The aqueous layer was then washed with a further 100 ml of pentane and the pentane extracts combined. The pentane extracts were then dried over sodium sulphate and transferred into a clean schlenk flask by cannula. The solvent was then removed under vacuum to give a red/brown oil. Methanol (100 ml) was then added and the resultant suspension heated to reflux, the suspension formed was then allowed to cool to room temperature and the methanol soluble material removed by cannula. The residue was dried under vacuum to give an orange/brown oil. Yield=10.9 g, 45%. $^{31}$P {$^1$H} NMR was consistent with the structure, the compound was cleaned up by conversion to the bis methane sulphonate salt—see below.

Synthesis of bis methane sulphonic acid salt of 1,2-bis(di-tert-butylphosphinomethyl)-4-$CMe_2$Ph-benzene The phosphine (Compound A) (10.9 g, 21.3 mmol) was suspended in methanol (100 ml). To this was added methane sulphonic acid (2.76 ml, 42.6 mmol). The resultant solution was then stirred for one hour. The methanol was then removed under vacuum to give viscous brown oil. Diethyl ether (50 ml) was then added, and the ether soluble material was removed by cannula. The remaining material was then dried under vacuum this gave a sticky yellow solid. Diethyl ether (60 ml) was then added and the solid was stirred in the ether with a spatula. The ether soluble material was then removed and the residue dried under vacuum, this gave a free flowing pale yellow solid. Yield=11.0 g, 85%. 95% pure. $^{31}P\{^{1}H\}$ NMR (CDCl$_3$, 161.9 MHz, δ); 42.6 (br), 39.0 (br) ppm.

Compound B

Synthesis of 1,2-bis(di-tert-butylphosphinomethyl)-4-tert-butyldimethylsilyl benzene Part (I)

Synthesis of 4-tert-butyldimethylsilyl-o-xylene

Magnesium ribbon (2.91 g, 115.41 mmol) was added to a schlenk flask. To this was added a few (3-4) crystals of iodine. THF (150 ml) was then added to give an orange/yellow solution. 4-bromo-o-xylene (19.41 g, 104.91 mmol) was diluted with THF (80 ml) and then added slowly over one hour to the magnesium suspension, the reaction flask being placed in a warm (50° C.) water bath for the duration of the reaction. This gave a dark orange/brown solution with some insoluble magnesium. This solution was then heated to 85° C. for one hour. The solution was then allowed to cool to room temperature before being cannula transferred into a clean schlenk away for the unreacted magnesium. The THF solution was then cooled to −78° C. before a solution of tert-butyldimethylsilyl chloride (15.81 g, 104.91 mmol) in THF (50 ml) was added. The resultant solution was then allowed to stir at −78° C. for thirty minutes before being allowed to warm to room temperature. The resultant solution was then stirred at room temperature overnight. The solution was quenched by the addition of water (100 ml). Ether (100 ml) was then added and the biphasic mixture separated. The aqueous layer was washed with ether (100 ml) and the organic extracts combined. The organic extracts were then dried over sodium sulphate before being filtered. The filtrate was then dried under vacuum to give a white solid. Yield=15.64 g, 68%.

Part (II)

The 4-tert-butyldimethylsilyl-o-xylene (7.5 g, 34.1 mmol) from Part (I) above and NaOBu$^t$ (13.1 g, 136.4 mmol) were added together in a schlenk flask. Heptane (100 ml) was then added followed by TMEDA (20.5 ml, 136.4 mmol), Bu$^n$Li (2.5M in hexanes, 54.5 ml, 136.4 mmol) was then added slowly. The butyl lithium addition gave an immediate colour change from colourless to yellow to orange to dark red. The solution was then heated to 75° C. for three hours. This gave a brown solution with a small amount of precipitate. The solution was then cooled to 0° C. and Bu$^t{}_2$PCl (11 .ml, 62.5 mmol) was then added dropwise to the suspension. The resultant suspension was then stirred overnight. Water (100 ml) was degassed with nitrogen gas for 30 minutes and then added to the suspension. This gave a biphasic solution. The upper (organic phase) was diluted with pentane (150 ml) and the organic phase removed by cannula into a clean schlenk flask. Pentane (150 ml) was added to the aqueous residues and the pentane extracts combined. The pentane extracts were then dried over sodium sulphate and transferred into a clean schlenk flask by cannula. The solvent was then removed under vacuum to give a brown oil. To this was added methanol (50 ml) which give a biphasic solution. This was then heated to reflux (70° C.) before being allowed to cool to room temperature. The methanol soluble material was then cannula transferred into a clean schlenk flask and then placed in the freezer at −20° C. overnight. This gave the formation of a brown oil. The methanol mother liquor was then transferred into a clean schlenk flask and placed in the freezer. Upon standing in the freezer for three days a pale brown solid had formed. The methanol mother liquor was removed and the residue dried under vacuum. This gave a pale brown solid. Yield=0.80 g, 5%. 95% pure. $^{31}P\{^{1}H\}$ NMR (CDCl$_3$, 161.9 MHz, 5); 28.3 (s), 26.0 (s) ppm.

The comparative examples were obtained as follows: —

Comparative 1

1,2-bis(di-tert-butylphosphinomethyl)benzene is available from Aldrich.

Comparative 2

Synthesis of 1,2-bis(di-tert-butylphosphinomethyl)ferrocene

Part (I)

Preparation of 1,2-bis-(dimethylaminomethyl)ferrocene n-Butyllithium (Aldrich, 2.5 molar in hexane, 24 ml, 54 mmol) is added to a solution of (dimethylaminomethyl)ferrocene (Aldrich, 13.13 g, 10.69 ml, 48.97 mmol) in diethyl ether (80 ml) under nitrogen at a temperature of 25° C. and the reaction mixture stirred for 4 hours. The resulting red solution is then cooled to approximately −70° C. in a dry ice/acetone bath and Eschenmosers salt (ICH$_2$NMe$_2$) (Aldrich, 10 g, 54 mmol) is added. The reaction is allowed to warm to room temperature and stirred overnight.

The resultant solution is quenched with excess aqueous sodium hydroxide and the resulting product extracted with diethyl ether (3×80 ml) dried over anhydrous magnesium sulfate, filtered over celite, and volatiles removed in vacuo to yield the crude title compound as a light orange crystalline solid. The crude product is recrystallised from light petrol with cooling to −17° C. and the recrystallised product washed with cold petrol to yield the title compound as a light orange solid (13.2 g, 74%). The compound can be further purified by sublimation to give 8.5 g (52%) of the Part (I) title compound (mpt 74° C.)

$^1$H NMR (250 MHz; CDCl$_3$): δ4.23 (brd, 2H); 4.11-4.10 (t, 1H); 4.04 (s, 5H); 3.43, 3.38, 3.23, 3.18 (AB quartet, 2H); 2.22 (s, 6H).

$^{13}$C NMR (63 MHz; CDCl$_3$): δ83.81; 70.40; 69.25; 66.84; 57.35; 45.23.

Elemental analysis: Found: C, 63.7%; H, 8.9%; N, 9.5%

Calculated: C, 64.0%; H, 8.1%; N, 9.4%

Part (II)

Into a 500 ml schlenk flask was added the di-tert-butyl phosphine (13.3 g, 90.8 mmol) and the 1,2-bis(dimethylaminomethyl)ferrocene (13.6 g, 45.4 mmol). This was then suspended in a mixture of acetic acid:acetic anhydride 100 ml: 30 ml) which had been degassed with nitrogen for 30 minutes. The suspension was then heated to 130° C. and kept at this temperature for two hours. The resultant solution was then allowed to cool to ambient temperature and the solvent removed under vacuum. The resultant sticky solid was suspended in methanol (50 ml) and stirred for 30 minutes. The methanol was then removed under vacuum and the residue suspended in ethanol (50 ml). The ethanol suspension was then heated up to 70° C. The resultant solution stirred was allowed to cool to room temperature before being placed in the freezer at −20° C. overnight. This gave a large amount of an orange crystalline product. The ethanol mother liquor was removed by cannula and the solid dried under vacuum. This gave free following orange crystals. Yield 15.1 g, 57%. $^{31}$P NMR{$^1$H} (CDCl$_3$, 161.9 MHz, δ); 23.6 ppm, 99% pure.

Comparative 3

Synthesis of 1,2-bis(di-1-(3,5-dimethyladamantyl) phosphinomethyl)ferrocene

Part (I)

Preparation of 1-hydroxymethyl-2-dimethylaminomethyl ferrocene n-Butyl lithium (Aldrich, 1.6 molar in diethyl ether, 5.14 ml, 8.24 mmol) is added to a solution of 1-dimethylaminomethyl ferrocene (Aldrich, 1.0 g, 4.12 mmol) in diethyl ether (20 mL) under argon. The reaction is stirred for 3 hours and develops a reddish colour. The solution is then cooled in a dry ice/acetone bath, calcined para-formaldehyde (0.247 g, 2 times excess) added and the resultant mixture stirred overnight at room temperature. The reaction is then quenched with water, extracted with diethyl ether, dried over MgSO$_4$, and filtered over celite. The solvent is removed in vacuo to yield crude title compound. The crude product is applied to a neutral alumina column, which is eluted with petrol/diethyl ether (9:1 ratio) to remove the starting material, 1-dimethylaminomethyl ferrocene. The column is then eluted with substantially pure ethyl acetate to elute the title compound. The ethyl acetate is removed in vacuo, to yield the title compound as an orange oil/crystalline mass.

$^1$H NMR (250 MHz; CDCl$_3$) δ2.131 (s, 6H), δ2.735 (d, 1H, 12.512 Hz), δ3.853 (d, 1H, 12.512 Hz), δ3.984 (dd, 1H, 2.156 Hz), δ4.035 (s, 5H), δ4.060 (dd, 1H, 2.136 Hz) δ4.071 (d, 1H, 12.207 Hz), δ4.154 (m, 1H), δ4.73 (d, 1H, 12.207 Hz).

$^{13}$C NMR (61 MHz; CDCl$_3$) δ7.688, δ84.519, δ70.615, δ68.871, δ68.447, δ65.369, δ60.077, δ58.318, δ44.414 COSY 2D $^1$H NMR

Partly obscured doublet at 4.071 ppm and its coupling to the doublet at 4.73 ppm confirmed.

Infrared spectra (CHCl$_3$) (c.a. 0.06 g/0.8 mL) 2953.8 cm$^{-1}$, 2860.6 cm$^{-1}$, 2826.0 cm$^{-1}$, 2783.4 cm$^{-1}$, 1104.9 cm$^{-1}$ Part (II)

Into a 500 ml schlenk flask was added the dimethyladamantyl phosphine (29.5 g, 82.3 mmol) and the 1-hydroxymethyl-2-dimethylaminomethyl ferrocene (11.2 g, 41.2 mmol) in the glovebox. This was then suspended in a mixture of acetic acid:acetic anhydride (150 ml: 30 ml) which had been degassed with nitrogen for 30 minutes. The suspension was then heated to 130° C. and kept at this temperature for 60 minutes. The resultant solution was then allowed to cool to ambient temperature and the solvent removed under vacuum. The resultant sticky solid was suspended in methanol (50 ml) and stirred for 30 minutes. The methanol was then removed under vacuum and the residue suspended with ethanol (100 ml). The ethanol suspension was then stirred until a yellow/orange powder was formed and a dark red/brown solution. The ethanol soluble material washings were then removed by filtration and the residue dried under vacuum. This gave a free flowing yellow/orange solid which was isolated in the glovebox. Yield 26.7 g, 70.1%. $^{31}$P NMR {$^1$H} (CDCl$_3$, 161.9 MHz, δ); 18.9 ppm, 95% pure.

Test Results

Table 1 shows the activity of six phosphine ligands in catalysis after they have first been heated at 80° C. overnight in the presence of CO/Ethene. In each case the number of moles of palladium, ligand and acid are the same as a standard batch run where the ligands have not been pretreated (Table 2). Hence the gas uptake and weight gain of a treated (premature aged) ligand can be compared to a standard for the untreated ligand. Thermal treatment is used to investigate differences in catalyst stability which would not be evident in a standard 3 hour batch test. In other words, conditions are employed which would result in premature ageing of the catalyst.

It can be seen that the phosphine containing a trimethylsilyl group at the 4 position of the benzene ring retains most of its activity under these ageing conditions whereas the unsubstituted ligand 1,2-bis(di-tert-butylphosphinomethyl) benzene has lost 85% of its activity of an untreated standard. In all the cases where a substituent on the ring is present an improvement over 1,2-bis(di-tert-butylphosphinomethyl) benzene is observed.

TABLE 1

Results for New Ligands and 1,2-Bis (di-tert-butylphosphinomethyl)benzene for comparison

| Ligand | Gas Uptake from 2.251 Reservoir (bar) | Average Max TON MeP of recycle (mol Pd/mol MeP) | Average % Activity of Standard (based on GAS UPTAKE TON) |
|---|---|---|---|
| 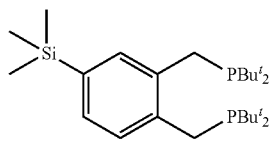 Compound 1 | 20.6 | 88182 | 100.34 |

TABLE 1-continued
Results for New Ligands and 1,2-Bis (di-tert-butylphosphinomethyl)benzene for comparison
| Ligand | Gas Uptake from 2.251 Reservoir (bar) | Average Max TON MeP of recycle (mol Pd/mol MeP) | Average % Activity of Standard (based on GAS UPTAKE TON) |
|---|---|---|---|
| 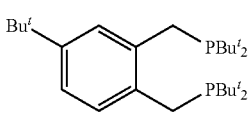 Compound 2 | 12.5 | 52480 | 56.00 |
| 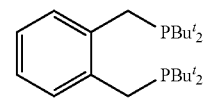 Comparative 1 | 4.4 | 12095 | 13.01 |
| 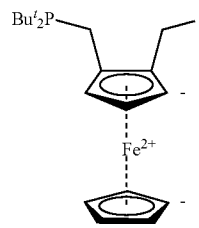 Comparative 2 | 20.3 | 82359 | 78.3 |
| 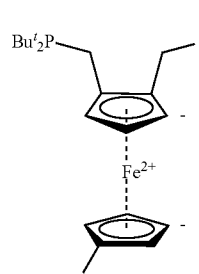 Compound 3 | 21.5 | 86493 | 98.86 |
| 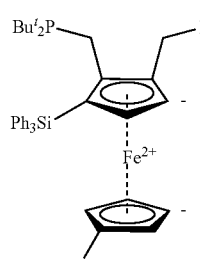 Compound 4 | 21.3 | 86239 | 98.3 |

TABLE 2

Standards used for all aged ligands

| Ligand | Gas Uptake from 2.25l Reservoir (bar) | Average Max TON MeP of recycle (mol Pd/mol MeP) |
|---|---|---|
| Compound 1 (Me₃Si-substituted benzene with two -CH₂PBu$^t_2$ groups) | 23.2 | 87886 |
| Compound 2 (Bu$^t$-substituted benzene with two -CH₂PBu$^t_2$ groups) | 22.4 | 93792 |
| Comparative 1 (benzene with two -CH₂PBu$^t_2$ groups) | 22.9 | 92730 |
| Comparative 2 (ferrocene, 1,1'-bis(CH₂PBu$^t_2$)) | 26.0 | 105206 |
| Compound 3 (ferrocene, 1,1'-bis(CH₂PBu$^t_2$), with Ph₃Si substituent) | 22.0 | 87487 |
| Compound 4 (ferrocene, 1,1'-bis(CH₂PBu$^t_2$), with Ph₃Si substituents on both rings) | 21.7 | 87735 |

Experimental Test Method

Part 1 Ageing

Catalyst solutions were prepared using standard schlenk line techniques. $1.45 \times 10^{-5}$ moles $Pd_2(dba)_3$ and 6 equivalents of the phosphine ligand were weighed out into a 500 ml round bottom flask using a nitrogen purge glovebox. The flask was then transferred to a schlenk line. To this flask was added 172 ml (63.2 wt %) degassed MeP and 116 ml (36.8 wt %) degassed MeOH. To this was added 450 equivalents (420 μl) methane sulphonic acid.

The pre-evacuated autoclave was then charged with the reaction solution. At ambient temperature, 5 bar ethene was added followed by 10 bar 50:50 ethene/CO mixture giving a total of 15 bar gas pressure. The stirrer was then started (1000 rpm) and the autoclave heated to 80° C. Once at this temperature the time was noted and the autoclave was left stirring under these conditions overnight for 17 hours.

The initial solvent composition of 63.2 wt % MeP and 36.8 wt % MeOH was used so that the consumption of 10 bar ethene/CO would result in the production of MeP to yield a new and optimum composition of 70 wt % MeP, 30 wt % MeOH ready for the second part of the experiment.

Part 2 Testing

After this time had elapsed, the autoclave total pressure had dropped to around 5 bar, as the 10 bar of 1:1 ethene/CO had fully reacted. The autoclave was then heated from 80° C. to 100° C. At this temperature ethene was immediately added to bring the pressure up to 10.2 bar (approx 8 bar of ethylene above solvent vapour pressure at 100° C.). It was assumed that all the CO initially present had reacted by this stage meaning only ethene remained in the autoclave. The reaction was immediately initiated by opening the autoclave to a 40 bar 50:50 ethene/CO supply resevoir in a 2.25l cylinder via a pressure regulating valve (Tescom 1500 model no. 26-1025-24-007) supplied by Tescom Corporation set to allow a pressure in the autoclave of 12.2 bar, allowing for a 9:1 ethene/CO ratio to be achieved in the gas phase. This reaction was allowed to proceed for 3 hours, after which the autoclave was cooled and vented.

Part 3 Standard TON Determination

To calculate the average % activity compared with the standard, reaction standard solutions were prepared in the same way, using standard Schlenk line techniques. In a nitrogen purge glove box, 7.8 mg of $Pd_2$ $dba_3$ ($1.45*10^{-5}$ moles) and 6 equivalents of phosphine ligand ($8.7*10^{-5}$ moles), where weighed into a 500 ml round bottom flask. The flask was then transferred to a Schlenk line. The ligand and palladium were then dissolved in 125 ml of degassed methyl propionate. In order to aid complexation, the palladium and ligand were dissolved initially in methyl propionate and stirred for a period of 45 minutes, before addition of further solvents to the solution. This allows for the in situ formation of a neutral, trigonal planar Pd (0) complex [Pd(ligand)(dba)].

After complexation, 175 ml of methyl propionate/methanol mixture (50% by weight methanol, 50% by weight methyl propionate) was degassed and added to the flask. Addition of methane sulfonic acid (MSA), 420 μl, completes the preparation of the catalyst solution. The final composition of the solution is approximately 70 w't % methylpropionate, 30 wt % methanol.

The catalytic solution was added to the pre-evacuated autoclave and heated to 100 C. The autoclave was then pressured with 8 bars of ethene above vapour pressure giving a total pressure of 10.2 bars at 100 C. Next the autoclave was pressured to 12.2 bars with addition of CO:ethene (1:1 gas) charged from the 10 liter reservoir. A regulatory valve ensures that the pressure of the autoclave is maintained throughout the reaction at 12.2 bars through constant injection of gas from the 10 liter reservoir. The pressure of the reservoir as well as the reactor temperature was logged throughout the reaction period of 1 hr.

The moles produced at any point in either reaction are calculated from the drop in reservoir pressure by assuming ideal gas behaviour and 100% selectivity for methyl propionate, which allowed reaction TON and rate to be obtained. The results are shown in Tables 1 and 2.

Recycling Examples

Experimental

Using standard Schlenk line techniques, reaction solutions were prepared by dissolving $1.45 \times 10^{-5}$ moles of Pd and $8.7 \times 10^{-5}$ moles of ligand in 300 ml of solvent consisting of, 70% by weight methyl propionate and 30% by weight methanol. The palladium and ligand were allowed to complex in methyl propionate, before the methanol was added to the mixture. Addition of 420 µl of methane sulfonic acid (450 equivalents) completed the preparation of the catalyst solution.

The catalytic solution was added to the pre-evacuated autoclave and heated to 100° C. The autoclave was then pressured with 8 bars of ethene above vapour pressure giving a total pressure of 10.2 bars at 100° C. Next the autoclave was pressured to 12.2 bars with addition of CO:ethene (1:1 gas) charged from a 10 liter reservoir at higher pressure. A regulatory valve ensures that the pressure of the autoclave is maintained throughout the reaction at 12.2 bars through constant injection of gas from the 10 liter reservoir. The pressure of the reservoir as well as the reactor temperature was logged throughout the reaction period of 3 hrs. The moles produced at any point in the reaction can be calculated from the drop in reservoir pressure by assuming ideal gas behaviour and 100% selectivity for methyl propionate, allowing reaction TON with the particular ligand to be obtained.

After the reaction period, the autoclave was cooled and vented. The reaction solution was collected from the base of the vessel and immediately placed under an inert atmosphere. The solution was then reduced under pressure, to approximately 50 mls. Concentrating the solution removes the methanol (the most volatile component of the mixture) and any traces of CO, both of which can reduce Pd (II) to Pd (0) causing the palladium to precipitate out of solution as metallic palladium. This concentrated solution, was left to stand overnight under an inert atmosphere and was then used to form the basis of the next reaction solution with addition of 200 ml of methyl propionate, 100 ml of methanol and 140 µl of methane sulfonic acid (150 equivalents). Excess acid was added to offset a possible loss in acid upon concentrating of the solution. This recycled material was then added to the autoclave and reacted under the same set of conditions as before. The catalyst was recycled in this way, until a significant drop in reaction TON was observed. Catalyst recycle was discontinued when the TON dropped below 20000 moles MeP/Mole Pd in a single run.

Recycling Experimental Data

The turnover number (TON) expressed in moles of MeP produced per mole of palladium for each recycle experiment is detailed in Table 3. It can be seen that the substituted ferrocene based ligands exhibit enhanced stability over the unsubstituted equivalent.

TABLE 3

| Recycle Number | TON (moles MeP/Mole Pd) | Cumulative TON |
|---|---|---|

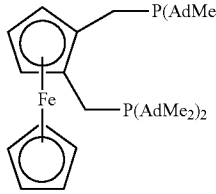

Comparative 3

| Initial Run | 90834 | 90834 |
| Recycle 1 | 79113 | 169947 |
| Recycle 2 | 84796 | 254743 |
| Recycle 3 | 80001 | 334744 |
| Recycle 4 | 71211 | 405955 |
| Recycle 5 | 17936 | 423891 |

Comparative 2

| Initial run | 84772 | 84772 |
| Recycle 1 | 71637 | 156409 |
| Recycle 2 | 69118 | 225527 |
| Recycle 3 | 42847 | 268374 |
| Recycle 4 | 14227 | 282601 |

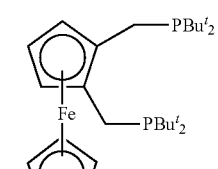

Compound 3

| Initial Run | 90000 | 90000 |
| Recycle 1 | 91968 | 181968 |
| Recycle 2 | 80355 | 262323 |
| Recycle 3 | 72307 | 334630 |
| Recycle 4 | 57821 | 392451 |
| Recycle 5 | 86050 | 478501 |
| Recycle 6 | 32934 | 511436 |
| Recycle 7 | 9534 | 520969 |

Std Batch Experiments in 70 wt % MeP, 30 wt % MeOH of Highly Substituted Ligands Experimental Reaction solutions were prepared, using standard Schlenk line techniques. In a nitrogen purge glove box, 7.8 mg of $Pd_2 dba_3$ ($1.45 \times 10^{-5}$ moles) and 6 equivalents of phosphine ligand ($8.7 \times 10^{-5}$ moles), where weighed into a 500 ml round bottom flask. The flask was then transferred to a Schlenk line. The ligand and palladium was then dissolved in 125 ml of degassed methyl propionate. In order to aid complexation, the palladium and ligand were dissolved initially in methyl propionate and stirred for a period of minutes, before addition of further solvents to the solution. This allows for the in situ formation of a neutral, trigonal planar Pd (0) complex [Pd(ligand)(dba)].

After complexation, 175 ml of methyl propionate/methanol mixture (50% by weight methanol, 50% by weight methyl propionate) was degassed and added to the flask. Addition of methane sulfonic acid (MSA), 420 µl, completes the preparation of the catalyst solution.

The catalytic solution was added to the pre-evacuated autoclave and heated to 100° C. The autoclave was then pressured with 8 bars of ethene above vapour pressure giving a total pressure of 10.2 bars at 100° C. Next the autoclave was pressured to 12.2 bars with addition of CO:ethene (1:1 gas) charged from the 10 liter reservoir. A regulatory valve ensures that the pressure of the autoclave is maintained throughout the reaction at 12.2 bars through constant injection of gas from the 10 liter reservoir. The pressure of the reservoir as well as the reactor temperature was logged throughout the reaction period of 1 hrs. The moles produced at any point in the reaction can be calculated from the drop in reservoir pressure by assuming ideal gas behaviour and 100% selectivity for methyl propionate, allowing reaction TON to be obtained.

TABLE 4

| Maximum Initial rate | Rate after 1 hour | TON after 1 hour |
|---|---|---|
| 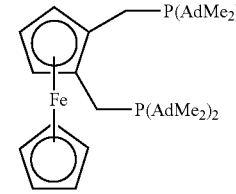 Comparative 3 | | |
| 39787 | 39543 | 35068 |
| Compound 5 | | |
| 67117 | 57599 | 59995 |
| Compound 6 | | |
| 54449 | 53081 | 48798 |

TABLE 4-continued

| Maximum Initial rate | Rate after 1 hour | TON after 1 hour |
|---|---|---|
| 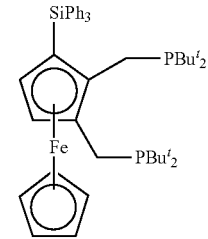 Compound 7 | | |
| 61472 | 56391 | 57137 |
| Compound 8 | | |
| 43823 | 36346 | 38317 |
| 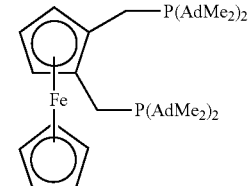 Compound 4 | | |
| 51875 | 45793 | 51052 |
| Compound 3 | | |
| 55565 | 44176 | 47783 |

From the above data it can be seen that substitution of the cyclopentadienyl ring at positions on both the top and bottom rings provides more active and stable catalysts. In addition, bulkier ligands and multiply substituted species provide further improvements in stability.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A novel bidentate ligand of general formula (I)

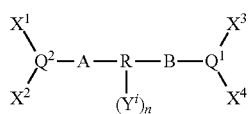

(I)

wherein:
- A and B represent $C_0$ or a methylene group wherein by $C_0$ is meant that the group $Q^1$ or $Q^2$ is connected directly to the R group and there is no methylene group and in this case the other group cannot be $C_0$ and must be a methylene group and, therefore, at least one of A and B is a methylene group;
- R represents a hydrocarbyl aromatic structure or ferrocene structure having at least one aromatic ring to which $Q^1$ and $Q^2$ are each linked, via the respective linking group, on two available adjacent cyclic atoms of the at least one aromatic ring and which is substituted with one or more substituent(s) $Y^i$ on one or more further aromatic cyclic atom(s) of R;
- wherein immediately adjacent cyclic atoms of R on either side of the said two available adjacent cyclic atoms are not substituted;
- wherein the substituent(s) $Y^i$ on the aromatic structure together have a total number $\Sigma t_i$ of atoms other than hydrogen such that $\Sigma t_i$ is greater than or equal to 4, wherein $t_i$ represents the number of atoms other than hydrogen on a particular substituent $Y^i$;
- wherein the groups $X^1$, $X^2$, $X^3$ and $X^4$ independently represent univalent radicals of up to 30 atoms having at least one tertiary carbon atom or $X^1$ and $X^2$ together, $X^3$ and $X^4$ together, or $X^1$ and $X^2$ and $X^3$ and $X^4$ together form a bivalent radical of up to 40 atoms having at least two tertiary carbon atoms wherein each said univalent or bivalent radical is joined via said at least one or two tertiary carbon atoms respectively to the respective atom $Q^1$ or $Q^2$; and
- wherein $Q^1$ and $Q^2$ each independently represent phosphorus, arsenic or antimony;
- wherein each $Y^i$ independently represents $-SR^{40}R^{41}R^{42}$;
- wherein S is selected from Si or;
- wherein $R^{40}$, $R^{41}$ and $R^{42}$ are independently selected from $C_1$ to $C_{10}$ alkyl or five-to-ten-membered carbocyclic aryl;
- wherein n is the total number of substituent(s) $Y^i$; and
- wherein i ranges from 1 to n.

2. The ligand as claimed in claim 1, wherein the substituents are selected from the group consisting of t-butyl; t-alkyl; 2-phenylprop-2-yl; alkylsilyl; $-SiMe_3$; alkylphenyl; or phenylalkyl; which groups are unsubstituted or substituted.

3. The ligand as claimed in claim 1, wherein there are two or more said $Y^i$ substituents.

4. The ligand as claimed in claim 3, wherein two or more said substituents combine to form a further ring structure.

5. The ligand as claimed in claim 1, wherein the hydrocarbyl aromatic structure has from 6 up to 30 cyclic atoms.

6. The ligand as claimed in claim 1, wherein the group $X^1$ represents $CR^1(R^2)(R^3)$, $X^2$ represents $CR^4(R^5)(R^6)$, $X^3$ represents $CR^7(R^8)(R^9)$ and $X^4$ represents $CR^{10}(R^{11})(R^{12})$, wherein $R^1$ to $R^{12}$ represent alkyl, aryl or het.

7. The ligand as claimed in claim 6, wherein one or more of the organic groups $R^1$-$R^3$, $R^4$-$R^6$, $R^7$-$R^9$, or $R^{10}$-$R^{12}$ or, alternatively, $R^1$-$R^6$, $R^7$-$R^{12}$, or $R^1$-$R^6$ and $R^7$-$R^{12}$ when associated with their respective tertiary carbon atom(s) form composite groups which are at least as sterically hindering as t-butyl(s).

8. The ligand as claimed in claim 1, wherein when cyclic, one or more of $X^1$, $X^2$, $X^3$ or $X^4$ represent congressyl, norbornyl, 1-norbornadienyl or adamantyl.

9. The ligand as claimed in claim 1, wherein

is an optionally substituted 2-$Q^2$-tricyclo[3.3.1.1{3,7}]decyl group, or is a ring system of formula 1a

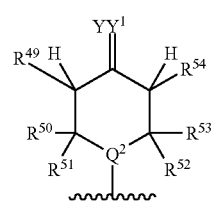

(1a)

wherein $YY^1$ represents oxygen, sulfur or N—$R^{55}$, wherein $R^{55}$ represents hydrogen, alkyl or aryl, wherein $R^{49}$ and $R^{54}$ are each independently selected from the group consisting of hydrogen, alkyl, or aryl, and wherein $R^{50}$, $R^{51}$, $R^{52}$, and $R^{53}$ are each independently selected from the group consisting of alkyl, aryl, or Het, wherein Het is a 4- to 12-membered ring system comprising at least one heteroatom selected from nitrogen, oxygen, and sulfur, optionally substituted.

10. The ligand as claimed in claim 1, wherein

is an optionally substituted 2-$Q^1$-tricyclo[3.3.1.1{3,7}]decyl group, or
is a ring system of formula 1b

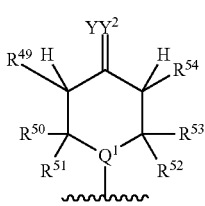

(1b)

wherein $YY^2$ represents oxygen, sulfur or N—$R^{55}$,
wherein $R^{55}$ represents hydrogen, alkyl or aryl,
wherein $R^{49}$ and $R^{54}$ are each independently selected from the group consisting of hydrogen, alkyl, or aryl, and
wherein $R^{50}$, $R^{51}$, $R^{52}$, and $R^{53}$ are each independently selected from the group consisting of alkyl, aryl, or Het, wherein Het is a 4- to 12-membered ring system comprising at least one heteroatom selected from nitrogen, oxygen, and sulfur, optionally substituted.

11. A novel bidentate ligand of general formula (I)

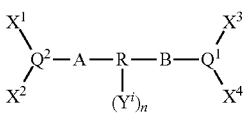

(I)

wherein:
A and B represent C₀ or a methylene group wherein by $C_0$ is meant that the group $Q^1$ or $Q^2$ is connected directly to the R group and there is no methylene group and in this case the other group cannot be $C_0$ and must be a methylene group and, therefore, at least one of A and B is a methylene group;
R represents a hydrocarbyl aromatic structure or ferrocene structure having at least one aromatic ring to which $Q^1$ and $Q^2$ are each linked, via the respective linking group, on two available adjacent cyclic atoms of the at least one aromatic ring and which is substituted with one or more substituent(s) $Y^i$ on one or more further aromatic cyclic atom(s) of R;
wherein immediately adjacent cyclic atoms of R on either side of the said two available adjacent cyclic atoms are not substituted;
wherein the substituent(s) $Y^i$ on the aromatic structure together have a total number $\Sigma t_i$ of atoms other than hydrogen such that $\Sigma t_i$ is greater than or equal to 4, wherein $t_i$ represents the number of atoms other than hydrogen on a particular substituent $Y^i$;
wherein the groups $X^1$, $X^2$, $X^3$ and $X^4$ independently represent univalent radicals of up to 30 atoms having at least one tertiary carbon atom or $X^1$ and $X^2$ together, $X^3$ and $X^4$ together, or $X^1$ and $X^2$ and $X^3$ and $X^4$ together form a bivalent radical of up to 40 atoms having at least two tertiary carbon atoms wherein each said univalent or bivalent radical is joined via said at least one or two tertiary carbon atoms respectively to the respective atom $Q^1$ or $Q^2$; and
wherein $Q^1$ and $Q^2$ each independently represent phosphorus, arsenic or antimony;
wherein each $Y^i$ independently represents —$SR^{40}R^{41}R^{42}$;
wherein S is selected from Si or C;
wherein $R^{40}$, $R^{41}$ and $R^{42}$ are independently selected from $C_1$ to $C_{10}$ alkyl or five-to-ten-membered carbocyclic aryl;
wherein n is the total number of substituent(s) $Y^i$; and
wherein i ranges from 1 to n,
wherein the hydrocarbyl aromatic structure $R(Y^i)_n$ is selected from 4-t-alkylbenzene-1,2-diyl, 5-t-alkylbenzene-1,2-diyl, 4,5-di-t-alkylbenzene-1,2-diyl, 4,5-di-t-butyl-benzene-1,2-diyl, 4-t-butylbenzene-1,2-diyl, 5-t-butylbenzene-1,2-diyl, 2-t-alkyl-naphthalene-8,9-diyl, 3-t-alkyl-naphthalene-8,9-diyl, 4-t-alkyl-naphthalene-8,9-diyl, 5-t-alkyl-naphthalene-8,9-diyl, 2,3-di-t-alkyl-naphthalene-8,9-diyl, 2,4-di-t-alkyl-naphthalene-8,9-diyl, 2,5-di-t-alkyl-naphthalene-8,9-diyl, 3,5-di-t-alkyl-naphthalene-8,9-diyl, 4,5-di-t-alkyl-naphthalene-8,9-diyl, 2,3,4-tri-t-alkyl-naphthalene-8,9-diyl, 2,3,5-tri-t-alkyl-naphthalene-8,9-diyl, 2,4,5-tri-t-alkyl-naphthalene-8,9-diyl, 3,4,5-tri-t-alkyl-naphthalene-8,9-diyl, 2,3,4,5-tetra-t-alkyl-naphthalene-8,9-diyl, 1,3-bis(trimethylsilyl)-isobenzofuran-5,6-diyl, 4-(trimethylsilyl)-benzene-1,2-diyl, 4-(2'-phenylprop-2'-yl)-benzene-1,2-diyl, 4-di-t-butyl-methylsilyl-benzene-1,2-diyl, 4-(t-butyldimethylsilyl)-benzene-1,2-diyl, 4-t-butylsilyl-benzene-1,2-diyl, 4-(tri-t-butylsilyl)-benzene-1,2-diyl, 4-(2'-tert-butylprop-2'-yl)benzene-1,2-diyl, 4-(2',2',3',4',4'-pentamethyl-pent-3'-yl)-benzene-1,2-diyl, 4-t-alkylferrocene-1,2-diyl, 1'-t-alkylferrocene-1,2-diyl, 4,5-di-t-butyl-ferrocene-1,2-diyl, 4-t-butylferrocene-1,2-diyl, 1'-t-butylferrocene-1,2-diyl, 4-(trimethylsilyl)-ferrocene-1,2-diyl, 1'-(trimethylsilyl)-ferrocene-1,2-diyl, 4-(2'-phenylprop-2'-yl)-ferrocene-1,2-diyl, 1'-(2'-phenylprop-2'-yl)-ferrocene-1,2-diyl, 4-di-t-butyl,methylsilyl-ferrocene-1,2-diyl, 1'-di-t-butyl,methylsilyl-ferrocene-1,2-diyl, 4-(t-butyldimethylsilyl)-ferrocene-1,2-diyl, 1'-(t-butyldimethylsilyl)-ferrocene-1,2-diyl, 4-(tri-t-butylsilyl)-ferrocene-1,2-diyl, 1'-(tri-t-butylsilyl)-ferrocene-1,2-diyl, 4-(2'-tert-butylprop-2'-yl)ferrocene-1,2-diyl, 1'-(2'-tert-butylprop-2'-yl)ferrocene-1,2-diyl, 4-(2',2',3',4',4' pentamethyl-pent-3'-yl)-ferrocene-1,2-diyl, or 1'-(2',2',3',4',4' pentamethyl-pent-3'-yl)-ferrocene-1,2-diyl.

12. The ligand as claimed in claim 11, wherein suitable bidentate ligands are 1,2-bis(di-t-butylphosphinomethyl)-4,5-bis-(trimethylsilyl) benzene; 1,2-bis(di-t-butylphosphinomethyl)-4-(trimethylsilyl)benzene; 1,2-bis(2-phosphinomethyl-1,3,5,7-tetramethyl-6,9,10-trioxa-adamantyl)-4,5-bis-(trimethylsilyl)benzene; 1,2-bis(2-phosphinomethyl-1,3,5,7-tetramethyl-6,9,10-trioxa-adamantyl)-4-(trimethylsilyl)benzene; 1,2-bis(di-adamantylphosphinomethyl)-4,5-bis-(trimethylsilyl)benzene; 1,2-bis(di-adamantylphosphinomethyl)-4-(trimethylsilyl)-benzene; 1-(P,P-adamantyl, t-butylphosphinomethyl)-2-(di-t-butylphosphinomethyl)-4,5-bis-(trimethylsilyl)benzene; 1-(P,P-adamantyl, t-butylphosphinomethyl)-2-(di-t-butylphosphinomethyl)-4-(trimethylsilyl)benzene; 1-(2-phosphinomethyl-1,3,5,7-tetramethyl-6,9,10-trioxa-adamantyl)-2-(di-t-butylphosphinomethyl)-4,5-bis-(trimethylsilyl)benzene; 1-(2-phosphinomethyl-1,3,5,7- tetramethyl-6,9,10-trioxa-adamantyl)-2-(di-t-butylphosphinomethyl)-4-(trimethylsilyl)-benzene; 1-(2-phosphinomethyl-1,3,5,7-tetramethyl-6,9,10-trioxa-adamantyl)-2-(diadamantylphosphinomethyl)-4,5-bis-(trimethylsilyl)-benzene; 1-(2-phosphinomethyl-1,3,5,7-tetramethyl-6,9,10-trioxa-adamantyl)-2-(diadamantylphosphinomethyl)-4-(trimethylsilyl) benzene; 1-(di-t-butylphosphinomethyl)-2-(diadamantylphosphinomethyl)-4,5-bis-(trimethylsilyl) benzene; 1-(di-t-butylphosphinomethyl)-2-(diadamantylphosphinomethyl)-4-(trimethylsilyl) benzene; 1,2-bis(2-phosphinomethyl-1,3,5-trimethyl-6,9, 10-trioxatricyclo-{3.3.1.1[3.7]}decyl)-4,5-bis-(trimethylsilyl)benzene; 1,2-bis(2-phosphinomethyl-1,3,5-trimethyl-6,9, 10-trioxatricyclo-{3.3.1.1[3.7]}decyl)-4-(trimethylsilyl)benzene; 1-(2-phosphinomethyl-1,3,5-trimethyl-6,9,10-trioxatricyclo-{3.3.1.1[3.7]}decyl)-2-(di-t-butylphosphinomethyl)-4,5-bis-(trimethylsilyl)benzene; 1-(2-phosphinomethyl-1,3,5-trimethyl-6,9,10-trioxatricyclo-{3.3.1.1[3.7]}decyl)-2-(di-t-butylphosphinomethyl)-4-(trimethylsilyl) benzene; 1-(2-phosphinomethyl-1,3,5-trimethyl-6,9,10-trioxatricyclo-{3.3.1.1[3.7]}decyl)-2-(diadamantylphosphinomethyl)-4,5-bis-(trimethylsilyl) benzene; 1-(2-phosphinomethyl-1,3,5-trimethyl-6,9,10-trioxatricyclo-{3.3.1.1[3.7]}decyl)-2-(diadamantylphosphinomethyl)-4-(trimethylsilyl)benzene; 1,2-bis-perfluoro(2-phosphinomethyl-1,3,5,7-tetramethyl-6,9,10-trioxatricyclo {3.3.1.1[3.7]}-decyl)-4,5-bis-(trimethylsilyl)benzene; 1,2-bis-perfluoro(2-phosphinomethyl-1,3,5,7-tetramethyl-6,9,10-trioxatricyclo {3.3.1.1[3.7]}decyl)-4-(trimethylsilyl)benzene; 1,2-bis-(2-phosphinomethyl-1,3,5,7-tetra(trifluoro-methyl)-6,9,10-trioxatricyclo {3.3.1.1[3.7]}decyl)-4,5-bis-(trimethylsilyl) benzene; 1,2-bis-(2-phosphinomethyl-1,3,5,7-tetra(trifluoro-methyl)-6,9,10-trioxatricyclo {3.3.1.1[3.7]}decyl)-4-(trimethylsilyl) benzene; 1,2-bis(di-t-butylphosphinomethyl)-4,5-di-(2'phenylprop-2'-yl)benzene; 1,2-bis(di-t-butylphosphinomethyl)-4-(2'-phenylprop-2'-yl)benzene; 1,2-bis(di-t-butylphosphinomethyl)-4,5-di-t-butylbenzene; 1,2-bis(di-t-butylphosphinomethyl)-4-t-butylbenzene; 1,2-bis(2-phosphinomethyl-1,3,5,7-tetramethyl-6,9,10-trioxa-adamantyl)-4,5-di-(2'-phenylprop-2'-yl)benzene; 1,2-bis(2-phosphinomethyl-1,3,5,7-tetramethyl-6,9,10-trioxa-adamantyl)-4-2'-phenylprop-2'yl benzene; 1,2-bis(2-phosphinomethyl-1,3,5,7-tetramethyl-6,9,10-trioxa-adamantyl)-4,5-(di-t-butyl)benzene; 1,2-bis(2-phosphinomethyl-1,3,5,7-tetramethyl-6,9,10-trioxa-adamantyl)-4-t-butylbenzene; 1,2-bis(di-adamantylphosphinomethyl)-4,5-di-(2'phenylprop-2'-yl) benzene; 1,2-bis(di-adamantylphosphinomethyl)-4-(2'-phenylprop-2'-yl) benzene; 1,2-bis(di-adamantylphosphinomethyl)-4,5-di-t-butylbenzene; 1,2-bis(di-adamantylphosphinomethyl)-4-t-butyl benzene; 1-(P,P-adamantyl, t-butyl phosphinomethyl)-2-(di-t-butylphosphinomethyl)-4,5-di-(2'phenylprop-2'-yl)benzene; 1-(P,P-adamantyl, t-butyl phosphinomethyl)-2-(di-t-butylphosphinomethyl)-4-(2'-phenylprop-2'-yl)benzene; 1-(P,P-adamantyl, t-butyl phosphinomethyl)-2-(di-t-butylphosphinomethyl)-4,5-di-t-butylbenzene; 1-(P,P-adamantyl, t-butyl phosphinomethyl)-2-(di-t-butylphosphinomethyl)-4-t-butylbenzene; 1-(2-phosphinomethyl-1,3,5,7-tetramethyl-6,9,10-trioxa-adamantyl)-2-(di-t-butylphosphinomethyl)-4,5-di-(2'phenylprop-2'-yl)benzene; 1-(2-phosphinomethyl-1,3,5,7-tetramethyl-6,9,10-trioxa-adamantyl)-2-(di-t-butylphosphinomethyl)-4-(2'-phenylprop-2'-yl) benzene; 1-(2-phosphinomethyl-1,3,5,7-tetramethyl-6,9,10-trioxa-adamantyl)-2-(di-t-butylphosphinomethyl)-4,5-di-t-butylbenzene; 1-(2-phosphinomethyl-1,3,5,7-tetramethyl-6,9,10-trioxa-adamantyl)-2-(di-t-butylphosphinomethyl)-44-butylbenzene; 1-(2-phosphinomethyl-1,3,5,7-tetramethyl-6,9,10-trioxa-adamantyl)-2-(diadamantylphosphinomethyl)-4,5-di-(2'-phenylprop-2'-yl)benzene; 1-(2-phosphinomethyl-1,3,5,7-tetramethyl-6,9,10-trioxa-adamantyl)-2-(diadamantylphosphinomethyl)-4-(2'-phenylprop-2'-yl)benzene; 1-(2-phosphinomethyl-1,3,5,7-tetramethyl-6,9,10-trioxa-adamantyl)-2-(diadamantylphosphinomethyl)-4,5-(di-t-butyl)benzene; 1-(2-phosphinomethyl-1,3,5,7-tetramethyl-6,9,10-trioxa-adamantyl)-2-(diadamantylphosphinomethyl)-4-t-butylbenzene; 1-(di-t-butylphosphinomethyl)-2-(diadamantylphosphinomethyl)-4,5-di-(2'-phenylprop-2'-yl) benzene; 1-(di-t-butylphosphinomethyl)-2-(diadamantylphosphinomethyl)-4-(2'-phenylprop-2'-yl)benzene; 1-(di-t-butylphosphinomethyl)-2-(diadamantylphosphinomethyl)-4,5-(di-t-butyl)benzene; 1-(di-t-butylphosphinomethyl)-2-(diadamantylphosphinomethyl)-44-butylbenzene; 1,2-bis(2-phosphinomethyl-1,3,5-trimethyl-6,9,10-trioxatricyclo-{3.3.1.1[3.7]}decyl)-4,5-di-(2'-phenylprop-2'-yl)benzene; 1,2-bis(2-phosphinomethyl-1,3,5-trimethyl-6,9,10-trioxatricyclo-{3.3.1.1[3.7]}decyl)-4-(2'-phenylprop-2'-yl) benzene; 1,2-bis(2-phosphinomethyl-1,3,5-trimethyl-6,9,10-trioxatricyclo-{3.3.1.1[3.7]}decyl)-4,5-(di-t-butyl)benzene; 1,2-bis (2-phosphinomethyl-1,3,5-trimethyl-6,9,10-trioxatricyclo-{3.3.1.1[3.7]}decyl)-4-t-butylbenzene; 1-(2-phosphinomethyl-1,3,5-trimethyl-6,9, 10-trioxatricyclo-{3.3.1.1[3.7]}decyl)-2-(di-t-butylphosphinomethyl)-4,5-di-(2'-phenylprop-2'-yl)benzene; 1-(2-phosphinomethyl-1,3,5-trimethyl-6,9,10-trioxatricyclo-{3.3.1.1[3.7]}decyl)-2-(di-t-butylphosphinomethyl)-4-(2'-phenylprop-2'-yl)benzene; 1-(2-phosphinomethyl-1,3,5-trimethyl-6,9,10-trioxatricyclo-{3.3.1.1[3.7]}decyl)-2-(di-t-butylphosphinomethyl)-4,5-(di-t-butyl)benzene; 1-(2-phosphinomethyl-1,3,5-trimethyl-6,9,10-trioxatricyclo-{3.3.1.1[3.7]}decyl)-2-(di-t-butylphosphinomethyl)-4-t-butylbenzene; 1-(2-phosphinomethyl-1,3,5-trimethyl-6,9,10-trioxatricyclo-{3.3.1.1[3.7]}decyl)-2-(diadamantylphosphinomethyl)-4,5-di-(2'-phenylprop-2'-yl)benzene; 1-(2-phosphinomethyl-1,3,5-trimethyl-6,9,10-trioxatricyclo-{3.3.1.1[3.7]}decyl)-2-(diadamantylphosphinomethyl)-4-(2'-phenylprop-2'-yl) benzene; 1-(2-phosphinomethyl-1,3,5-trimethyl-6,9,10-trioxatricyclo-{3.3.1.1[3.7]}decyl)-2-(diadamantylphosphinomethyl)-4,5-(di-t-butyl)benzene; 1-(2-phosphinomethyl-1,3,5-trimethyl-6,9,10-trioxatricyclo-{3.3.1.1[3.7]}decyl)-2-(diadamantylphosphinomethyl)-4-t-butylbenzene; 1,2-bis-perfluoro(2-phosphinomethyl-1,3,5,7-tetramethyl-6,9,10-trioxatricyclo {3.3.1.1[3.7]}-decyl)-4,5-di-(2'-phenylprop-2'-yl)benzene; 1,2-bis-perfluoro(2-phosphinomethyl-1,3,5,7-tetramethyl-6,9,10-trioxatricyclo {3.3.1.1[3.7]}decyl)-4-(2'-phenylprop-2'-yl)benzene; 1,2-bis-perfluoro(2-phosphinomethyl-1,3,5,7-tetramethyl-6,9,10-trioxatricyclo {3.3.1.1[3.7]}-decyl)-4,5-(di-t-butyl) benzene; 1,2-bis-perfluoro(2-phosphinomethyl-1,3,5,7-tetramethyl-6,9,10-trioxatricyclo {3.3.1.1[3.7]}decyl)-4-t-butyl benzene; 1,2-bis-(2-phosphinomethyl-1,3,5,7-tetra(trifluoro-methyl)-6,9,10-trioxatricyclo {3.3.1.1[3.7]}decyl)-4,5-di-(2'-phenylprop-2'-yl) benzene; 1,2-bis-(2-phosphinomethyl-1,3,5,7tetra(trifluoro-methyl)-6,9,10-trioxatricyclo {3.3.1.1[3.7]}decyl)-4-(2'-phenylprop-2'-yl) benzene; 1,2-bis-(2-phosphinomethyl-1,3,5,7-tetra(trifluoro-methyl)-6,9,10-trioxatricyclo {3.3.1.1[3.7]}decyl)-4,5-(di-t-butyl) benzene; 1,2-bis-(2-phosphinomethyl-1,3,5,7-tetra(trifluoro-methyl)-6,9,10-trioxatricyclo {3.3.1.1[3.7]}decyl)-4-t-butyl benzene; 1,2-bis(di-t-butylphosphinomethyl)-4,5-bis-(trimethylsilyl) ferrocene; 1,2-bis(di-t-butylphosphinomethyl)-4-

(trimethylsilyl)ferrocene; 1,2-bis(di-t-butylphosphinomethyl)-1'-(trimethylsilyl)ferrocene; 1,2-bis(2-phosphinomethyl-1,3,5,7-tetramethyl-6,9,10-trioxa-adamantyl)-4,5-bis-(trimethylsilyl)ferrocene; 1,2-bis(2-phosphinomethyl-1,3,5,7-tetramethyl-6,9,10-trioxa-adamantyl)-4-(trimethylsilyl)ferrocene; 1,2-bis(2-phosphinomethyl-1,3,5,7-tetramethyl-6,9,10-trioxa-adamantyl)-1'-(trimethylsilyl)ferrocene; 1,2-bis(di-adamantylphosphinomethyl)-4,5 bis-(trimethylsilyl)ferrocene; 1,2-bis(di-adamantylphosphinomethyl)-4-(trimethylsilyl)ferrocene; 1,2-bis(di-adamantylphosphinomethyl)-1'-(trimethylsilyl)ferrocene; 1-(P,P-adamantyl, t-butylphosphinomethyl)-2-(di-t-butylphosphinomethyl)-4-(trimethylsilyl)ferrocene; 1-(P,P-adamantyl, t-butylphosphinomethyl)-2-(di-t-butylphosphinomethyl)-1'-(trimethylsilyl)ferrocene; 1-(2-phosphinomethyl-1,3,5,7-tetramethyl-6,9,10-trioxa-adamantyl)-2-(di-t-butylphosphinomethyl)-4,5-bis-(trimethylsilyl)ferrocene; 1-(2-phosphinomethyl-1,3,5,7-tetramethyl-6,9,10-trioxa-adamantyl)-2-(di-t-butylphosphinomethyl)-4-(trimethylsilyl) ferrocene; 1-(2-phosphinomethyl-1,3,5,7-tetramethyl-6,9,10-trioxa-adamantyl)-2-(di-t-butylphosphinomethyl)-1'-(trimethylsilyl) ferrocene; 1-(2-phosphinomethyl-1,3,5,7-tetramethyl-6,9,10-trioxa-adamantyl)-2-(diadamantylphosphinomethyl)-4,5-bis-(trimethylsilyl)ferrocene; 1-(2-phosphinomethyl-1,3,5,7-tetramethyl-6,9,10-trioxa-adamantyl)-2-(diadamantylphosphinomethyl)-4-(trimethylsilyl)ferrocene; 1-(2-phosphinomethyl-1,3,5,7-tetramethyl-6,9,10-trioxa-adamantyl)-2-(diadamantylphosphinomethyl)-1'-(trimethylsilyl) ferrocene; 1-(di-t-butylphosphinomethyl)-2-(diadamantylphosphinomethyl)-4,5-bis-(trimethylsilyl) ferrocene; 1-(di-t-butylphosphinomethyl)-2-(diadamantylphosphinomethyl)-4-(trimethylsilyl)ferrocene; 1-(di-t-butylphosphinomethyl)-2-(diadamantylphosphinomethyl)-1'-(trimethylsilyl)ferrocene; 1,2-bis(2-phosphinomethyl-1,3,5-trimethyl-6,9,10-trioxatricyclo-{3.3.1.1[3.7]}decyl)-4,5-bis-(trimethylsilyl)ferrocene; 1,2-bis(2-phosphinomethyl-1,3,5-trimethyl-6,9,10-trioxatricyclo-{3.3.1.1[3.7]}decyl)-4-(trimethylsilyl)ferrocene; 1,2-bis(2-phosphinomethyl-1,3,5-trimethyl-6,9,10-trioxatricyclo-{3.3.1.1[3.7]}decyl)-1'-(trimethylsilyl)ferrocene; 1-(2-phosphinomethyl-1,3,5-trimethyl-6,9,10-trioxatricyclo-{3.3.1.1[3.7]}decyl)-2-(di-t-butylphosphinomethyl)-4,5-bis-(trimethylsilyl)ferrocene; 1-(2-phosphinomethyl-1,3,5-trimethyl-6,9,10-trioxatricyclo-{3.3.1.1[3.7]}decyl)-2-(di-t-butylphosphinomethyl)-4-(trimethylsilyl) ferrocene; 1-(2-phosphinomethyl-1,3,5-trimethyl-6,9,10-trioxatricyclo-{3.3.1.1[3.7]}decyl)-2-(di-t-butylphosphinomethyl)-1'-(trimethylsilyl) ferrocene; 1-(2-phosphinomethyl-1,3,5-trimethyl-6,9,10-trioxatricyclo-{3.3.1.1[3.7]}decyl)-2-(diadamantylphosphinomethyl)-4,5-bis-(trimethylsilyl) ferrocene; 1-(2-phosphinomethyl-1,3,5-trimethyl-6,9,10-trioxatricyclo-{3.3.1.1[3.7]}decyl)-2-(diadamantylphosphinomethyl)-4-(trimethylsilyl)ferrocene; 1-(2-phosphinomethyl-1,3,5-trimethyl-6,9,10-trioxatricyclo-{3.3.1.1[3.7]}decyl)-2-(diadamantylphosphinomethyl)-1'-(trimethylsilyl)ferrocene; 1,2-bis-perfluoro(2-phosphinomethyl-1,3,5,7-tetramethyl-6,9,10-trioxatricyclo {3.3.1.1[3.7]}-decyl)-4,5-bis-(trimethylsilyl)ferrocene; 1,2-bis-perfluoro(2-phosphinomethyl-1,3,5,7-tetramethyl-6,9,10-trioxatricyclo {3.3.1.1[3.7]}decyl)-4-(trimethylsilyl)ferrocene; 1,2-bis-perfluoro(2-phosphinomethyl-1,3,5,7-tetramethyl-6,9,10-trioxatricyclo {3.3.1.1[3.7]}decyl)1'-(trimethylsilyl)ferrocene; 1,2-bis-(2-phosphinomethyl-1,3,5,7-tetra(trifluoro-methyl)-6,9,10-trioxatricyclo {3.3.1.1[3.7]}decyl)-4,5-bis-(trimethylsilyl)ferrocene; 1,2-bis-(2-phosphinomethyl-1,3,5,7-tetra(trifluoro-methyl)-6,9,10-trioxatricyclo {3.3.1.1[3.7]}decyl)-4-(trimethylsilyl)ferrocene; 1,2-bis-(2-phosphinomethyl-1,3,5,7-tetra(trifluoro-methyl)-6,9,10-trioxatricyclo {3.3.1.1[3.7]}decyl)-1'-(trimethylsilyl)ferrocene; 1,2-bis(di-t-butylphosphinomethyl)-4-(2'-phenylprop-2'-yl)ferrocene; 1,2-bis(di-t-butylphosphinomethyl)-1'-(2'-phenylprop-2'-yl)ferrocene; 1,2-bis(di-t-butylphosphinomethyl)-4,5-di-t-butylferrocene; 1,2-bis(di-t-butylphosphinomethyl)-4-t-butylferrocene; 1,2-bis(di-t-butylphosphinomethyl)-1'-t-butylferrocene; 1,2-bis(2-phosphinomethyl-1,3,5,7-tetramethyl-6,9,10-trioxa-adamantyl)-4-(2'-phenylprop-2'-yl)ferrocene; 1,2-bis(2-phosphinomethyl-1,3,5,7-tetramethyl-6,9,10-trioxa-adamantyl)-1'-(2'-phenylprop-2'-yl)ferrocene; 1,2-bis(2-phosphinomethyl-1,3,5,7-tetramethyl-6,9,10-trioxa-adamantyl)-4,5-(di-t-butyl)ferrocene; 1,2-bis(2-phosphinomethyl-1,3,5,7-tetramethyl-6,9,10-trioxa-adamantyl)-4-t-butylferrocene; 1,2-bis(2-phosphinomethyl-1,3,5,7-tetramethyl-6,9,10-trioxa-adamantyl)-1'-t-butylferrocene; 1,2-bis(di-adamantylphosphinomethyl)-4-(2'-phenylprop-2'-yl)ferrocene; 1,2-bis(di-adamantylphosphinomethyl)-1'-(2'-phenylprop-2'-yl) ferrocene; 1,2-bis(di-adamantylphosphinomethyl)-4,5-(di-t-butyl)ferrocene; 1,2-bis(di-adamantylphosphinomethyl)-4-t-butylferrocene; 1,2-bis(di-adamantylphosphinomethyl)-1'-t-butylferrocene; 1-(P,P-adamantyl, t-butylphosphinomethyl)-2-(di-t-butylphosphinomethyl)-4-(2'-phenylprop-2'-yl)ferrocene; 1-(P,P-adamantyl, t-butylphosphinomethyl)-2-(di-t-butylphosphinomethyl)-1'-(2'-phenylprop-2'-yl)ferrocene; 1-(P,P-adamantyl, t-butyl phosphinomethyl)-2-(di-t-butylphosphinomethyl)-4,5-(di-t-butyl)ferrocene; 1-(P,P-adamantyl, t-butylphosphinomethyl)-2-(di-t-butylphosphinomethyl)-4-t-butylferrocene; 1-(P,P-adamantyl, t-butylphosphinomethyl)-2-(di-t-butylphosphinomethyl)-1'-t-butylferrocene; 1-(2-phosphinomethyl-1,3,5,7-tetramethyl-6,9,10-trioxa-adamantyl)-2-(di-t-butylphosphinomethyl)-4-(2'-phenylprop-2'-yl)ferrocene; 1-(2-phosphinomethyl-1,3,5,7-tetramethyl-6,9,10-trioxa-adamantyl)-2-(di-t-butylphosphinomethyl)-1'-(2'-phenylprop-2'-yl)ferrocene; 1-(2-phosphinomethyl-1,3,5,7-tetramethyl-6,9,10-trioxa-adamantyl)-2-(di-t-butylphosphinomethyl)-4,5-(di-t-butyl)ferrocene; 1-(2-phosphinomethyl-1,3,5,7-tetramethyl-6,9,10-trioxa-adamantyl)-2-(di-t-butylphosphinomethyl)-44 butylferrocene; 1-(2-phosphinomethyl-1,3,5,7-tetramethyl-6,9,10-trioxa-adamantyl)-2-(di-t-butylphosphinomethyl)-1'-t-butylferrocene; 1-(2-phosphinomethyl-1,3,5,7-tetramethyl-6,9,10-trioxa-adamantyl)-2-(diadamantylphosphinomethyl)-4-(2'-phenylprop-2'-yl) ferrocene; 1-(2-phosphinomethyl-1,3,5,7-tetramethyl-6,9,10-trioxa-adamantyl)-2-(diadamantylphosphinomethyl)-1' (2'-phenylprop-2'-yl)ferrocene; 1-(2-phosphinomethyl-1,3,5,7-tetramethyl-6,9,10-trioxa-adamantyl)-2-(diadamantylphosphinomethyl)-4,5-(di-t-butyl)ferrocene; 1-(2-phosphinomethyl-1,3,5,7-tetramethyl-6,9,10-trioxa-adamantyl)-2-(diadamantylphosphinomethyl)-44-butylferrocene; 1-(2-phosphinomethyl-1,3,5,7-tetramethyl-6,9,10-trioxa-adamantyl)-2-(diadamantylphosphinomethyl)-1'-t-butylferrocene; 1-(di-t-butylphosphinomethyl)-2-(diadamantylphosphinomethyl)-4-(2'-phenylprop-2'-yl)ferrocene; 1-(di-t-butylphosphinomethyl)-2-(diadamantylphosphinomethyl)-1'-(2'-phenylprop-2'-yl)ferrocene; 1-(di-t-butylphosphinomethyl)-2-(diadamantylphosphinomethyl)-4,5-(di-t-butyl)ferrocene; 1-(di-t-butylphosphinomethyl)-2-(diadamantylphosphinomethyl)-44-butylferrocene; 1-(di-t-butylphosphinomethyl)-2-(diadamantylphosphinomethyl)-1'-t-butylferrocene; 1,2-bis (2-phosphinomethyl-1,3,5-trimethyl-6,9,10-trioxatricyclo-{3.3.1.1[3.7]}decyl)-4-(2'-phenylprop-2'-yl) ferrocene; 1,2-bis(2-phosphinomethyl-1,3,5-trimethyl-6,9,10-trioxatricyclo-{3.3.1.1[3.7]}decyl)-1'-(2'-phenylprop-2'-yl) ferrocene; 1,2-bis(2-phosphinomethyl-1,3,5-trimethyl-6,9,10-trioxatricyclo-{3.3.1.1[3.7]}decyl)-4,5-(di-t-butyl)ferrocene; 1,2-bis(2-phosphinomethyl-1,3,5-trimethyl-6,9,10-trioxatricyclo-{3.3.1.1[3.7]}decyl)-4-t-butylferrocene; 1,2-bis(2-phosphinomethyl-1,3,5-trimethyl-6,9,10-trioxatricyclo-{3.3.1.1[3.7]}decyl)-1'-t-butylferrocene; 1-(2-phosphinomethyl-1,3,5-trimethyl-6,9,10-trioxatricyclo-{3.3.1.1[3.7]}decyl)-2-(di-t-butylphosphinomethyl)-4-(2'-phenylprop-2'-yl)ferrocene; 1-(2-phosphinomethyl-1,3,5-trimethyl-6,9,10-trioxatricyclo-{3.3.1.1[3.7]}decyl)-2-(di-t-butylphosphinomethyl)-1'-(2'-phenylprop-2'-yl)ferrocene; 1-(2-phosphinomethyl-1,3,5-trimethyl-6,9,10-trioxatricyclo-{3.3.1.1[3.7]}decyl)-2-(di-t-butylphosphinomethyl)-4,5-(di-t-butyl)ferrocene; 1-(2-phosphinomethyl-1,3,5-trimethyl-6,9,10-trioxatricyclo-{3.3.1.1[3.7]}decyl)-2-(di-t-butylphosphinomethyl)-4-t-butylferrocene; 1-(2-phosphinomethyl-1,3,5-trimethyl-6,9,10-trioxatricyclo-{3.3.1.1[3.7]}decyl)-2-(di-t-butylphosphinomethyl)-1'-t-butylferrocene; 1-(2-phosphinomethyl-1,3,5-trimethyl-6,9,10-trioxatricyclo-{3.3.1.1[3.7]}decyl)-2-(diadamantylphosphinomethyl)-4-(2'-phenylprop-2'-yl)ferrocene; 1-(2-phosphinomethyl-1,3,5-trimethyl-6,9,10-trioxatricyclo-{3.3.1.1[3.7]}decyl)-2-(diadamantylphosphinomethyl)-1'-(2'-phenylprop-2'-yl)ferrocene; 1-(2-phosphinomethyl-1,3,5-trimethyl-6,9,10-trioxatricyclo-{3.3.1.1[3.7]}decyl)-2-(diadamantylphosphinomethyl)-4,5-(di-t-butyl)ferrocene; 1-(2-phosphinomethyl-1,3,5-trimethyl-6,9,10-trioxatricyclo-{3.3.1.1[3.7]}decyl)-2-(diadamantylphosphinomethyl)-4-t-butylferrocene; 1-(2-phosphinomethyl-1,3,5-trimethyl-6,9,10-trioxatricyclo-{3.3.1.1[3.7]}decyl)-2-(diadamantylphosphinomethyl)-1'-t-butylferrocene; 1,2-bis-perfluoro(2-phosphinomethyl-1,3,5,7-tetramethyl-6,9,10-trioxatricyclo {3.3.1.1[3.7]}decyl)-4-(2'-phenylprop-2'-yl) ferrocene; 1,2-bis-perfluoro(2-phosphinomethyl-1,3,5,7-tetramethyl-6,9,10-trioxatricyclo {3.3.1.1[3.7]}decyl)-1'-(2'-phenylprop-2'-yl) ferrocene; 1,2-bis-perfluoro(2-phosphinomethyl-1,3,5,7-tetramethyl-6,9,10-trioxatricyclo {3.3.1.1[3.7]}-decyl)-4,5-(di-t-butyl)ferrocene; 1,2-bis-perfluoro(2-phosphinomethyl-1,3,5,7-tetramethyl-6,9,10-trioxatricyclo {3.3.1.1[3.7]}decyl)-4-t-butylferrocene; 1,2-bis-perfluoro(2-phosphinomethyl-1,3,5,7-tetramethyl-6,9,10-trioxatricyclo {3.3.1.1[3.7]}decyl)-1'-t-butylferrocene; 1,2-bis-(2-phosphinomethyl-1,3,5,7-tetra(trifluoromethyl)-6,9,10-trioxatricyclo {3.3.1.1[3.7]}decyl)-4-(2'-phenylprop-2'-yl)ferrocene; 1,2-bis-(2-phosphinomethyl-1,3,5,7-tetra(trifluoromethyl)-6,9,10-trioxatricyclo {3.3.1.1[3.7]}decyl)-1'-(2'-phenylprop-2'-yl)ferrocene; 1,2-bis-(2-phosphinomethyl-1,3,5,7-tetra(trifluoromethyl)-6,9,10-trioxatricyclo {3.3.1.1[3.7]}decyl)-4,5-(di-t-butyl) ferrocene; 1,2-bis-(2-phosphinomethyl-1,3,5,7-tetra(trifluoromethyl)-6,9,10-trioxatricyclo {3.3.1.1[3.7]}decyl)-4-t-butylferrocene; 1,2-bis-(2-phosphinomethyl-1,3,5,7-tetra(trifluoromethyl)-6,9,10-trioxatricyclo {3.3.1.1[3.7]}decyl)-1'-t-butylferrocene or any of the above ligands wherein one of the methylene groups representing group A or group B is removed so that one of the respective phosphorus atoms is joined directly to the ferrocene or benzene ring representing group R thus forming a $C_3$ bridge connecting the two phosphorus atoms representing $Q_1$ and $Q_2$.

13. The bidentate ligand according to claim 11, wherein the ligands of formula I are selected from:

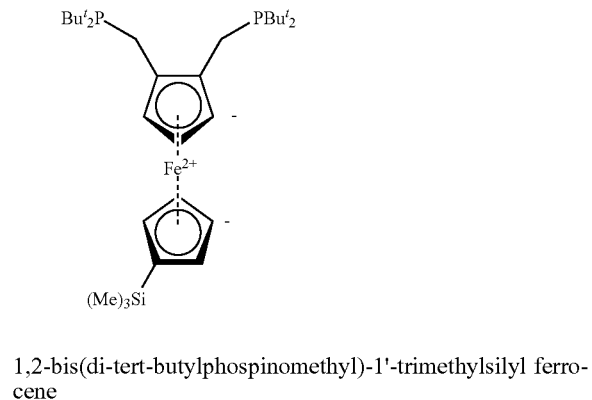

1,2-bis(di-tert-butylphospinomethyl)-1'-trimethylsilyl ferrocene

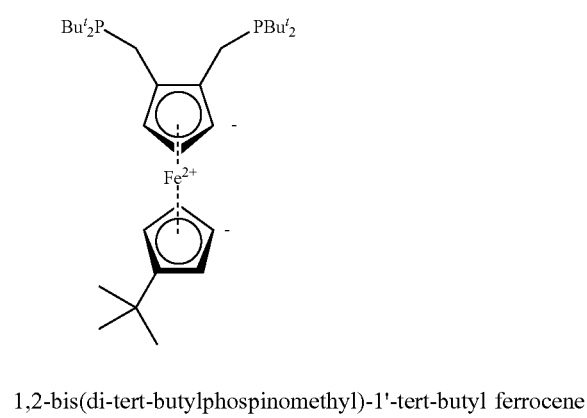

1,2-bis(di-tert-butylphospinomethyl)-1'-tert-butyl ferrocene

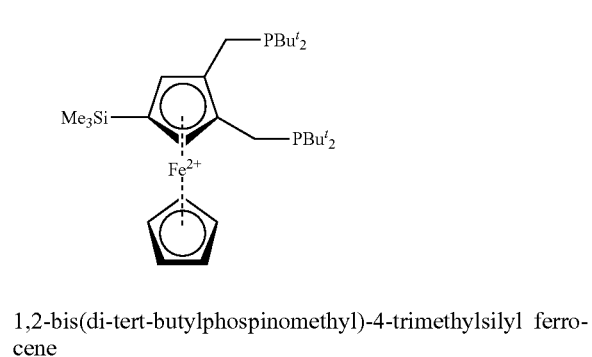

1,2-bis(di-tert-butylphospinomethyl)-4-trimethylsilyl ferrocene

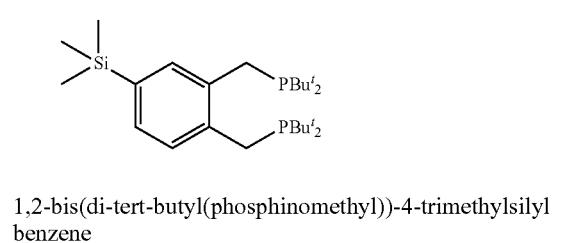

1,2-bis(di-tert-butyl(phosphinomethyl))-4-trimethylsilyl benzene

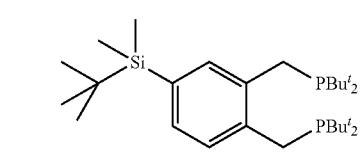

1,2-bis(di-tert-butyl(phosphinomethyl))-4-(tert-butyldimethylsilyl)benzene

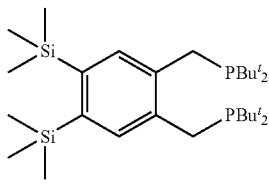

1,2-bis(di-tert-butyl(phosphinomethyl))-4,5-bis(trimethylsilyl)benzene

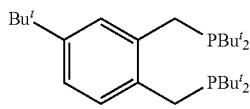

1,2-bis(di-tert-butyl(phosphinomethyl))-4-tert-butyl benzene

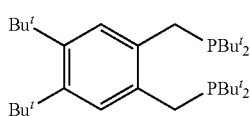

1,2-bis(di-tert-butyl(phosphinomethyl))-4,5-di-tert-butyl benzene

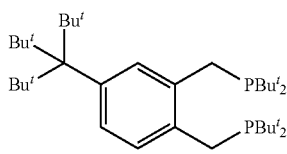

1,2-bis(di-tert-butyl(phosphinomethyl))-4-(tri-tert-butylmethyl)benzene

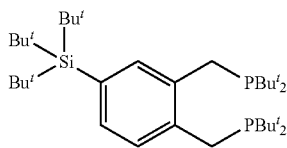

1,2-bis(di-tert-butyl(phosphinomethyl))-4-(tri-tert-butylsilyl)benzene

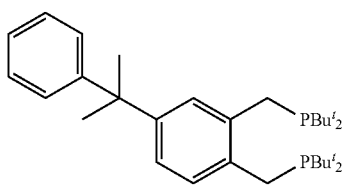

1,2-bis(di-tert-butyl(phosphinomethyl))-4-(2'-phenylprop-2'-yl)benzene

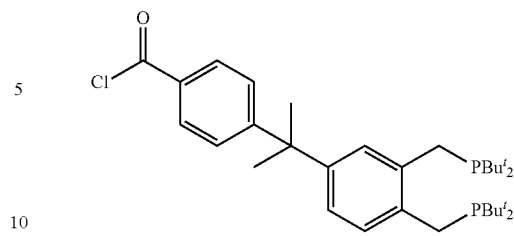

4-(1-{3,4-Bis-[(di-tert-butyl-phosphanyl)-methyl]-phenyl}-1-methyl-ethyl)-benzoyl chloride

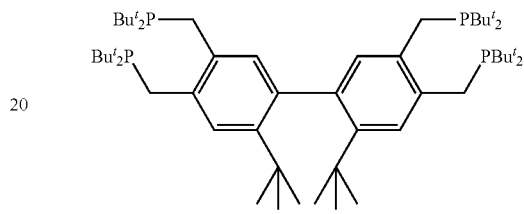

1,2-bis(di-tert-butyl(phosphinomethyl))-4-tertbutyl-5-(2'-tertbutyl-4',5'-bis(di-tert-butyl(phosphinomethyl))phenyl)benzene;

or selected from any one of the above structures wherein one or more of the $X^1$-$X^4$ tertiary carbon bearing groups, t-butyl, attached to the $Q^1$ or $Q^2$ group or $Q^1$ and $Q^2$ group phosphorus is replaced by a suitable alternative selected from adamantyl, 1,3 dimethyl adamantyl, congressyl, norbornyl or 1-norbornodienyl, or $X^1$ and $X^2$ together, $X^3$ and $X^4$ together or $X^1$ and $X^2$ and $X^3$ and $X^4$ together form together with the phosphorus a 2-phospha-tricyclo[3.3.1.1{3,7}]decyl group; or selected from any one of the above structures or alternative structures wherein one of the methylene linking groups representing A or B in formula I is removed so that the respective phosphorus atom is attached directly to the aromatic ring representing R and so that a $C_3$ bridge connects two phosphorus atoms representing $Q_1$ and $Q_2$ in the example structures.

14. A process for the carbonylation of ethylenically unsaturated compounds comprising reacting said compound with carbon monoxide in the presence of a source of hydroxyl groups and of a catalyst system, the catalyst system obtainable by combining:

(a) palladium or a compound thereof: and (b) a bidentate ligand of general formula (I)

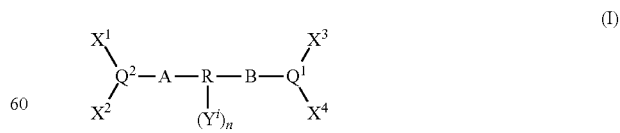

wherein:

A and B represent $C_0$ or a methylene group wherein by $C_0$ is meant that the group $Q^1$ or $Q^2$ is connected directly to the R group and there is no methylene group and in this case the other group cannot be $C_0$ and must be a methylene group and, therefore, at least one of A and B is a methylene group;

R represents a hydrocarbyl aromatic structure or ferrocene having at least one aromatic ring to which $Q^1$ and $Q^2$ are each linked, via the respective linking group when the latter is present, on two available adjacent cyclic atoms of the at least one aromatic ring and which is substituted with one or more substituent(s) $Y^i$ on one or more further aromatic cyclic atom(s) of R;

wherein immediately adjacent cyclic atoms of R on either side of the said two available adjacent cyclic atoms are not substituted;

wherein the substituent(s) $Y^i$ on the aromatic structure together have a total number $\Sigma t_i$ of atoms other than hydrogen such that $\Sigma t_i$ is greater than or equal to 4, wherein $t_i$ represents the number of atoms other than hydrogen on a particular substituent $Y^i$;

wherein the groups $X^1$, $X^2$, $X^3$ and $X^4$ independently represent univalent radicals of up to 30 atoms having at least one tertiary carbon atom or $X^1$ and $X^2$ together, $X^3$ and $X^4$ together or $X^1$ and $X^2$ and $X^3$ and $X^4$ together form a bivalent radical of up to 40 atoms having at least two tertiary carbon atoms wherein each said univalent or bivalent radical is joined via said at least one or two tertiary carbon atoms respectively to the respective atom $Q^1$ or $Q^2$; and wherein $Q^1$ and $Q^2$ each independently represent phosphorus, arsenic or antimony;

wherein each $Y^i$ independently represents $—SR^{40}R^{41}R^{42}$;

wherein S is selected from Si or C;

wherein $R^{40}$, $R^{41}$ and $R^{42}$ are independently selected from $C_1$ to $C_{10}$ alkyl or five-to-ten-membered carbocyclic aryl wherein n is the total number of substituent(s) $Y^i$;

wherein i ranges from 1 to n;

and, optionally, a source of anions.

15. The process as claimed in claim 14, wherein the ethylenically unsaturated compounds are ethylenically unsaturated compounds having from 2 to 50 carbon atoms per molecule, or mixtures thereof.

16. The process as claimed in claim 2, wherein the ethylenically unsaturated compounds are selected from acetylene, methyl acetylene, propyl acetylene, 1,3-butadiene, ethylene, propylene, butylene, isobutylene, pentenes, pentene nitriles, alkyl pentenoates such as methyl 3-pentenoates, pentene acids (such as 2- and 3-pentenoic acid), heptenes, vinyl esters such as vinyl acetate, octenes, dodecenes.

17. A catalyst system obtainable by combining
(a) palladium or a compound thereof; and
(b) a bidentate ligand of general formula (I)

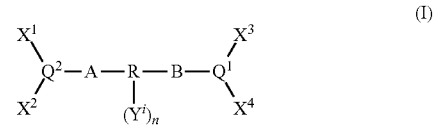

wherein:

A and B represent Co or a methylene group wherein by Co is meant that the group $Q^1$ or $Q^2$ is connected directly to the R group and there is no methylene group and in this case the other group cannot be Co and must be a methylene group and, therefore, at least one of A and B is a methylene group;

R represents a hydrocarbyl aromatic structure or ferrocene structure having at least one aromatic ring to which $Q^1$ and $Q^2$ are each linked, via the respective linking group, on two available adjacent cyclic atoms of the at least one aromatic ring and which is substituted with one or more substituent(s) $Y^i$ on one or more further aromatic cyclic atom(s) of R;

wherein immediately adjacent cyclic atoms of R on either side of the said two available adjacent cyclic atoms are not substituted;

wherein the substituent(s) $Y^i$ on the aromatic structure together have a total of atoms other than hydrogen such that $\Sigma t_i$ is greater than or equal to 4, wherein $t_i$ represents the number of atoms other than hydrogen on a particular substituent $Y^i$;

wherein the groups $X^1$, $X^2$, $X^3$ and $X^4$ independently represent univalent radicals of up to 30 atoms having at least one tertiary carbon atom or $X^1$ and $X^2$ together, $X^3$ and $X^4$ together or $X^1$ and $X^2$ and $X^3$ and $X^4$ together form a bivalent radical of up to 40 atoms having at least two tertiary carbon atoms wherein each said univalent or bivalent radical is joined via said at least one or two tertiary carbon atoms respectively to the respective atom $Q^1$ or $Q^2$; and wherein $Q^1$ and $Q^2$ each independently represent phosphorus, arsenic or antimony;

wherein each $Y^i$ independently represents $—SR^{40}R^{41}R^{42}$;

wherein S is selected from Si or C;

wherein $R^{40}$, $R^{41}$ and $R^{42}$ are independently selected from $C_1$ to $C_{10}$ alkyl or five-to-ten-membered carbocyclic aryl;

wherein n is the total number of substituent(s) $Y^i$; and wherein i ranges from 1 to n;

and, optionally, a source of anions.

* * * * *